United States Patent
Watanabe et al.

(10) Patent No.: US 7,608,409 B2
(45) Date of Patent: Oct. 27, 2009

(54) SCREENING ASSAY USING G-PROTEIN COUPLED RECEPTOR PROTEIN OT7T175

(75) Inventors: Takuya Watanabe, Osaka (JP); Yasuko Terao, Ibaraki (JP); Yasushi Shintani, Ibaraki (JP); Tetsuya Ohtaki, Ibaraki (JP); Kimiko Kanehashi, Ibaraki (JP); Chieko Kitada, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 11/976,414

(22) Filed: Oct. 24, 2007

(65) Prior Publication Data

US 2008/0131976 A1    Jun. 5, 2008

Related U.S. Application Data

(62) Division of application No. 10/771,417, filed on Feb. 5, 2004, now Pat. No. 7,314,754, which is a division of application No. 09/830,428, filed as application No. PCT/JP99/05905 on Oct. 26, 1999, now Pat. No. 6,699,965.

(30) Foreign Application Priority Data

| Oct. 27, 1998 | (JP) | ............................ 1998-305949 |
| Feb. 4, 1999 | (JP) | ............................ 1999-027710 |
| Mar. 4, 1999 | (JP) | ............................ 1999-057207 |
| Sep. 29, 1999 | (JP) | ............................ 1999-276225 |

(51) Int. Cl.
*C07K 14/705* (2006.01)
*G01N 33/53* (2006.01)

(52) U.S. Cl. ........................................ 435/7.1; 530/350

(58) Field of Classification Search ........................ None
See application file for complete search history.

(56) References Cited

U.S. PATENT DOCUMENTS

| 5,436,155 A | 7/1995 | Bell et al. |
| 6,420,526 B1 | 7/2002 | Ruben et al. |
| 2002/0077469 A1 | 6/2002 | Borowsky et al. |

FOREIGN PATENT DOCUMENTS

| EP | 0 853 126 | 7/1998 |
| EP | 853126 | 7/1998 |
| EP | 0 859 052 | 8/1998 |
| EP | 859052 | 8/1998 |
| WO | 96/05302 | 2/1996 |
| WO | 97/13778 | 4/1997 |
| WO | 98/39448 | 9/1998 |
| WO | 00/50563 | 8/2000 |

OTHER PUBLICATIONS

West et al., Chromosome localization and genomic structure of the kiss-1 metastasis suppressor gene (KISS1). Genomics, vol. 54, No. 1, pp. 145-148, 1998.
Hori et al., "Metastin suppresses the motility and growth of CHO cells transfected with its receptor", Biochem. Biophys. Res. Commun., vol. 286, No. 5, pp. 958-963, 2001.
Ringel et al., "Metastin receptor is over expressed in papillary thyroid cancer and activates MAP kinase in thyroid cancer cells", J. Clin. Endocrinol. Metab., vol. 87, No. 5, pp. 2399-2402, 2002.
D. Lorimer et al., "Cloning, Chromosomal Location, and Transcriptional Regulation of the Human Galanin-1 Receptor Gene (GALN1R)[1]", Biochemical and Biophysical Research Communications, 241, pp. 558-564, 1997.
E. Parker et al., "Cloning and characterization of the rat GALR1 galanin receptor from Rin14B insulinoma cells", Molecular Brain Research, 34, pp. 179-189, 1995.
Jeong-Hyung Lee et al., "KiSS-1, a Novel Human Malignant Melanoma Metastasis-Suppressor Gene", Journal of the National Cancer Institute, vol. 88, No. 23, pp. 1731-1737, Dec. 4, 1996.
S. An et al., "Characterization of a Novel Subtype of Human G Protein-Coupled Receptor for Lysophosphatidic Acid", The Journal of Biological Chemistry, vol. 273, No. 14, pp. 7906-7910, Apr. 3, 1998.
A. Jacoby et al., "Structural Organization of the Mouse and Human GALR1 Galanin Receptor Genes (Galnr and GALNR) and Chromosomal Localization of the Mouse Gene", Genomics, 45, pp. 496-508, 1997.
Skolnick et al., "From genes to protein structure and function: novel applications of computational approaches in the genomic era." Trends in Biotech 18(1): 34-39, 2000.

(Continued)

*Primary Examiner*—Bridget E Bunner
(74) *Attorney, Agent, or Firm*—Wenderoth, Lind & Ponack L.L.P.

(57) ABSTRACT

The present invention relates to rat cerebellum-derived and human brain-derived G protein coupled receptor proteins or salts thereof, their partial peptides, amides, esters or salts thereof, ligands to the same, a method/kit for screening compounds that alter the binding property between the ligands and the G protein coupled receptor proteins, compounds obtained by the screening or salts thereof, and antibodies to the G protein coupled receptor proteins.

1 Claim, 9 Drawing Sheets

OTHER PUBLICATIONS

Bork A., "Powers and pitfalls in sequence analysis: the 70% hurdle." Genome Res 10: 398-400, 2000.

Doerks et al., "Protein annotation: detective work for function prediction." Trends in Genetics 14(6): 248-250, 1998.

Tannock and Hill, "The Basic Science of Oncology," 1998, New York: McGraw-Hill, pp. 466-474.

Herzer and Englert, "Nucleic Acid Hybridization," 2001, Molecular Biology Problem Solver: A Laboratory Guide, New York, Wiley-Liss, Inc., pp. 434-435.

Wallace et al., "Oligonucleotide probes for the screening of recombinant DNA libraries," Methods Enzym 152: 432-442, 1987.

Smith et al., "The challenges of genome sequence annotation or The Devil is in the details," Nature Biotech 15: 1222-1223, 1997.

Database EMBL—Online; Aug. 5, 1998, Database Accession No. AC005379.

Database EMBL—Online; Sep. 14, 2001, Database Accession No. U43527.

Lee et al., Journal of the National Cancer Institute, vol. 89, No. 20, Oct. 15, 1997, p. 1549.

Database EMBL—Online; Mar. 15, 1999, Database Accession No. AF115516.

T. Ohtaki et al., "Metastasis Suppressor Gene KiSS-1 Encodes Peptide Ligand of a G-Protein-Coupled Receptor", Letter to Nature, vol. 411, May 31, 2001, pp. 613-617.

Brenner, S.E., "Errors in genome function," Trends in Genetics 15(4): 132-133, 1999.

Bork et al., "Go hunting in sequence databases but watch out for the traps." Trends in Genetics. 12(10): 425-427, 1996.

Wells., J.A., Additivity of mutational effects in proteins. Biochemistry 29(37): 8509-8517, 1990.

Ngo et al., "Computational complexity, protein structure prediction, and the Levinthal paradox." The Protein Folding Problem and Tertiary Structure Prediction, pp. 492-495, 1994.

Phillips, A., The Challenge of gene therapy and DNA delivery. J Pharm Pharmacology 53: 1169-1174, 2001.

Masui et al., "Metastin and its variant forms suppress migration of pancreatic cancer cells," Biochem Biophys Res Comm 315: 85-92, 2004.

Bilban et al., Kisspeptin-10, a KiSS-1/metastin-derived decapeptide, is a physiological invasion inhibtor of primary human trophoblasts. J. Cell Sci 117(Pt 8): 1319-1328, 2004.

Seminara et al., Continuous human metastin 45-54 infusion desensitizes G protein-coupled receptor 54-induced gonadotropoin-releasing hormone release monitored indirectly in the juvenile male Rhesus monkey (Macaca mulatta): a finding with therapeutic implications. Endocrinology 147(5): 2122-2126, 2006.

D. Lee et al., "Discovery of a receptor related to the galanin receptors", FEBS Letters, 446, pp. 103-107, 1999.

Fig. 1

```
         10            20            30            40            50            60
ATG GCC GCA GAG GCG ACG TTG GGT CCG AAC GTG AGC TGG TGG GCT CCG TCC AAC GCT TCG
Met Ala Ala Glu Ala Thr Leu Gly Pro Asn Val Ser Trp Trp Ala Pro Ser Asn Ala Ser 70            80            90           100           110           120
GGA TGC CCG GGC TGC GGT GTC AAT GCC TCG GAT GGC CCA GGC TCC GCG CCA AGG CCC CTG
Gly Cys Pro Gly Cys Gly Val Asn Ala Ser Asp Gly Pro Gly Ser Ala Pro Arg Pro Leu 130           140           150           160           170           180
GAT GCC TGG CTG GTG CCC CTG TTT TTC GCT GCC CTA ATG TTG CTG GGG CTA GTC GGG AAC
Asp Ala Trp Leu Val Pro Leu Phe Phe Ala Ala Leu Met Leu Leu Gly Leu Val Gly Asn 190           200           210           220           230           240
TCA CTG GTC ATC TTC GTT ATC TGC CGC CAC AAG CAC ATG CAG ACC GTC ACC AAT TTC TAC
Ser Leu Val Ile Phe Val Ile Cys Arg His Lys His Met Gln Thr Val Thr Asn Phe Tyr 250           260           270           280           290           300
ATC GCT AAC CTG GCG GCC ACA GAT GTC ACT TTC CTT CTG TGC TGC GTA CCC TTC ACC GCG
Ile Ala Asn Leu Ala Ala Thr Asp Val Thr Phe Leu Leu Cys Cys Val Pro Phe Thr Ala 310           320           330           340           350           360
CTC CTC TAT CCG CTG CCC ACC TGG GTG CTG GGA GAC TTC ATG TGC AAA TTC GTC AAC TAC
Leu Leu Tyr Pro Leu Pro Thr Trp Val Leu Gly Asp Phe Met Cys Lys Phe Val Asn Tyr 370           380           390           400           410           420
ATC CAG CAG GTC TCG GTG CAA GCC ACA TGT GCC ACT TTG ACA GCC ATG AGT GTG GAC CGC
Ile Gln Gln Val Ser Val Gln Ala Thr Cys Ala Thr Leu Thr Ala Met Ser Val Asp Arg
```

Fig. 2

```
        430         440         450         460         470         480
TGG TAC GTG ACT GTG TTC CCG CTG CGT GCA CTT CAC CGC CGC ACT CCG CGC CTG GCC CTG
Trp Tyr Val Thr Val Phe Pro Leu Arg Ala Leu His Arg Arg Thr Pro Arg Leu Ala Leu 490         500         510         520         530         540
ACT GTC AGC CTT AGC ATC TGG GTG GGT TCC GCA GCT GTT TCC GCC CCG GTG CTG GCT CTG
Thr Val Ser Leu Ser Ile Trp Val Gly Ser Ala Ala Val Ser Ala Pro Val Leu Ala Leu 550         560         570         580         590         600
CAC CGC CTG TCG CCC GGG CCT CAC ACC TAC TGC AGT GAG GCG TTT CCC AGC CGT GCC CTG
His Arg Leu Ser Pro Gly Pro His Thr Tyr Cys Ser Glu Ala Phe Pro Ser Arg Ala Leu 610         620         630         640         650         660
GAG CGC GCT TTC GCG CTC TAC AAC CTG CTG GCC CTA TAC CTG CTG CCG CTG CTC GCC ACC
Glu Arg Ala Phe Ala Leu Tyr Asn Leu Leu Ala Leu Tyr Leu Leu Pro Leu Leu Ala Thr 670         680         690         700         710         720
TGC GCC TGC TAC GGT GCC ATG CTG CGC CAC CTG GGC CGC GCC GCT GTA CGC CCC GCA CCC
Cys Ala Cys Tyr Gly Ala Met Leu Arg His Leu Gly Arg Ala Ala Val Arg Pro Ala Pro 730         740         750         760         770         780
ACT GAT GGC GCC CTG CAG GGG CAG CTG CTA GCA CAG CGC GCT GGA GCA GTG CGC ACC AAG
Thr Asp Gly Ala Leu Gln Gly Gln Leu Leu Ala Gln Arg Ala Gly Ala Val Arg Thr Lys 790         800         810         820         830         840
GTC TCC CGG CTG GTG GCC GCT GTC GTC CTG CTC TTC GCC GCC TGC TGG GGC CCG ATC CAG
Val Ser Arg Leu Val Ala Ala Val Val Leu Leu Phe Ala Ala Cys Trp Gly Pro Ile Gln 850         860         870         880         890         900
CTG TTC CTG GTG CTT CAA GCC CTG GGC CCC TCG GGG GCC TGG CAC CCT CGA AGC TAT GCC
Leu Phe Leu Val Leu Gln Ala Leu Gly Pro Ser Gly Ala Trp His Pro Arg Ser Tyr Ala
```

Fig. 3

```
         910           920           930           940           950           960
GCC TAC GCG CTC AAG ATC TGG GCT CAC TGC ATG TCC TAC AGC AAT TCT GCG CTC AAC CCG
Ala Tyr Ala Leu Lys Ile Trp Ala His Cys Met Ser Tyr Ser Asn Ser Ala Leu Asn Pro 970           980           990          1000          1010          1020
CTG CTC TAT GCC TTC CTG GGT TCC CAC TTC AGA CAG GCC TTC TGC CGC GTG TGC CCC TGC
Leu Leu Tyr Ala Phe Leu Gly Ser His Phe Arg Gln Ala Phe Cys Arg Val Cys Pro Cys 1030          1040          1050          1060          1070          1080
GGC CCG CAA CGC CAG CGT CGG CCC CAC GCG TCA GCG CAC TCG GAC CGA GCC GCA CCC CAT
Gly Pro Gln Arg Gln Arg Arg Pro His Ala Ser Ala His Ser Asp Arg Ala Ala Pro His 1090          1100          1110          1120          1130          1140
AGT GTG CCG CAC AGC CGG GCT GCG CAC CCT GTC CGG GTC AGG ACC CCC GAG CCT GGG AAC
Ser Val Pro His Ser Arg Ala Ala His Pro Val Arg Val Arg Thr Pro Glu Pro Gly Asn 1150          1160          1170          1180          1190          1200
CCT GTG GTG CGC TCG CCC TCT GTT CAG GAT GAA CAC ACT GCC CCA CTC TGA
Pro Val Val Arg Ser Pro Ser Val Gln Asp Glu His Thr Ala Pro Leu ***
```

Fig. 5

```
         10         20         30         40         50         60
ATGCACACCG TGGCTACGTC CGGACCCAAC GCGTCCTGGG GGGCACCCGC CAACGCCTCC
METHisThrV alAlaThrSe rGlyProAsn AlaSerTrpG lyAlaProAl aAsnAlaSer 70         80         90        100        110        120
GGCTGCCCGG GCTGTGGCGC CAACGCCTCG GACGGCCCAG TCCCTTCGCC GCGGGCCGTG
GlyCysProG lyCysGlyAl aAsnAlaSer AspGlyProV alProSerPr oArgAlaVal 130        140        150        160        170        180
GACGCCTGGC TCGTGCCGCT CTTCTTCGCG GCGCTGATGC TGCTGGGCCT GGTGGGGAAC
AspAlaTrpL euValProLe uPhePheAla AlaLeuMETL euLeuGlyLe uValGlyAsn 190        200        210        220        230        240
TCGCTGGTCA TCTACGTCAT CTGCCGCCAC AAGCCGATGC GGACCGTGAC CAACTTCTAC
SerLeuVall leTyrVallI eCysArgHis LysProMETA rgThrValTh rAsnPheTyr 250        260        270        280        290        300
ATCGCCAACC TGGCGGCCAC GGACGTGACC TTCCTCCTGT GCTGCGTCCC CTTCACGGCC
IleAlaAsnL euAlaAlaTh rAspValThr PheLeuLeuC ysCysValPr oPheThrAla 310        320        330        340        350        360
CTGCTGTACC CGCTGCCCGG CTGGGTGCTG GGCGACTTCA TGTGCAAGTT CGTCAACTAC
LeuLeuTyrP roLeuProGl yTrpValLeu GlyAspPheM ETCysLysPh eValAsnTyr 370        380        390        400        410        420
ATCCAGCAGG TCTCGGTGCA GGCCACGTGT GCCACTCTGA CCGCCATGAG TGTGGACCGC
IleGlnGlnV alSerValGl nAlaThrCys AlaThrLeuT hrAlaMETSe rValAspArg
```

Fig. 6

```
          430        440        450        460        470        480
     TGGTACGTGA CGGTGTTCCC GTTGCGCGCC CTGCACCGCC GCACGCCCCG CCTGGCGCTG
     TrpTyrValT hrValPhePr oLeuArgAla LeuHisArgA rgThrProAr gLeuAlaLeu 490        500        510        520        530        540
     GCTGTCAGCC TCAGCATCTG GGTAGGCTCT GCGGCGGTGT CTGCGCCGGT GCTCGCCCTG
     AlaValSerL euSerIleTr pValGlySer AlaAlaValS erAlaProVa lLeuAlaLeu 550        560        570        580        590        600
     CACCGCCTGT CACCCGGGCC GCGCGCCTAC TGCAGTGAGG CCTTCCCCAG CCGCGCCCTG
     HisArgLeuS erProGlyPr oArgAlaTyr CysSerGluA laPheProSe rArgAlaLeu 610        620        630        640        650        660
     GAGCGCGCCT TCGCACTGTA CAACCTGCTG GCGCTGTACC TGCTGCCGCT GCTCGCCACC
     GluArgAlaP heAlaLeuTy rAsnLeuLeu AlaLeuTyrL euLeuProLe uLeuAlaThr 670        680        690        700        710        720
     TGCGCCTGCT ATGCGGCCAT GCTGCGCCAC CTGGGCCGGG TCGCCGTGCG CCCCGCGCCC
     CysAlaCysT yrAlaAlaME TLeuArgHis LeuGlyArgV alAlaValAr gProAlaPro 730        740        750        760        770        780
     GCCGATAGCG CCCTGCAGGG GCAGGTGCTG GCAGAGCGCG CAGGCGCCGT GCGGGCCAAG
     AlaAspSerA laLeuGlnGl yGlnValLeu AlaGluArgA laGlyAlaVa lArgAlaLys
```

Fig. 7

```
       790        800        810        820        830        840
  GTCTCGCGGC TGGTGGCCGC CGTGGTCCTG CTCTTCGCCG CCTGCTGGGG CCCCATCCAG
  ValSerArgL euValAlaAl aValValLeu LeuPheAlaA laCysTrpGl yProIleGln 850        860        870        880        890        900
  CTGTTCCTGG TGCTGCAGGC GCTGGGCCCC GCGGGCTCCT GGCACCCACG CAGCTACGCC
  LeuPheLeuV alLeuGlnAl aLeuGlyPro AlaGlySerT rpHisProAr gSerTyrAla 910        920        930        940        950        960
  GCCTACGCGC TTAAGACCTG GGCTCACTGC ATGTCCTACA GCAACTCCGC GCTGAACCCG
  AlaTyrAlaL euLysThrTr pAlaHisCys METSerTyrS erAsnSerAl aLeuAsnPro 970        980        990       1000       1010       1020
  CTGCTCTACG CCTTCCTGGG CTCGCACTTC CGACAGGCCT TCCGCCGCGT CTGCCCCTGC
  LeuLeuTyrA laPheLeuGl ySerHisPhe ArgGlnAlaP heArgArgVa lCysProCys 1030       1040       1050       1060       1070       1080
  GCGCCGCGCC GCCCCCGCCG CCCCCGCCGG CCCGGACCCT CGGACCCCGC AGCCCCACAC
  AlaProArgA rgProArgAr gProArgArg ProGlyProS erAspProAl aAlaProHis 1090       1100       1110       1120       1130       1140
  GCGGAGCTGC ACCGCCTGGG GTCCCACCCG GCCCCCGCCA GGGCGCAGAA GCCAGGGAGC
  AlaGluLeuH isArgLeuGl ySerHisPro AlaProAlaA rgAlaGlnLy sProGlySer 1150       1160       1170       1180       1190       1200
  AGTGGGCTGG CCGCGCGCGG GCTGTGCGTC CTGGGGGAGG ACAACGCCCC TCTCTGA
  SerGlyLeuA laAlaArgGl yLeuCysVal LeuGlyGluA spAsnAlaPr oLeu***
```

SCREENING ASSAY USING G-PROTEIN COUPLED RECEPTOR PROTEIN OT7T175

This is a divisional of Ser. No. 10/771,417, filed Feb. 5, 2004, now U. S. Pat. No. 7,314, 754, which is a divisional of Ser. No. 09/830,428, filed April 26, 2001, now U.S. Pat. No. 6,699,965, which is a U. S. national stage of International Application No. PCT/JP99/059905 filed Oct. 26, 1999.

FIELD OF THE INVENTION

The present invention relates to a novel G protein coupled receptor protein derived from the rat cerebellum and from the human brain, or salts thereof and DNA encoding the same, as well as peptides having a ligand activity to the G protein coupled receptor protein or amides or esters or salts thereof.

BACKGROUND ART

A variety of hormones and neurotransmitt regulate the functions in vivo through specific receptor proteins located in a cell membrane. Many of these receptor proteins mediate the transmission of intracellular signals via activation of guanine nucleotide-binding proteins (hereinafter sometimes referred to as G proteins) with which the receptor is coupled. These receptor proteins possess the common structure, i.e. seven transmembranes domains and are thus collectively referred to as G protein coupled receptors or seven-transmembrane receptors (7TMR).

G protein coupled receptor proteins exist on each functional cell surface of cells and internal organs of a living body and play very important roles as the targets of molecules, for example, hormones, neurotransmitters, physiologically active substances and the like, which molecules control, regulate or adjust the functions of cells and internal organs in the living body. These receptor proteins mediate signal transduction in a cell by binding to physiologically active substances and various reactions such as activation or inhibition of cells is caused by the thus transmitted signal.

To clarify the relation between substances which regulate complex functions in cells and internal organs of various living bodies and their specific receptor proteins, in particular, G protein coupled receptor proteins, would elucidate the functional mechanisms of cells and internal organs in various living body and thus provide a very important means for development of drugs having close relation to such functional mechanisms.

For example, in various organs of a living body, the physiological functions are controlled through regulation by many hormones, hormone-like substances, neurotransmitters or physiologically active substances. In particular, physiologically active substances present in various sites of a living body regulate its physiological functions through each of the corresponding receptor proteins. Still, there are many unknown hormones, neurotransmitters or other physiologically active substances exist in vivo and only a few receptor proteins have been reported on their structures so far. In addition, it yet remains unclear if there will be subtypes of known receptor proteins.

It is also very important for development of pharmaceuticals to clarify the relation between substances that regulate complex functions in vivo and their specific receptor proteins. Furthermore, for efficient screening of agonists and antagonists to receptor proteins in development of pharmaceuticals, it was necessary to elucidate the functions of receptor protein genes expressed in vivo and to express the genes in an appropriate expression system.

In recent years, random analysis of cDNA sequences has been actively performed as a method for analyzing genes expressed in vivo. The sequences of cDNA fragments thus obtained have been registered and published to databases as Expressed Sequence Tag (EST). However, since most EST contains only the sequence information, the function is predictable only with difficulty.

Substances that inhibit the binding of G protein coupled proteins to physiological active substances (i.e., ligands) and substances that bind to physiologically active substances thereby to induce signal transductions similar to those induced by the physiologically active substances (i.e., ligands) have been used for pharmaceuticals as antagonists or agonists specific to the receptors for regulating the biological functions. Accordingly, it is very important to discover a new G protein coupled receptor protein that is not only important for physiological expression in vivo but can be a target for developing pharmaceuticals and to clone the genes (e.g., cDNA), in search for a specific ligand, agonist, and antagonist of the novel G protein coupled receptor.

However, not all G protein coupled receptors have been found. Even now, there are many unknown G protein coupled receptors and those for which the corresponding ligands are unidentified, that is, orphan receptors. It has thus been seriously awaited to explore a novel G protein coupled receptor and clarify its function.

G Protein coupled receptors are useful in searching for a novel physiologically active substance (i.e., ligand) using the signal transduction activity as an index and in searching for agonists and antagonists of the receptor. Even if no physiological ligand is found, agonists and antagonist of the receptor may be prepared by analyzing the physiological activity of the receptor through receptor inactivation experiments (knockout animal). Ligands, agonists, and antagonists of the receptor are expected to be used as prophylactic/therapeutic and diagnostic drugs for diseases associated with dysfunction of the G protein coupled receptor.

Hypofunction or hyperfunction of the G protein coupled receptor due to genetic variation of the receptor in vivo causes some disorders in many cases. In this case, the G protein coupled receptor may be used not only for administration of antagonists or agonists of the receptor, but also for gene therapy by transfer of the receptor gene into the body (or certain specific organs) or by transfer of the antisense nucleic acid to the receptor gene. In such a gene therapy, information on the base sequence of the receptor gene is essentially required for searching of deletion or mutation in the gene. The receptor gene is also applicable as prophylactic/therapeutic and diagnostic drugs for diseases associated with dysfunction of the receptor.

In addition, finding of an endogenous ligand to the receptor or a substance having the ligand activity enables to construct the system for screening antagonists or agonists to the receptor.

DISCLOSURE OF THE INVENTION

The present invention provides a novel and useful G protein coupled receptor protein as described above. That is, the present invention provides a novel G protein coupled receptor protein, its partial peptides and salts thereof, as well as polynucleotides (DNA and RNA, and derivatives thereof) containing polynucleotides (DNA and RNA, and derivatives thereof) encoding the G protein coupled receptor protein and its partial peptides, recombinant vectors containing the polynucleotides, transformants bearing the recombinant vectors, methods for manufacturing the G protein coupled receptor protein and salts thereof, antibodies to the G protein coupled receptor protein, its partial peptides and salts thereof, compounds that alter the expression level of said G protein coupled receptor protein, methods for determination of ligands to the G protein coupled receptor protein, methods for screening compounds (antagonists and agonists) and salts thereof that alter the binding property of ligands and the G protein coupled receptor protein, kits for use in the screening method, compounds (antagonists and agonists) or salts thereof that alter the binding property of ligands obtainable by the screening method or obtainable using the screening kit and the G protein coupled receptor protein, and pharmaceutical compositions comprising the compounds (antagonists and agonists) that alter the binding property of ligands to the G protein coupled receptor protein, or compounds or salts thereof that alter the expression level of the G protein coupled receptor protein.

Furthermore, the present invention provides peptides having a ligand activity to the G protein coupled receptor protein.

The inventors performed extensive studies and as a result, succeeded in isolation of cDNA encoding the novel G protein coupled receptor protein derived from the rat cerebellum and from the human brain, based on the EST information prepared by the degenerated PCR method, resulting in successful analysis of the entire base sequence of the cDNA. The amino acid sequence deduced from the base sequence has supported that the first to the seventh transmembrane domains were observed on the hydrophobic plotting analysis, confirming that the protein encoded by the cDNA is a transmembrane G protein coupled receptor protein passing through the membrane seven times.

The present inventors further proceeded the investigations to explore a peptide having an intracellular Ca ion level-increasing activity to cells that express the G protein coupled receptor protein, using novel peptides found in some known peptides or on the gene data base. As a result, it has made clear that, the C-terminal peptide of a protein encoded by cancer metastasis-suppressor gene KiSS-1 (Genomics, 54, 145-148, 1998) possesses an activity of activating the receptor. KiSS-1 is a protein-encoding gene. The inventors directed their attention to the sequence of the peptide consisting of 54 amino acid residues in KiSS-1 and synthesized the C-terminal partial peptides. The peptide was provided for reactivity tests with the receptor to confirm that the peptide has the ligand activity.

Peptides obtained by excision of the KiSS-1 gene products are expected to suppress tumor metastasis, since their genes are tumor metastasis-suppressor genes. Besides, the peptides are expected to play an important role in the placenta, taking into account that the gene is abundantly expressed in the placenta and hOT7T175, which is a human type receptor of the G protein coupled receptor protein, is expressed also abundantly in the placenta. Expression of the receptor is relatively abundant in human pancreas so that the peptide is expected to exert any physiological function also in the pancreas.

Based on these findings, the present inventors made extensive studies and as a result, the present invention has been accomplished.

Thus, the present invention relates to:

(1) A protein and salts thereof containing the same or substantially the same amino acid sequence as the amino acid sequence shown by SEQ ID NO: 1;

(2) A protein or salts thereof according to (1), wherein the same or substantially the same amino acid sequence is represented by SEQ ID NO: 5;

(3) A partial peptide of the protein according to (1) or esters thereof or amides thereof or salts thereof;

(4) A polynucleotide containing a polynucleotide having the base sequence encoding the protein according to (1);

(5) A polynucleotide according to (4), which is DNA;

(6) A polynucleotide according to (4), which contains the base sequence represented by SEQ ID NO: 2 or SEQ ID NO: 6;

(7) A recombinant vector containing the polynucleotide according to (4);

(8) A transform ant transformed by the recombinant vector according to (7);

(9) A method for manufacturing the protein or salts thereof according to (1), which comprises culturing transformant according to (8) and producing and accumulating the protein according to (1);

(10) Antibodies to the protein or salts thereof according to (1) and to the partial peptide or esters thereof or amides thereof or salts thereof according to (3);

(11) Antibodies according to (10) which are neutralizing antibodies to inactivate signal transduction of the protein according to (1);

(12) A diagnostic composition comprising the antibodies according to (10);

(13) A ligand to the protein or salts thereof according to (1), which is obtainable using the protein or salts thereof according to (1) or using the partial peptide, esters thereof, amides thereof, or salts thereof according to (3);

(14) A pharmaceutical composition comprising the ligand according to (13);

(15) A method for determining the ligand to the protein or salts thereof according to (1), wherein the protein or salts thereof according to (1) or the partial peptide, amides thereof, esters thereof or salts thereof according to (3) are used;

(16) A method for screening a compound or salts thereof that alter the binding property between a ligand and the protein or salts thereof according to (1), which comprises using the protein or salts thereof according to (1), or the partial peptide or amides thereof, esters thereof or salts thereof according to (3);

(17) A kit for screening a compound or salts thereof that alter the binding property between a ligand and the protein or salts thereof according to (1), comprising the protein or salts thereof according to (1), the partial peptide or esters thereof, amides thereof or salts thereof according to (3) are used,

(18) A compound or salts thereof that alter the binding property between a ligand and the protein or salts thereof according to (1), which is obtainable using the screening method according to (16) or the screening kit according to (17);

(19) A pharmaceutical composition comprising the compound or salts thereof that alter the binding property between a ligand and the protein or salts thereof according to (1), which is obtainable using the screening method according to (16) or the screening kit according to (17);

(20) A method for quantifying the protein according to (1), which comprises using the antibodies according to (10);

(21) A peptide, amides thereof, esters thereof or salts thereof according to (21), which, in the amino acid sequence represented by SEQ ID NO: 10, contains a sequence of 47 to 54 amino acids from the N-terminus and comprises 8 to 54 amino acid residues;

(22) A peptide, amides thereof, ester thereof or salts thereof, which, in the amino acid sequence represented by SEQ ID NO: 10, contains the N-terminal 47-54 amino acid sequence at the C-terminus and comprises 8 to 15 amino acid residues;

(23) Amides or salts of the peptide according to (21), comprising the amino acid sequence represented by SEQ ID NO: 11, SEQ ID NO: 12, SEQ ID NO: 13 or SEQ ID NO: 14;

(24) A method for screening according to (16), wherein the ligand is a peptide, amides thereof, esters thereof or salts thereof according to (21); and,

(25) A kit for screening according to (16), wherein the ligand is a peptide, amides thereof, esters thereof or salts thereof according to (21).

The present invention further provides:

(26) a protein or salts thereof according to (1) comprising: (i) an amino acid sequence represented by SEQ ID NO: 1 in which one, two, or more amino acids (preferably 1 to 30 amino acids, more preferably 1 to 9 amino acids, most preferably several (1 or 2) amino acids) are deleted; (ii) an amino acid sequence represented by SEQ ID NO: 1, to which one, two, or more amino acids (preferably 1 to 30 amino acids, more preferably 1 to 10 amino acids, most preferably several (1 or 2) amino acids) are added; (iii) an amino acid sequence represented by SEQ ID NO: 1, in which one, two, or more amino acids (preferably 1 to 30 amino acids, more preferably 1 to 10 amino acids, and most preferably several (1 or 2) amino acids) are substituted by other amino acids; and (iv) a combination of the above amino acid sequences;

(27) A method for screening according to (16), wherein comparison is made between (i) the case where the protein or salts thereof according to (1) or the partial peptide, amides thereof, esters thereof or salts thereof according to (3) are brought in contact with the ligand and (ii) the case where the protein or salts thereof according to (1) or the partial peptide, amides thereof, esters thereof or salts thereof according to (3) are brought in contact with the ligand and a test compound;

(28) A method for screening a compound or salts thereof that alter the binding property between a ligand and the protein or salts thereof according to (1), which comprises measuring and comparing (i) an amount of labeled ligand bound to the protein or salts thereof according to (1) or the partial peptide, amides thereof, esters thereof or salts thereof according to (3) where the labeled ligand is brought in contact with the protein or salts thereof according to (1) or the partial peptide, amides thereof, esters thereof or salts thereof according to (3) and (ii) an amount of labeled ligand bound to the protein or salts thereof according to (1) or the partial peptide or amides thereof, esters thereof or salts thereof according to (3) where the labeled ligand and a test compound are brought in contact with the protein or salts thereof according to (1) or the partial peptide, amides thereof, esters thereof or salts thereof according to (3);

(29) A method for screening a compound or salts thereof that alter the binding property between a ligand and the protein or salts thereof according to (1), which comprises measuring and comparing (i) an amount of labeled ligand bound to cells containing the protein according to (1) upon bringing the labeled ligand in contact with the cells, and (ii) an amount of labeled ligand bound to the cells upon bringing the labeled ligand and a test compound in contact with the cells;

(30) A method for screening a compound or salts thereof that alter the binding property between a ligand and the protein or salts thereof according to (1), which comprises measuring and comparing (i) an amount of labeled ligand bound to a membrane fraction of cells containing the protein according to (1) upon bringing the labeled ligand in contact with the cell membrane fraction, and (ii) an amount of labeled ligand bound to a membrane fraction of the cells upon bringing the labeled ligand and a test compound in contact with the cell membrane fraction;

(31) A method for screening a compound or salts thereof that alter the binding property between a ligand and the protein or salts thereof according to (1), which comprises measuring and comparing (i) an amount of labeled ligand bound to a protein expressed in cell membrane of said transformant of (8) by culturing the transformant where the labeled ligand is brought in contact with the protein expressed, and (ii) an amount of labeled ligand bound to a protein expressed in cell membrane of said transformant (8) by culturing the transformant where the labeled ligand and a test compound are brought in contact with the protein expressed;

(32) A method for screening a compound or salts thereof that alter the binding property between a ligand and the protein or salts thereof according to (1), which comprises measuring and comparing (i) a protein-mediated cell stimulating activity wherein a compound that activates the protein or salts thereof according to (1) is brought in contact with cells containing the protein according to (1) and (ii) a protein-mediated cell stimulating activity wherein a compound that activates the protein or salts thereof according to (1) and a test compound are brought in contact with the cells containing the protein according to (1);

(33) A method for screening a compound or salts thereof that alter the binding property between a ligand and the protein or salts thereof according to (1), which comprises measuring and comparing (i) a protein-mediated cell stimulating activity wherein a compound that activates the protein or salts thereof according to (1) is brought in contact with a protein expressed in a cell membrane of the transformant according to (8) by culturing the transformant and (ii) a protein-mediated cell stimulating activity wherein a compound that activates the protein or salts thereof according to (1) and a test compound are brought in contact with a protein expressed in a cell membrane of the transformant according to (8) by culturing the transformant;

(34) A method for screening according to (32) or (33), wherein the compound that activates the protein according to (1) is a peptide, amides thereof, esters thereof or salts thereof according to (21);

(35) A compound or salts thereof that alter the binding property between a ligand and the G-protein coupled receptor protein or salts thereof according to (1), which is obtainable by the method for screening according to (27) through (34);

(36) A pharmaceutical composition comprising a compound or salts thereof that alter the binding property between a ligand and the protein or salts thereof according to (1), which is obtainable by the method for screening according to (27) through (34);

(37) A kit for screening according to (17), comprising a cell containing the protein according to (1);

(38) A kit for screening according to (17), comprising a cell membrane fraction of cell containing the protein according to (1);

(39) A kit for screening according to (17), comprising a protein expressed in a cell membrane of the transformant according to (8) by culturing the transformant;

(40) A compound or salts thereof that alter the binding property between a ligand and the protein or salts thereof according to (1), which is obtainable using the kit for screening according to (37) through (39);

(41) A pharmaceutical composition comprising a compound or salts thereof that alter the binding property between a ligand and the G-protein coupled receptor protein or salts thereof according to (1), which is obtainable using the kit for screening according to (37) through (39);

(42) A method for quantifying the protein or salts thereof according to (1), or the partial peptide, amides thereof, esters thereof or salts thereof according to (3), which comprises bringing the antibodies according to (10) in contact with the protein or salts thereof according to (1) or partial peptide, amides thereof, esters thereof or salts according to (3);

(43) A method for quantifying the protein or salts thereof according to (1), or the partial peptide, amides thereof, esters thereof or salts thereof according to (3), in a sample solution, which comprises competitively reacting the antibodies according to (10) with a sample solution and the labeled protein or salts thereof according to (1) or the labeled partial peptide, amides thereof, esters thereof or salts thereof according to (3) and, measuring ratio of the labeled protein or salts thereof according to (1) or the labeled partial peptide, amides thereof, esters thereof or salts thereof according to (3), which are bound to the antibodies; and,

(44) A method for quantifying the protein or salts thereof according to (1) or the partial peptide, amides thereof, esters thereof or salts thereof according to (3), in a sample solution, which comprises reacting a sample solution simultaneously or sequentially with antibodies of (10) immobilized on a carrier and labeled antibodies of (10) and then measuring the activity of a labeling agent on the immobilized carrier.

BRIEF DESCRIPTION OF THE DRAWINGS

FIG. 1 shows the base sequence (SEQ ID NO: 2) of DNA encoding the rat cerebellum-derived novel G protein coupled receptor protein rOT7T175 of the present invention obtained in Example 1, and the amino acid sequence (SEQ ID NO: 1) deduced from the above DNA sequence (continued to FIG. 2).

FIG. 2 shows the base sequence (SEQ ID NO: 2) of DNA encoding the rat cerebellum-derived novel G protein coupled receptor protein rOT7T 175 of the present invention obtained in Example 1, and the amino acid sequence (SEQ ID NO: 1) deduced from the above DNA sequence (continued from FIG. 1, continued to FIG. 3).

FIG. 3 shows the base sequence (SEQ ID NO: 2) of DNA encoding the rat cerebellum-derived novel G protein coupled receptor protein rOT7Tl75 of the present invention obtained in Example 1, and the amino acid sequence (SEQ ID NO: 1) deduced from the above DNA sequence (continued from FIG. 2).

FIG. 5 shows the base sequence (SEQ ID NO: 6) of DNA encoding the human brain-derived novel G protein coupled receptor protein hOT7T 175 of the present invention obtained in Example 2, and the amino acid sequence (SEQ ID NO: 5) deduced from the above DNA sequence (continued to FIG. 6).

FIG. 6 shows the base sequence (SEQ ID NO: 6) of DNA encoding the human brain-derived novel G protein coupled receptor protein hOT7T175 of the present invention obtained in Example 2, and the amino acid sequence (SEQ ID NO: 5) deduced from the above DNA sequence (continued from FIG. 5, continued to FIG. 7).

FIG. 7 shows the base sequence (SEQ ID NO: 6) of DNA encoding the human brain-derived novel G protein coupled receptor protein hOT7Tl75 of the present invention obtained in Example 2, and the amino acid sequence (SEQ ID NO: 5) deduced from the above DNA sequence (continued from FIG. 6).

BEST MODE OF EMBODIMENT OF THE INVENTION

Figure 4:
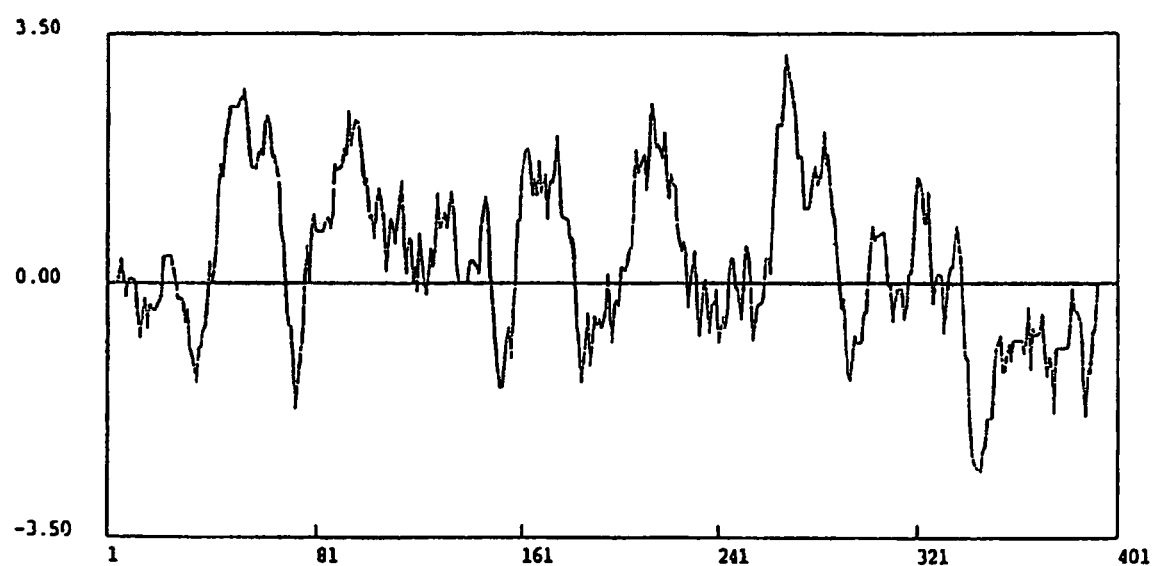
FIG. 4 shows the hydrophobic plotting of the rat cerebellum-derived G protein coupled receptor protein rOT7T175 of the present invention prepared based on the amino acid sequence shown in FIGS. 1 through 3.

The protein of the present invention (receptor protein, G protein coupled receptor protein; hereinafter often referred to as "receptor protein of the present invention") is the protein which has the same or substantially the same amino acid sequence as that represented by SEQ ID NO: 1 (the amino acid sequence shown by FIGS. 1 through 3).

The receptor protein of the present invention may be any peptide derived from any cells of human and another mammal (e.g., guinea pig, rat, mouse, rabbit, swine, sheep, bovine, monkey, etc.), for example, spleen cells, nerve cells, glia cells, β cells of pancreas, bone marrow cells, mesangial cells, Langerhans' cells, epidermal cells, epithelial cells, endothelial cells, fibroblasts, fibrocytes, muscular cells, fat cells, immunocytes (e.g., macrophage, T cells, B-cells, natural killer cells, mast cells, neutrophils, basophils, eosinophils, monocytes, etc.), megakaryocytes, synovial cells, chondrocytes, osteocytes, osteoblasts, osteoclasts, mammary gland cells, hepatocytes or interstitial cells, or precursor cells, stem cells or cancer cells of these cells and the like; cells of hemocyte type; or any tissues containing such cells, for example, brain, various parts of the brain (e.g., olfactory bulb, amygdala, cerebral basal ganglia, hippocampus, thalamus, hypothalamus, substhanlamic nucleus, cerebral cortex, medulla oblongata, cerebellum, occipital pole, frontal lobe, temporal lobe, putamen, caudate nucleus, corpus callosum, substantia nigra), spinal cord, pituitary, stomach, pancreas, kidney, liver, genital gland, thyroid gland, gallbladder, bone marrow, adrenal gland, skin, muscle, lung, digestive tract (e.g., large intestine, small intestine), blood vessel, heart, thymus, spleen, submandibular gland, peripheral blood, peripheral hemocyte, prostate, testicle, testis, ovary, placenta, uterus, bone, joint, skeletal muscle and the like, in particular, brain and various parts of the brain. The peptide may also be a synthetic one.

The amino acid sequence which has the same or substantially the same as that represented by SEQ ID NO: 1 includes an amino acid sequence having at least about 50% homology, preferably at least about 70% homology, more preferably at least about 80% homology, much more preferably at least about 90% homology, most preferably at least about 95% homology, to the amino acid sequence represented by SEQ ID NO: 1.

Specific examples of the protein include a protein containing the amino acid sequence represented by SEQ ID NO: 5 (the amino acid sequence shown by FIGS. 5-7).

A preferred example of the protein having substantially the same amino acid sequence as that represented by SEQ ID NO: 1 is a protein having substantially the same amino acid sequence as that represented by SEQ ID NO: 1 and having substantially the same activity as that of the amino acid sequence represented by SEQ ID NO: 1.

Examples of substantially the same activity include ligand binding activity, signal transduction activity and the like. The term "substantially the same" is used to mean that the natures of their activities are equal to one another. It is thus preferred that though the activity such as ligand binding activity or signal transduction activity be equal (e.g., approximately 0.01 to 100 times, preferably about 0.5 to 20 times, more preferably about 0.5 to twice), quantitative factors such as degrees of these activities and molecular weight of the proteins may differ from each other.

The activities such as ligand binding activity or signal transduction activity may be determined according to a publicly known method, for example, by the method for determining ligands or the screening method which will be later described.

The receptor protein of the present invention which can be used may be a protein comprising (i) an amino acid sequence represented by SEQ ID NO: 1, in which one, two, or more amino acids (preferably 1 to 30 amino acids, more preferably 1 to 10 amino acids, most preferably several (1 or 2) amino acids) are deleted; (ii) an amino acid sequence represented by SEQ ID NO: 1, to which one, two, or more amino acids (preferably 1 to 30 amino acids, more preferably 1 to 10 amino acids, most preferably several (1 or 2) amino acids) are added; (iii) an amino acid sequence represented by SEQ ID NO: 1, in which one, two, or more amino acids (preferably 1 to 30 amino acids, more preferably 1 to 10 amino acids, and most preferably several (1 or 2) amino acids) are substituted by other amino acids; and (iv) a combination of the above amino acid sequences.

The receptor protein of the present invention which can be used may also be a protein comprising (i) an amino acid sequence represented by SEQ ID NO: 5, in which one, two, or more amino acids (preferably 1 to 30 amino acids, more preferably 1 to 10 amino acids, most preferably several (1 or 2) amino acids) are deleted; (ii) an amino acid sequence represented by SEQ ID NO: 5, to which one, two, or more amino acids (preferably 1 to 30 amino acids, more preferably 1 to 10 amino acids, most preferably several (1 or 2) amino acids) are added; (iii) an amino acid sequence represented by SEQ ID NO: 5, in which one, two, or more amino acids (preferably 1 to 30 amino acids, more preferably 1 to 10 amino acids, and most preferably several (1 or 2) amino acids) are substituted by other amino acids; and (iv) a combination of the above amino acid sequences.

The receptor protein of the present invention is designated by the art-recognized way of describing peptides. That is, the left end (amino terminal) is the N-terminal and the right end (carboxyl terminal) is the C-terminal. In the receptor protein of the present invention comprising an amino acid sequence represented by SEQ ID No: 1, the C-terminal is normally carboxyl group (—COOH) or carboxylate (—COO$^-$), but the C-terminal may be an amide (—CONH$_2$) or an ester (—COOR)

Examples of the ester group shown by R include an alkyl group having 1 to 6 carbon atoms such as methyl, ethyl, n-propyl, isopropyl, n-butyl, etc.; a cycloalkyl group having 3 to 8 carbon atoms such as cyclopentyl, cyclohexyl, etc.; an aryl group having 6 to 12 carbon atoms such as phenyl, α-naphthyl, etc.; an aralkyl having 7 to 14 carbon atoms such as a phenyl-C$_{1-2}$ alkyl group, e.g., benzyl, phenethyl, etc.; an α-naphthyl-C$_{1-2}$ alkyl group, e.g., α-naphthylmethyl, etc.; and the like. In addition, pivaloyloxymethyl or the like which is used widely as an ester for oral administration may also be used.

Where the receptor protein of the present invention contains a carboxyl group (or carboxylate) at a position other than the C-terminal, it may be amidated or esterified and such an amide or ester is also included within the receptor protein of the present invention. The ester group may be the same group as that described with respect to the above C-terminal.

Further, the receptor protein of the present invention includes derivatives wherein the amino group of N-terminal methionine residue of the above protein is protected with a protecting group (e.g., an acyl group having 1 to 6 carbon atoms such as formyl group, acetyl group, etc.); those wherein the N-terminal region is cleaved in vivo and the glutamyl group formed is pyroglutaminated; and those wherein a substituent (e.g., —OH, —SH, —COOH, amino group, imidazole group, indole group, guanidino group, etc.) on the side chains of an amino acid in the molecule of the protein is protected with an appropriate protecting group (e.g., an acyl group having 1 to 6 carbon atoms such as an alkanoyl group having 2 to 6 carbon atoms, e.g., formyl group, acetyl group, etc.), or conjugated proteins such as glycoproteins with sugar chains attached thereto.

Specific examples of the receptor protein of the present invention which can be used include a rat-derived receptor protein containing the amino acid sequence represented by SEQ ID NO: 1 and a human-derived receptor protein containing the amino acid sequence represented by SEQ ID NO: 5.

The partial peptide of the receptor protein of the present invention (hereinafter sometimes referred to as the partial peptide) may be any partial peptide, so long as it constitutes a part of the peptide portions of the receptor protein of the present invention described above. Examples of such partial peptide include the site, which is exposed outside cell membranes among the receptor protein molecule of the present invention and retains the receptor binding activity.

Figure 8:
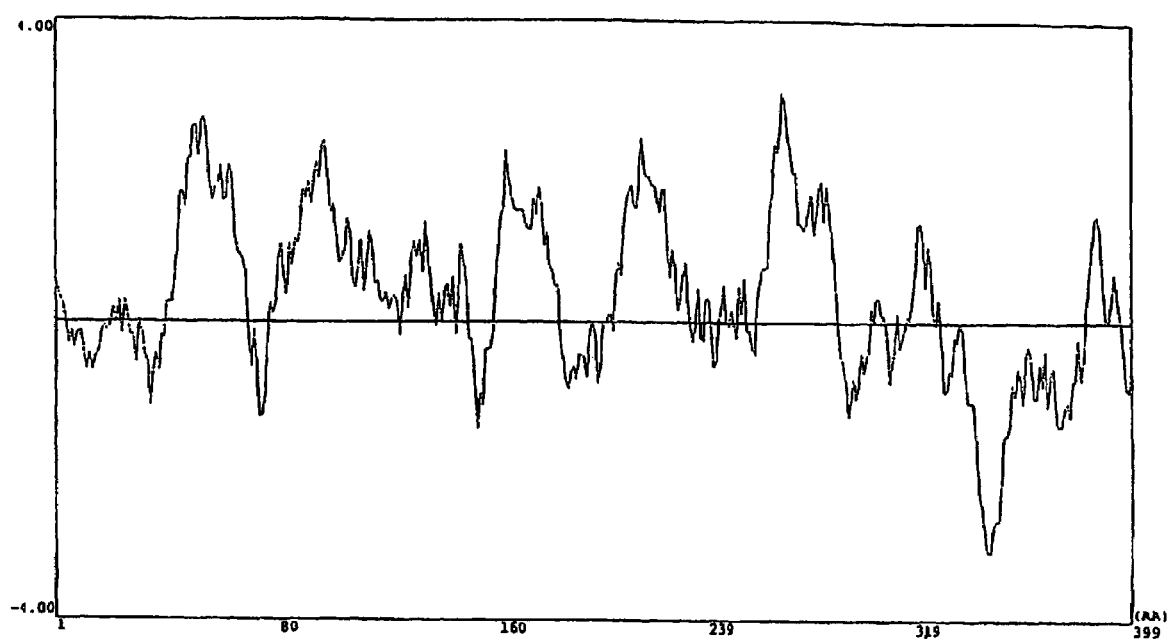
FIG. 8 shows the hydrophobic plotting of the human brain-derived G protein coupled receptor protein hOT7T175 of the present invention prepared based on the amino acid sequence shown in FIGS. 5 through 7.

An example of the partial peptide of the protein containing the amino acid sequence represented by SEQ ID NO: 1 is a peptide containing a region which is analyzed to be an extracellular area (hydrophilic region or site) in a hydrophobic plotting analysis shown by FIG. 4. A further example of the partial peptide of the protein containing the amino acid sequence represented by SEQ ID NO: 5 is a peptide containing a region which is analyzed to be an extracellular area (hydrophilic region or site) in a hydrophobic plotting analysis shown by FIG. 8. A peptide, which partly contains a hydrophobic region or site, may be used as well. Further, a peptide, which independently contains each domain, may also be used although the partial peptide, which contains a 6 plurality of domains at the same time, may also be used.

The number of amino acids in the partial peptide of the present invention is at least 20 or more, preferably 50 or more, more preferably 100 or more, in terms of the constructive amino acid sequence of the receptor protein of the present invention described above.

The substantially the same amino acid sequence refers to an amino acid sequence having at least about 50% homology, preferably at least about 70% homology, more preferably at least about 80% homology, much more preferably at least about 90% homology, most preferably at least about 95% homology.

Herein, the term substantially the same activity has the same definition described above. The "substantially the same activity" can be assayed in the manner described above.

In the partial peptide of the present invention, one, two, or more amino acids (preferably approximately 1 to 10 amino acids, more preferably several (1 or 2) amino acids) may be deleted in the amino acid sequence described above; one, two, or more amino acids (preferably approximately 1 to 20 amino acids, more preferably approximately 1 to 10 amino acids, and most preferably several (1 or 2) amino acids) may be added to the amino acid sequence; or, one, two, or more amino acids (preferably approximately 1 to 10 amino acids, more preferably several amino acids (1 or 2)) may be substituted by other amino acids in the amino acid sequence.

In the partial peptide of the present invention, the C-terminal is normally carboxyl group (—COOH) or carboxylate (—COO$^-$) but the C-terminal may be an amide (—CONH$_2$) or an ester (—COOR), as has been described with the receptor protein of the present invention.

As in the receptor protein of the present invention described above, the partial peptide of the present invention also includes conjugated peptides such as those in which the amino group of the N-terminal methionine residue is protected by a protecting group, those in which the N-terminal residue is cleaved in vivo and the produced Gln is converted into pyroglutamate, those in which substituents on the side chains of amino acids in the molecule are protected by appropriate protecting groups and those to which sugar chains are bound, that is, glycopeptides.

The receptor protein of the present invention or partial peptide thereof may be used in the form of salts with physiologically acceptable bases or acids, preferably in the form of physiologically acceptable acid addition salts thereof. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

The receptor protein of the present invention or salts thereof may be manufactured in accordance with a publicly known method for purification of a receptor protein from human or other mammalian cells or tissues described above. Alternatively, the receptor protein of the present invention or salts thereof may also be manufactured by culturing a transformant containing DNA encoding the receptor protein of the present invention, as will be later described. Furthermore the receptor protein of the present invention or salts thereof may also be manufactured by the methods for synthesizing proteins, which will also be described hereinafter, or by modified methods.

Where the receptor protein or salts thereof are manufactured from human or mammalian tissues or cells, human or mammalian tissues or cells are homogenized, then extracted with an acid or the like, and the extract is isolated and purified by a combination of chromatography techniques such as reverse phase chromatography, ion exchange chromatography, and the like.

To synthesize the receptor protein, partial peptide or its salts or amides of the present invention, commercially available resins that are used for protein synthesis can be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenyl acetamidomethyl resin, polyacrylamide resin, 4-(2',4'-dimethoxyphenyl-hydroxymethyl)phenoxy resin and 4-(2', 4'-dimethoxyphenyl-Fmoc-aminoethyl) phenoxy resin. Using these resins, amino acids in which α-amino groups and functional groups on the side chains are appropriately protected are condensed on the resin in the order of the sequence of the objective protein according to various condensation methods publicly known in the art. At the end of the reaction, the protein is excised from the resin and at the same time, the protecting groups are removed. Then, intramolecular disulfide bond-forming reaction is performed in a highly diluted solution to obtain the objective protein or amides thereof.

For condensation of the protected amino acids described above, a variety of activation reagents for protein synthesis may be used, but carbodiimides are particularly preferably employed. Examples of such carbodiimides include DCC, N,N'-diisopropylcarbodiimide, and N-ethyl-N'-(3-dimethylaminopropyl)carbodiimide. For activation by these reagents, the protected amino acids in combination with a racemization inhibitor (e.g., HOBt, HOOBt) are added directly to the resin, or the protected amino acids are previously activated in the form of symmetric acid anhydrides, HOBt esters or HOOBt esters, followed by adding the thus activated protected amino acids to the resin.

Solvents suitable for use in the activation of the protected amino acids or the condensation with the resin may be selected from solvents that are known to be usable for protein condensation reactions. Examples of such solvents are acid amides such as N,N-dimethylformamide, N,N-dimethylacetamide and N-methylpyrrolidone; halogenated hydrocarbons such as methylene hydrochloride and chloroform; alcohols such as trifluoroethanol; sulfoxides such as dimethylsufoxide; ethers such as pyridine, dioxane and tetrahydrofuran; nitrites such as acetonitrile and propionitrile; esters such as methyl acetate and ethyl acetate; and appropriate mixtures of these solvents. The reaction temperature is appropriately chosen from the range known to be applicable to protein bonding reactions and is usually selected in the range of approximately –20° C. to 50° C. The activated amino acid derivatives are used generally in an excess of 1.5 to 4 times. The condensation is examined using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole to cancel any possible adverse affect on the subsequent reaction.

Examples of the protecting groups used to protect the starting amino groups include Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulphenyl, diphenylphosphinothioyl, and Fmoc.

A carboxyl group can be protected by, e.g., alkyl esterification (in the form of linear, branched or cyclic alkyl esters of the alkyl moiety such as methyl, ethyl, propyl, butyl, t-butyl, cyclopentyl, cyclohexyl, cycloheptyl, cyclooctyl and 2-adamantyl), aralkyl esterification (e.g., benzyl ester, 4-nitrobenzyl ester, 4-methoxybenzyl ester, 4-chlorobenzyl ester and benzhydryl ester), phenacyl esterification, benzyloxycarbonyl hydrazidation, t-butoxycarbonyl hydrazidation and trityl hydrazidation.

The hydroxyl group of serine can be protected through, for example, its esterification or etherification. Examples of groups appropriately used for the esterification include a lower alkanoyl group such as acetyl group, an aroyl group such as benzoyl group, and a group derived from carbonic acid such as benzyloxycarbonyl group and ethoxycarbonyl group. Examples of a group appropriately used for the etherification include benzyl group, tetrahydropyranyl group and t-butyl group.

Examples of groups for protecting the phenolic hydroxyl group of tyrosine include Bzl, $Cl_2$-Bzl, 2-nitrobenzyl, Br-Z and t-butyl.

Examples of groups used to protect the imidazole moiety of histidine include Tos, 4-methoxy-2,3,6-trimethylbenzenesulfonyl, DNP, benzyloxymethyl, Bum, Boc, Trt and Fmoc.

Examples of the activated carboxyl groups in the starting amino acids include the corresponding acid anhydrides, azides, activated esters (esters with alcohols (e.g. pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt). As the activated amino acids in which the amino groups are activated in the starting material, the corresponding phosphoric amides are employed.

To eliminate (split off) the protecting groups, there are used catalytic reduction under hydrogen gas flow in the presence of a catalyst such as Pd-black or Pd-carbon; an acid treatment with anhydrous hydrogen fluoride, methanesulfonic acid, trifluoromethanesulfonic acid or trifluoroacetic acid, or a mixture solution of these acids; a treatment with a base such as diisopropylethylamine, triethylamine, piperidine or piperazine; and reduction with sodium in liquid ammonia. The elimination reaction of the protecting group by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol or 1,2-ethanedithiol. Furthermore, 2,4-dinitrophenyl group known as the protecting group for the imidazole of histidine is removed by a treatment with thiophenol. Formyl group used as the protecting group of the indole of tryptophan is eliminated by the aforesaid acid treatment in the presence of 1,2-ethanedithiol or 1,4-butanedithiol, as well as by a treatment with an alkali such as a dilute sodium hydroxide solution and dilute ammonia.

Protection of functional groups that should not be involved in the reaction of the starting materials, protecting groups, elimination of the protecting groups and activation of functional groups involved in the reaction may be appropriately selected from publicly known groups and publicly known means.

In another method for obtaining amidated proteins, for example, the α-carboxyl group of the carboxy terminal amino acid is first protected by amidation; the peptide (protein) chain is then extended from the amino group side to a desired length. Thereafter, a protein in which only the protecting group of the N-terminal α-amino group has been eliminated from the peptide and a protein in which only the protecting group of the C-terminal carboxyl group has been eliminated are manufactured. The two proteins are condensed in a mixture of the solvents described above. The details of the condensation reaction are the same as described above. After the protected protein obtained by the condensation is purified, all the protecting groups are eliminated by the method described above to give the desired crude protein. This crude protein is purified by various known purification means. Lyophilization of the major fraction gives the amide of the desired protein.

To prepare the esterified protein, for example, the α-carboxyl group of the carboxy terminal amino acid is condensed with a desired alcohol to prepare the amino acid ester, which is followed by procedure similar to the preparation of the amidated protein above to give the desired esterified protein.

The partial peptide of the receptor protein of the present invention can be manufactured by publicly known methods for peptide synthesis, or by cleaving the receptor protein of the present invention with an appropriate peptidase. For the methods for peptide synthesis, for example, either solid phase synthesis or liquid phase synthesis may be used. That is, the partial peptide or amino acids that can construct the receptor protein of the present invention are condensed with the remaining part of the receptor protein of the present invention. Where the product contains protecting groups, these protecting groups are removed to give the desired peptide. Publicly known methods for condensation and elimination of the protecting groups are described in 1)-5) below.

1) M. Bodanszky & M. A. Ondetti: Peptide Synthesis, Interscience Publishers, New York (1966)

2) Schroeder & Luebke: The Peptide, Academic Press, New York (1965)

3) Nobuo Izumiya, et al.: *Peptide Gosei-no-Kiso to Jikken* (Basics and experiments of peptide synthesis), published by Maruzen Co. (1975)

4) Haruaki Yajima & Shunpei Sakakibara: *Seikagaku Jikken Koza* (Biochemical Experiment) 1, *Tanpakushitsu no Kagaku* (Chemistry of Proteins) IV, 205 (1977)

5) Haruaki Yajima ed.: *Zoku Iyakuhin no Kaihatsu* (A sequel to Development of Pharmaceuticals), Vol. 14, Peptide Synthesis, published by Hirokawa Shoten After completion of the reaction, the product may be purified and isolated by a combination of conventional purification methods such as solvent extraction, distillation, column chromatography, liquid chromatography and recrystallization to give the partial peptide of the present invention. When the partial peptide obtained by the above methods is in a free form, the peptide can be converted into an appropriate salt by a publicly known method; when the protein is obtained in a salt form, it can be converted into a free form by a publicly known method.

The polynucleotide encoding the receptor protein of the present invention may be any polynucleotide so long as it contains the base sequence (DNA or RNA, preferably DNA) encoding the receptor protein of the present invention described above. Such a polynucleotide may be DNA and RNA including mRNA that codes for the receptor protein of the present invention. The polynucleotide may be either double-stranded or single-stranded. When the polynucleotide is double-stranded, it may be double-stranded DNA or a DNA:RNA hybrid. When the polynucleotide is single-stranded, it may be a sense strand (i.e., coding strand) or an antisense strand (i.e., non-coding strand).

Using the polynucleotide encoding the receptor protein of the present invention, mRNA of the receptor protein of the present invention can be quantified by, for example, the method published in separate volume of *Jikken Igaku* (Experimental Medical Science), 15(7), "New PCR and its application" (1997) or by modification of the method.

The DNA encoding the receptor protein of the present invention may be any of genomic DNA, genomic DNA library, cDNA derived from the cells and tissues described above, cDNA library derived from the cells and tissues described above and synthetic DNA. The vector to be used for the library may be any of bacteriophage, plasmid, cosmid and phagemid. The DNA may be directly amplified by reverse transcriptase polymerase chain reaction (hereinafter abbreviated as RT-RCR) using the total RNA or mRNA fraction prepared from the cells and tissues described above.

Specifically, the DNA encoding the partial peptide of the receptor protein of the present invention may be any DNA so long as it has, for example, DNA having the amino acid sequence represented by SEQ ID NO: 2 or SEQ ID NO: 6 or it has a base sequence hybridizable to the base sequence represented by SEQ ID NO: 2 or SEQ ID NO: 6 under high stringent conditions and encodes a protein having substantially the same activities (i.e., ligand binding activity, signal transduction activity and the like) as those of the receptor protein of the present invention.

Examples of the DNA that is hybridizable to the base sequence represented by SEQ ID NO: 2 or SEQ ID NO: 6 include DNA having at least about 70% homology, preferably at least about 80% homology, more preferably at least about 90% homology, most preferably at least about 95% homology, to the base sequence represented by SEQ ID NO: 2 or SEQ ID NO: 6.

The hybridization can be carried out by publicly known methods or by a modification thereof, for example, according to the method described in Molecular Cloning, 2nd Ed.; J. Sambrook et al., Cold Spring Harbor Lab. Press, (1989). A commercially available library may also be used according to the instructions of the attached manufacturer's protocol. The hybridization can be carried out preferably under high stringent conditions.

The high stringent conditions used herein are, for example, those in a sodium concentration at about 19 mM to about 40 mM, preferably about 19 mM to about 20 mM and a temperature at about 50° C. to about 70° C., preferably about 60° C. to about 65° C. In particular, hybridization conditions in a sodium concentration at about 19 mM and a temperature at about 65° C. are most preferred.

More specifically, for the DNA encoding the protein having the amino acid sequence represented by SEQ ID NO: 1, there may be employed DNA having the base sequence represented by SEQ ID NO: 2 and, DNA having the base sequence represented by SEQ ID NO: 6 may be used for the DNA encoding the protein having the amino acid sequence represented by SEQ ID NO: 5.

The polynucleotide comprising a part of the base sequence of DNA encoding the receptor protein of the present invention or a part of the base sequence complementary to the DNA is intended to include not only DNA encoding the partial peptide of the present invention described below but also RNA.

According to the present invention, antisense polynucleotides (nucleic acids) that can inhibit replication or expression of the receptor protein gene of the present invention can be designed and synthesized based on the cloned or determined base sequence information of the DNA encoding the receptor protein. Such polynucleotides (nucleic acids) can hybridize to the RNA of the protein gene and inhibit RNA synthesis or the function of RNA, or can regulate/control the expression of the receptor protein gene via the interaction with RNAs associated with the receptor protein. Polynucleotides complementary to the specified sequences of RNA associated with the receptor protein and polynucleotides that can specifically hybridize to RNA associated with the receptor protein are useful for regulating and controlling the expression of the receptor protein gene in vivo and in vitro. These polynucleotides are also useful for the treatment and diagnosis of diseases. The term "correspond" is used to refer to homologous or complementary to a specific sequence of nucleotides, base sequences or nucleic acids including the gene. As between nucleotides, base sequences or nucleic acids and peptides (proteins), the term "corresponding" usually refers to amino acids of a peptide (protein) that is instructed to be derived from the sequence of nucleotides (nucleic acids) or its complements. The 5' end hairpin loop, 5' end 6-base-pair repeats, 5' end untranslated region, polypeptide translation initiation codon, protein coding region, ORF translation initiation codon, 3' untranslated region, 3' end palindrome region, and 3' end hairpin loop of the receptor protein gene may be selected as preferred target regions, though any region may be a target within the receptor protein genes.

The relationship between the targeted nucleic acids and the polynucleotides complementary to at least a portion of the target, specifically the relationship between the target and the polynucleotides hybridizable to the target, is denoted to be "antisense". The antisense polynucleotides may be polydeoxynucleotides containing 2-deoxy-D-ribose, polydeoxynucleotides containing D-ribose, any other type of polynucleotides which are N-glycosides of a purine or pyrimidine base, or other polymers containing non-nucleotide backbones (e.g., protein nucleic acids and synthetic sequence-specific nucleic acid polymers commercially available) or other polymers containing nonstandard linkages (provided that the polymers contain nucleotides with such a configuration that allows base pairing or base stacking, as is found in DNA and RNA). The antisense polynucleotides may be double-stranded DNA, single-stranded DNA, single-stranded RNA or a DNA:RNA hybrid, and further includes unmodified polynucleotides (or unmodified oligonucleotides), those with publicly known types of modifications, for example, those with labels known in the art, those with caps, methylated polynucleotides, those with substitution of one or more of naturally occurring nucleotides with their analogue, those with intramolecular modifications of nucleotides such as those with uncharged linkages (e.g., methyl phosphonates, phosphotriesters, phosphoramidates, carbamates, etc.) and those with charged linkages or sulfur-containing linkages (e.g., phosphorothioates, phosphorodithioates, etc.), those having side chain groups such as proteins (including nucleases, nuclease inhibitors, toxins, antibodies, signal peptides, poly-L-lysine, etc.) and saccharides (e.g., monosaccharides, etc.), those with intercalators (e.g., acridine, psoralen, etc.), those containing chelators (e.g., metals, radioactive metals, boron, oxidative metals, etc.) and those containing alkylating agents, those with modified linkages (e.g., a anomeric nucleic acids, etc.). Herein the terms "nucleoside", "nucleotide" and "nucleic acid" are used to refer to moieties that contain not only the purine and pyrimidine bases, but also other heterocyclic bases, which have been modified. Such modifications include methylated purines and pyrimidines, acylated purines and pyrimidines and other heterocyclic rings. Modified nucleosides or nucleotides also include modifications on the sugar moiety, for example, wherein one or more hydroxyl groups may optionally be replaced with a halogen, aliphatic groups, or may be converted into the corresponding functional groups such as ethers, amines, or the like.

The antisense polynucleotide (nucleic acid) of the present invention is RNA, DNA or a modified nucleic acid (RNA, DNA). Specific examples of the modified nucleic acid are, but not limited to, sulfurized and thiophosphate derivatives of nucleic acids and those resistant to degradation of polynucleoside or oligonucleoside amides. The antisense nucleic acids of the present invention can be modified preferably based on the following design, that is, by increasing the intracellular stability of the antisense nucleic acid, increasing the cellular permeability of the antisense nucleic acid, increasing the affinity of the nucleic acid to the target sense strand to a higher level, or minimizing the toxicity, if any, of the antisense nucleic acid.

Many such modifications are known in the art, as disclosed in J. Kawakami et al., Pharm. Tech. Japan, Vol. 8, pp. 247, 1992; Vol. 8, pp. 395, 1992; S. T. Crooke et al. ed., Antisense Research and Applications, CRC Press, 1993; etc.

The antisense nucleic acid of the present invention may contain altered or modified sugars, bases or linkages. The antisense nucleic acid may also be provided in a specialized form such as liposomes, microspheres or may be applied to gene therapy or may be provided in combination with attached moieties. Such attached moieties include polycations such as polylysine that act as charge neutralizers of the phosphate backbone, or hydrophobic moieties such as lipids (e.g., phospholipids, cholesterols, etc.) that enhance the interaction with cell membranes or increase uptake of the nucleic acid. Preferred examples of the lipids to be attached are cholesterols or derivatives thereof (e.g., cholesteryl chloroformate, cholic acid, etc.). These moieties may be attached at the 3' or 5' ends of the nucleic acid and may be also attached through a base, sugar, or intramolecular nucleoside linkage. Other moieties may be capping groups specifically placed at the 3' or 5' ends of the nucleic acid to prevent degradation by nuclease such as exonuclease, RNase, etc. Such capping groups include, but are not limited to, hydroxyl protecting groups known in the art, including glycols such as polyethylene glycol, tetraethylene glycol and the like.

The inhibitory activity of the antisense nucleic acid can be examined using the transformant of the present invention, the gene expression system of the present invention in vitro and in vivo, or the translation system of the receptor protein of the present invention in vitro and in vivo. The nucleic acid can be applied to cells by a variety of publicly known methods.

The DNA encoding the partial peptide of the present invention may be any DNA so long as it contains the base sequence encoding the partial peptide of the present invention described above. The DNA may also be any of genomic DNA, genomic DNA library, cDNA derived from the cells and tissues described above, cDNA library derived from the cells and tissues described above and synthetic DNA. The vector to be used for the library may be any of bacteriophage, plasmid, cosmid and phagemid. The DNA may be directly amplified by reverse transcriptase polymerase chain reaction (hereinafter simply referred to as RT-RCR) using mRNA fraction prepared from the cells and tissues described above.

Specific examples of the DNA encoding the partial peptide of the present invention include (1) DNA that has a part of the base sequence of the DNA containing the base sequence represented by SEQ ID NO: 2 or SEQ ID NO: 6 and (2) DNA having a base sequence hybridizable to the base sequence represented by SEQ ID NO: 2 or SEQ ID NO: 6 under high stringent conditions and containing a part of the base sequence of the DNA encoding a receptor protein having substantially the same activities (i.e., ligand binding activity, signal transduction activity and the like) as those of the receptor protein of the present invention.

Examples of the DNA that is hybridizable to the base sequence represented by SEQ ID NO: 2 or SEQ ID NO: 6 include DNA containing the base sequence having at least about 70% homology, preferably at least about 80% homology, more preferably at least about 90% homology, most preferably at least about 95% homology, to the base sequence represented by SEQ ID NO: 2 or SEQ ID NO: 6.

For cloning of the DNA that completely encodes the receptor protein or its partial peptide of the present invention (hereinafter sometimes referred to as the receptor protein of the present invention), the DNA may be either amplified by PCR using synthetic DNA primers containing a part of the base sequence of the receptor protein of the present invention, or the DNA inserted into an appropriate vector can be selected by hybridization with a labeled DNA fragment or synthetic DNA that encodes a part or entire region of the receptor protein of the present invention. The hybridization can be carried out, for example, according to the method described in Molecular Cloning, 2nd (J. Sambrook et al., Cold Spring Harbor Lab. Press, 1989). The hybridization may also be performed using commercially available library in accordance with the protocol described in the attached instructions.

Conversion of the base sequence of DNA can be carried out according to publicly known methods such as the Gupped duplex method or the Kunkel method or its modification by using a publicly known kit available as Mutan™-G or Mutan™-K (both manufactured by Takara Shuzo Co., Ltd., trademark).

The cloned DNA encoding the receptor protein of the present invention can be used as it is, depending upon purpose or, if desired, after digestion with a restriction enzyme or after addition of a linker thereto. The DNA may contain ATG as a translation initiation codon at the 5' end thereof and TAA, TGA or TAG as a translation termination codon at the 3' end thereof. These translation initiation and termination codons may also be added by using an appropriate synthetic DNA adapter.

The expression vector of the receptor protein of the present invention can be manufactured, for example, by (a) excising the desired DNA fragment from the DNA encoding the receptor protein of the present invention, (b) followed by ligation of the DNA fragment with an appropriate expression vector downstream a promoter in the vector.

Examples of the vector which can be used include plasmids derived form *E. coli* (e.g., pBR322, pBR325, pUC12, pUC13), plasmids derived from *Bacillus subtilis* (e.g., pUB110, pTP5, pC194), plasmids derived from yeast (e.g., pSH19, pSH15), bacteriophages such as λ phage, etc., animal viruses such as retrovirus, vaccinia virus, baculovirus, etc. as well as pA1-11, pXT1, pRc/CMV, pRc/RSV, pcDNAI/Neo, etc.

The promoter used in the present invention may be any promoter if it matches well with a host to be used for gene expression. In the case of using animal cells as the host, examples of the promoter include SRα promoter, SV40 promoter, LTR promoter, CMV promoter, HSV-TK promoter, etc. Among them, CMV promoter or SRα promoter is preferably used.

Where the host is bacteria of the genus *Escherichia*, preferred examples of the promoter include trp promoter, lac promoter, recA promoter, APL promoter, lpp promoter, etc. In the case of using bacteria of the genus *Bacillus* as the host, preferred example of the promoter are SPO1 promoter, SPO2 promoter and penP promoter. In the case of using yeast as the host, preferred examples of the promoter are PHO5 promoter, PGK promoter, GAP promoter and ADH promoter. In the case of using insect cells as the host, preferred examples of the promoter include polyhedrin prompter and P10 promoter.

In addition to the foregoing examples, the expression vector may further optionally contain an enhancer, a splicing signal, a poly A addition signal, a selection marker, SV40 replication origin (hereinafter sometimes abbreviated as SV40ori) etc. Examples of the selection marker include dihydrofolate reductase (hereinafter sometimes abbreviated as dhfr) gene [methotrexate (MTX) resistance], ampicillin resistant gene (hereinafter sometimes abbreviated as Amp$^r$), neomycin resistant gene (hereinafter sometimes abbreviated as Neo, G418 resistance), etc. In particular, when CHO (dhfr$^-$) cell is used together with dhfr gene as the selection marker, selection can also be made by using a thymidine free medium.

If necessary and desired, a signal sequence that matches with a host is added to the N-terminus of the receptor protein of the present invention. Examples of the signal sequence that can be used are Pho A signal sequence, OmpA signal sequence, etc. in the case of using bacteria of the genus *Escherichia* as the host; α-amylase signal sequence, subtilisin signal sequence, etc. in the case of using bacteria of the genus *Bacillus* as the host; MF α signal sequence, SUC2 signal sequence, etc. in the case of using yeast as the host; and insulin signal sequence, α-interferon signal sequence, antibody molecule signal sequence, etc. in the case of using animal cells as the host, respectively.

Using the vector comprising the DNA encoding the receptor protein of the present invention thus constructed, transformants can be manufactured.

Examples of the host, which may be employed, are bacteria belonging to the genus *Escherichia*, bacteria belonging to the genus *Bacillus*, yeast, insect cells, insects and animal cells, etc.

Specific examples of bacteria belonging to the genus *Escherichia* include *Escherichia coli* K12 DH1 (Proc. Natl.

Acad. Sci. U.S.A., 60, 160 (1968)), JM103 (Nucleic Acids Research, 9, 309 (1981)), JA221 (Journal of Molecular Biology, 120, 517 (1978)), HB101 (Journal of Molecular Biology, 41, 459 (1969)), C600 (Genetics, 39, 440 (1954)), etc.

Examples of bacteria belonging to the genus Bacillus include Bacillus subtilis MI114 (Gene, 24, 255 (1983)), 207-21 (Journal of Biochemistry, 95, 87 (1984)), etc.

Examples of yeast include Saccharomyces cereviseae AH22, AH22R$^-$, NA87-11A, DKD-5D, 20B-12, Schizosaccharomyces pombe NCYC1913, NCYC2036, Pichia pastoris, etc.

Examples of insect cells include, for the virus AcNPV, Spodoptera frugiperda cell (Sf cell), MG1 cell derived from mid-intestine of Trichoplusia ni, High Five™ cell derived from egg of Trichoplusia ni, cells derived from Mamestra brassicae, cells derived from Estigmena acrea, etc.; and for the virus BmNPV, Bombyx mori N cell (BmN cell), etc. Examples of the Sf cell which can be used are Sf9 cell (ATCC CRL1711) and Sf21 cell (both cells are described in Vaughn, J. L. et al. In Vivo, 13, 213-217 (1977).

As the insect, for example, a larva of Bombyx mori can be used (Maeda et al., Nature, 315, 592 (1985)).

Examples of animal cells include monkey cell COS-7, Vero, Chinese hamster cell CHO (hereinafter referred to as CHO cell), dhfr gene deficient Chinese hamster cell CHO (hereinafter simply referred to as CHO(dhfr$^-$) cell), mouse L cell, mouse AtT-20, mouse myeloma cell, rat GH 3, human FL cell, etc.

Bacteria belonging to the genus Escherichia can be transformed, for example, according to the method described in Proc. Natl. Acad. Sci. U.S.A., 69, 2110 (1972) or Gene, 17, 107 (1982).

Bacteria belonging to the genus Bacillus can be transformed, for example, according to the method described in Molecular & General Genetics, 168, 111 (1979).

Yeast can be transformed, for example, according to the method described in Methods in Enzymology, 194, 182-187 (1991) or Proc. Natl. Acad. Sci. U.S.A., 75, 1929 (1978).

Insect cells or insects can be transformed, for example, according to the method described in Bio/Technology, 6, 47-55 (1988).

Animal cells can be transformed, for example, according to the method described in Saibo Kogaku (Cell Engineering), extra issue 8, Shin Saibo Kogaku Jikken Protocol (New Cell Engineering Experimental Protocol), 263-267 (1995), published by Shujunsha, or Virology, 52, 456 (1973).

Thus, the transformant transformed with the expression vector containing the DNA encoding the receptor protein or partial peptide of the present invention can be obtained.

Where the host is bacteria belonging to the genus Escherichia or the genus Bacillus, the transformant can be appropriately incubated in a liquid medium which contains materials required for growth of the transformant such as carbon sources, nitrogen sources, inorganic materials, etc. Examples of the carbon sources include glucose, dextrin, soluble starch, sucrose, etc. Examples of the nitrogen sources include inorganic or organic materials such as ammonium salts, nitrate salts, corn steep liquor, peptone, casein, meat extract, soybean cake, potato extract, etc. Examples of the inorganic materials are calcium chloride, sodium dihydrogenphosphate, magnesium chloride, etc. In addition, yeast, vitamins, growth promoting factors etc. may also be added to the medium. Preferably, pH of the medium is adjusted to about 5 to about 8.

A preferred example of the medium for incubation of the bacteria belonging to the genus Escherichia is M9 medium supplemented with glucose and Casamino acids (Miller, Journal of Experiments in Molecular Genetics, 431-433, Cold Spring Harbor Laboratory, New York, 1972). If necessary and desired, a chemical such as 3β-indolylacrylic acid can be added to the medium thereby to activate the promoter efficiently.

Where the bacteria belonging to the genus Escherichia are used as the host, the transformant is usually cultivated at about 15° C. to about 43° C. for about 3 hours to about 24 hours. If necessary and desired, the culture may be aerated or agitated.

Where the bacteria belonging to the genus Bacillus are used as the host, the transformant is cultivated generally at about 30° C. to about 40° C. for about 6 hours to about 24 hours. If necessary and desired, the culture can be aerated or agitated.

Where yeast is used as the host, the transformant is cultivated in, for example, Burkholder's minimal medium (Bostian, K. L. et al., Proc. Natl. Acad. Sci. U.S.A., 77, 4505 (1980)) or in SD medium supplemented with 0.5% Casamino acids (Bitter, G. A. et al., Proc. Natl. Acad. Sci. U.S.A., 81, 5330 (1984)). Preferably, pH of the medium is adjusted to about 5 to about 8. In general, the transformant is cultivated at about 20° C. to about 35° C. for about 24 hours to about 72 hours. If necessary and desired, the culture can be aerated or agitated.

Where insect cells or insects are used as the host, the transformant is cultivated in, for example, Grace's Insect Medium (Grace, T. C. C., Nature, 195, 788 (1962)) to which an appropriate additive such as immobilized 10% bovine serum is added. Preferably, pH of the medium is adjusted to about 6.2 to about 6.4. Normally, the transformant is cultivated at about 27° C. for about 3 days to about 5 days and, if necessary and desired, the culture can be aerated or agitated.

Where animal cells are employed as the host, the transformant is cultivated in, for example, MEM medium containing about 5% to about 20% fetal bovine serum (Science, 122, 501 (1952)), DMEM medium (Virology, 8, 396 (1959)), RPMI 1640 medium (The Journal of the American Medical Association, 199, 519 (1967)), 199 medium (Proceeding of the Society for the Biological Medicine, 73, 1 (1950)), etc. Preferably, pH of the medium is adjusted to about 6 to about 8. The transformant is usually cultivated at about 30° C. to about 40° C. for about 15 hours to about 60 hours and, if necessary and desired, the culture can be aerated or agitated.

As described above, the receptor protein or its partial peptide of the present invention can be produced in the cell membrane of the transformant.

The receptor protein or partial peptide of the present invention can be separated and purified from the culture described above by the following procedures.

When the receptor protein or its partial peptide of the present invention is extracted from the culture or cells, after cultivation, the transformant or cell is collected by a publicly known method and suspended in a appropriate buffer. The transformant or cell is then disrupted by publicly known methods such as ultrasonication, a treatment with lysozyme and/or freeze-thaw cycling, followed by centrifugation, filtration, etc. Thus, the crude extract of the receptor protein or its partial peptide of the present invention can be obtained. The buffer used for the procedures may contain a protein modifier such as urea or guanidine hydrochloride, or a surfactant such as Triton X-100™, etc. When the receptor protein or its partial peptide of the present invention is secreted in the culture broth, after completion of the cultivation the supernatant can be separated from the transformant or cell to collect the supernatant by a publicly known method.

The supernatant or the receptor protein or its partial peptide of the present invention contained in the extract thus obtained can be purified by appropriately combining the publicly known methods for separation and purification. Such publicly known methods for separation and purification include a method utilizing difference in solubility such as salting out, solvent precipitation, etc.; a method mainly utilizing difference in molecular weight such as dialysis, ultrafiltration, gel filtration, SDS-polyacrylamide gel electrophoresis, etc.; a method utilizing difference in electric charge such as ion exchange chromatography, etc.; a method utilizing difference in specific affinity such as affinity chromatography, etc.; a method utilizing difference in hydrophobicity such as reverse phase high performance liquid chromatography, etc.; a method utilizing difference in isoelectric point such as isoelectrofocusing electrophoresis; and the like.

When the receptor protein or its partial peptide of the present invention thus obtained is in a free form, it can be converted into the salt by publicly known methods or modifications thereof. On the other hand, when the receptor protein is obtained in the form of a salt, it can be converted into the free form or in the form of a different salt by publicly known methods or modifications thereof.

The receptor protein or its partial peptide of the present invention produced by the recombinant can be treated, prior to or after the purification, with an appropriate protein modifying enzyme so that the protein or partial peptide can be appropriately modified to partially remove a polypeptide. Examples of the protein-modifying enzyme include trypsin, chymotrypsin, arginyl endopeptidase, protein kinase, glycosidase and the like.

The activity of the thus produced receptor protein of the present invention or salts thereof, the partial peptide or its esters, amides or salts of the present invention can be determined by a binding test to a labeled ligand and by an enzyme immunoassay using a specific antibody.

Antibodies to the receptor protein or its salts, the partial peptide or its esters, amides or salts according to the present invention (hereinafter sometimes collectively referred to as the receptor protein or the like of the present invention) or the ligand peptide of the present invention (which will be later described) may be any of polyclonal and monoclonal antibodies, so long as they can recognize the receptor protein or the like of the present invention or the ligand peptide of the present invention.

The antibody to the receptor protein or the like of the present invention or to the ligand peptide of the present invention can be manufactured by publicly known methods for manufacturing antibodies or antisera, using as an antigen the receptor protein or the like of the present invention or the ligand peptide of the present invention.

[Preparation of Monoclonal Antibody]

(a) Preparation of Monoclonal Antibody-Producing Cells

The receptor protein or the like of the present invention or the ligand peptide of the present invention is administered to a mammal, either solely or together with carriers or diluents to the site that can produce the antibody by the administration. In order to potentiate the antibody productivity upon the administration, complete Freund's adjuvant or incomplete Freund's adjuvant may be administered. The administration is effected usually once every 2 to 6 weeks and approximately 2 to 10 times in total. The mammals to be used include monkey, rabbit, dog, guinea pig, mouse, rat, sheep, goat and the like, with mouse and rat being preferred.

In the preparation of the monoclonal antibody-producing cells, an animal wherein the antibody titer is noted is selected from warm-blooded animals immunized with antigens, e.g., mice, then spleen or lymph node is collected after two to five days from the final immunization and the antibody-producing cells contained therein are fused with myeloma cells to give monoclonal antibody-producing hybridomas. The antibody titer in antisera may be determined, for example, by reacting the labeled receptor protein or the like of the present invention or the ligand peptide of the present invention, which will be described later, with the antiserum followed by measuring the binding activity of the labeling agent bound to the antibody. The fusion may be carried out, for example, according to the method for Koehler and Milstein (Nature, 256, 495, 1975). Examples of the fusion accelerator are polyethylene glycol (PEG), Sendai virus, etc. and PEG is preferably used.

Examples of myeloma cells include NS-1, P3U1 and SP2/0, with P3U1 being preferred. The ratio of the number of the antibody-producing cells (spleen cells) to the number of myeloma cells to be used is preferably about 1:1 to about 20:1 and PEG (preferably PEG 1000 to PEG 6000) is added in a concentration of about 10% to about 80%. The cell fusion can be efficiently carried out by incubating both cells at about 20° C. to about 40° C., preferably about 30° C. to about 37° C. for about 1 minute to about 10 minutes.

Various methods can be used for screening of a monoclonal antibody-producing hybridoma. Examples of such methods include a method which comprises adding the supernatant of hybridoma to a solid phase (e.g., microplate) adsorbed with the receptor protein or the like of the present invention or the ligand peptide of the present invention as antigen directly or together with a carrier, adding an anti-immunoglobulin antibody (where mouse cells are used for the cell fusion, anti-mouse immunoglobulin antibody is used) labeled with a radioactive substance or an enzyme or Protein A and detecting the monoclonal antibody bound to the solid phase, and a method which comprises adding the supernatant of hybridoma to a solid phase adsorbed with an anti-immunoglobulin antibody or Protein A, adding the receptor protein or the like of the present invention or the ligand peptide of the present invention labeled with a radioactive substance or an enzyme and detecting the monoclonal antibody bound to the solid phase.

The monoclonal antibody can be selected according to publicly known methods or their modifications. In general, the selection can be effected in a medium for animal cells supplemented with HAT (hypoxanthine, aminopterin and thymidine). Any selection and growth medium can be employed as far as the hybridoma can grow therein. For example, RPMI 1640 medium containing 1% to 20%, preferably 10% to 20% fetal bovine serum, GIT medium (Wako Pure chemical Industries, Ltd.) containing 1% to 10% fetal bovine serum, a serum free medium for cultivation of a hybridoma (SFM-101, Nissui Seiyaku Co., Ltd.) and the like can be used for the selection and growth medium. The cultivation is carried out generally at 20° C. to 40° C., preferably 37° C., for about 5 days to about 3 weeks, preferably 1 to 2 weeks, normally in 5% $CO_2$. The antibody titer of the culture supernatant of a hybridoma can be determined as in the determination of antibody titer in antisera described above.

(b) Purification of Monoclonal Antibody

Separation and purification of a monoclonal antibody can be carried out according the same manner as applied to conventional separation and purification for polyclonal antibodies, such as separation and purification of immunoglobulins (for example, salting-out, alcohol precipitation, isoelectric point precipitation, electrophoresis, adsorption and desorption with ion exchangers (e.g., DEAE), ultracentrifugation, gel filtration, or a specific purification method which comprises collecting only an antibody with an activated adsorbent such as an antigen-binding solid phase, Protein A or Protein G and dissociating the binding to obtain the antibody.

[Preparation of Polyclonal Antibody]

The polyclonal antibody of the present invention can be manufactured by publicly known methods or modifications thereof. For example, a complex of immunogen (antigen of the receptor protein or the like) and a carrier protein is formed and a mammal is immunized with the complex in a manner similar to the method described above for the manufacture of monoclonal antibody. The product containing the antibody to the receptor protein or the like of the present invention or the ligand peptide of the present invention is collected from the immunized animal followed by separation and purification of the antibody.

In the complex of immunogen and carrier protein for immunizing mammals, the type of carrier protein and the mixing ratio of carrier to hapten may be any type and in any ratio, as long as the antibody is efficiently produced to the hapten immunized by crosslinking to the carrier. For example, bovine serum albumin, bovine thyroglobulin or keyhole limpet hemocyanin is coupled to hapten in a carrier-to-hapten weight ratio of approximately 0.1 to 20, preferably 1 to 5.

A variety of condensation agents can be used for the coupling of carrier to hapten. Glutaraldehyde, carbodiimide, maleimide activated ester and activated ester reagents containing thiol group or dithiopyridyl group are used for the coupling.

The condensation product is administered to warm-blooded animals either solely or together with carriers or diluents to the site that can produce the antibody by the administration. In order to potentiate the antibody productivity upon the administration, complete Freund's adjuvant or incomplete Freund's adjuvant may be administered. The administration is usually carried out once every 2 to 6 weeks and 3 to 10 times in total.

The polyclonal antibody can be collected from the blood, ascites, etc., preferably from the blood of mammals immunized by the method described above.

The polyclonal antibody titer in antiserum can be determined by the same procedure as in the serum antibody titer described above. The polyclonal antibody can be separated and purified according to the same method for separation and purification of immunoglobulin as used for the monoclonal antibody described above.

The receptor protein of the present invention or salts thereof, partial peptide or esters, amides or salts thereof and the DNA coding therefore can be used: (1) for determination of ligand (agonist) to the receptor protein of the present invention or salts thereof, (2) as an agent for the prevention and/or treatment of disease associated with dysfunction of the receptor protein of the present invention, (3) as a genetic diagnostic agent, (4) for quantification of ligand to the receptor protein of the present invention, (5) for screening of a compound (agonist, antagonist, etc.) that alters the binding property between the receptor protein of the present invention and a ligand, (6) as the agent for the prevention and/or treatment of various diseases, comprising a compound (agonist, antagonist, etc.) that alters the binding property between the receptor protein of the present invention and a ligand, (7) for the quantification of the receptor protein or the like of the present invention, (8) for the neutralization by antibodies to the receptor protein or the like of the present invention and (9) for preparation of non-human animal bearing the DNA encoding the receptor protein or the like of the present invention.

In particular, a compound (e.g., agonist, antagonist, etc.) that alters the binding property between a ligand and the receptor protein of the present invention specific to human or other mammals can be screened, using the ligand-receptor binding assay system later described by applying thereto the expression system of the recombinant receptor protein of the present invention. The agonist or antagonist can be used as a prophylactic/therapeutic agent for various diseases, which will be described later.

Hereinafter, the receptor protein or the like of the present invention, DNA encoding the receptor protein or the like of the present invention (hereinafter sometimes collectively referred to as the DNA of the present invention) and antibodies to the receptor protein or the like of the present invention (hereinafter sometimes referred to as the antibody of the present invention) are specifically described with their use.

(1) Determination of a Ligand (Agonist) to the Receptor Protein of the Present Invention The receptor protein or the like of the present invention is useful as a reagent for searching and determining a ligand (agonist) to the receptor protein of the present invention and salts thereof.

That is, the present invention provides a method for determining a ligand to the receptor protein of the present invention or salts thereof, which comprises bringing the receptor protein of the present invention or salts thereof in contact with a test compound.

Examples of compounds to be tested include publicly known ligands (e.g., angiotensin, bombesin, canavinoid, cholecystokinin, glutamine, serotonin, melatonin, neuropeptide Y; opioid, purines, vasopressin, oxytocin, PACAP, secretin, glucagon, calcitonin, adrenomedulin, somatostatin, GHRH, CRF, ACTH, GRP, PTH, vasoactive intestinal and related polypeptide (VIP), somatostatin, dopamine, motilin, amylin, bradykinin, calcitonin gene-related peptide (CGRP), leukotrienes, pancreastatin, prostaglandins, thromboxane, adenosine, adrenaline, $\alpha$ and $\beta$-chemokines (e.g., IL-8, GRO$\alpha$, GRO$\beta$, GRO$\gamma$, NAP-2, ENA-78, PF4, IP10, GCP-2, MCP-1, HC14, MCP-3, I-309, MIP-1$\alpha$, MIP-1$\beta$, RANTES, etc.), endothelin, enterogastrin, histamin, neurotensin, TRH, pancreatic polypeptide, galanin, etc.) as well as other substances, for example, tissue extracts and cell culture supernatants from humans and mammals (e.g., mice, rats, swine, bovine, sheep, monkeys). For example, the tissue extract or cell culture supernatant (specifically, particular peptide fragments of KiSS-1 described in Welch D. R., J. Natl. Cancer Inst., 88, 1731 (1996) (e.g., a peptide composed of 8 to 54 amino acid residues and containing a sequence of 47 to 54 amino acids from the N-terminus in the amino acid sequence represented by SEQ ID NO: 10, or amides, esters or salts thereof) is added to the receptor protein or the like of the present invention and fractionated while assaying the cell-stimulating activities to finally give a single ligand.

In more detail, the method for determining a ligand of the present invention comprises determining compounds (e.g., peptides, proteins, non-peptide compounds, synthetic compounds, fermentation products) or salts thereof that bind to the receptor protein or the like of the present invention to provide cell stimulating activities (e.g., the activities that promote or suppress arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos and pH reduction), using the receptor or the like of the present invention, or using the constructed recombinant receptor protein expression system in the receptor binding assay.

The method for determining a ligand of the present invention is characterized, for example, by measurement of the amount of the test compound bound to the receptor protein or the like of the present invention or the cell-stimulating activity when the test compound is brought in contact with the receptor or the like of the present invention.

More specifically, the present invention provides the following:

(1) A method for determining a ligand to the receptor protein of the present invention and salts thereof which comprises bringing a labeled test compound in contact with the receptor protein or the like of the present invention and measuring the amount of the labeled test compound bound to the receptor protein or the like;

(2) A method for determining a ligand to the receptor protein of the present invention and salts thereof which comprises bringing a labeled test compound in contact with cells containing the receptor protein or the like of the present invention or with a membrane fraction of the cells and measuring the amount of the labeled test compound bound to the cells or the membrane fraction;

(3) A method for determining a ligand to the receptor protein of the present invention and salts thereof which comprises culturing a transformant containing DNA encoding the receptor protein or the like of the present invention, bringing a labeled test compound in contact with the receptor protein or the like expressed on the cell membrane by said culturing, and measuring the amount of the labeled test compound bound to the expressed receptor protein or the like;

(4) A method for determining a ligand to the receptor protein of the present invention and salts thereof which comprises bringing a test compound in contact with cells containing the receptor protein or the like of the present invention and measuring the receptor protein-mediated cell stimulating activities (e.g., the activities that promote or suppress arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos and pH reduction); and, (5) A method for determining a ligand to the receptor protein of the present invention and salts thereof which comprises culturing a transformant containing DNA encoding the receptor protein or the like of the present invention, bringing a labeled test compound in contact with the receptor protein or the like expressed on the cell membrane by said culturing, and measuring the receptor protein-mediated cell stimulating activities (e.g., the activities that promote or suppress arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos and pH reduction).

In particular, it is preferred to perform the methods (1) to (3) thereby to confirm that a test compound can bind to the receptor protein or the like of the present invention, followed by the methods (4) and (5).

Any protein exemplified to be usable as the receptor protein or the like of the present invention can be used for the method for the present invention for determining ligands. However, the receptor protein or the like of the present invention that is abundantly expressed using animal cells is appropriate for the present invention.

The receptor protein or the like of the present invention can be manufactured by the method for expression described above, preferably by expressing DNA encoding the receptor protein or the like in mammalian or insect cells. DNA fragments encoding the desired portion of the protein include, but are not limited to, complementary DNA. For example, gene fragments or synthetic DNA may also be used. For introducing a DNA fragment encoding the receptor protein or the like of the present invention into host animal cells and efficiently expressing the same, it is preferred to insert the DNA fragment downstream the polyhedrin promoter of nuclear polyhedrosis virus (NPV), which is a baculovirus having insect hosts, an SV40-derived promoter, a retrovirus promoter, a metallothionein promoter, a human heat shock promoter, a cytomegalovirus promoter, an SRα promoter or the like. The amount and quality of the receptor expressed can be determined by a publicly known method. For example, this determination can be made by the method described in the literature (Nambi, P. et al., J. Biol. Chem., Vol. 267, pp. 19555-19559 (1992)).

Accordingly, the subject containing the receptor protein or the like in the method of the present invention for determining the ligand may be the receptor protein or the like purified by publicly known method, cells containing the receptor protein or membrane fraction of such cells.

Where cells containing the receptor protein or the like of the present invention are used for the method for the present invention for determination of ligands, the cells may be fixed using glutaraldehyde, formalin etc. The fixation can be made by a publicly known method.

Cells containing the receptor protein or the like of the present invention are host cells that have expressed the receptor protein or the like of the present invention, which host cells include *Escherichia coli, Bacillus subtilis*, yeast, insect cells and animal cells.

The cell membrane fraction is a fraction abundant in cell membrane obtained by cell disruption and subsequent fractionation by a publicly known method. Useful cell disruption methods include cell squashing using a Potter-Elvehjem homogenizer, disruption using a Waring blender or Polytron (manufactured by Kinematica Inc.), disruption by ultrasonication, and disruption by cell spraying via a thin nozzle under increased pressure using a French press or the like. Cell membrane fractionation is effected mainly by fractionation using a centrifugal force, such as centrifugation for fractionation and density gradient centrifugation. For example, cell disruption fluid is centrifuged at a low rate (500 to 3,000 rpm) for a short period of time (normally about 1 to 10 minutes), the resulting supernatant is then centrifuged at a higher rate (15,000 to 30,000 rpm) normally for 30 minutes to 2 hours. The precipitate thus obtained is used as the membrane fraction. The membrane fraction is rich in the receptor protein or the like expressed and membrane components such as cell-derived phospholipids and membrane proteins.

The amount of the receptor protein or the like in the cells containing the receptor protein or the like and in the membrane fraction is preferably $10^3$ to $10^8$ molecules per cell, more preferably $10^5$ to $10^7$ molecules per cell. As the amount of expression increases, the ligand binding activity per unit of membrane fraction (specific activity) increases so that not only the highly sensitive screening system can be constructed but also large quantities of samples can be assayed with the same lot.

To perform the methods (1) through (3) for determination of a ligand to the receptor protein of the present invention or salts thereof, an appropriate receptor fraction and a labeled test compound are required.

The receptor protein fraction is preferably a fraction of naturally occurring receptor protein or a recombinant receptor fraction having an activity equivalent to that of the natural protein. Herein, the term "equivalent activity" is intended to mean a ligand binding activity or a signal transduction activity that is equivalent to that possessed by naturally occurring receptor proteins.

Preferred examples of labeled test compounds include angiotensin, bombesin, canavinoid, cholecystokinin, glutamine, serotonin, melatonin, neuropeptide Y, opioid, purines, vasopressin, oxytocin, PACAP, secretin, glucagon, calcitonin, adrenomedulin, somatostatin, GHRH, CRF, ACTH, GRP, PTH, vasoactive intestinal polypeptide (VIP), somatostatin, dopamine, motilin, amylin, bradykinin, calcitonin gene-related peptide (CGRP), leukotrienes, pancreastatin, prostaglandins, thromboxane, adenosine, adrenaline, α and β-chemokines (e.g., IL-8, GROα, GROβ, GROγ, NAP-2, ENA-78, PF4, IP10, GCP-2, MCP-1, HC14, MCP-3, I-309, MIP-1α, MIP-1β, RANTES, etc.), endothelin, enterogastrin, histamin, neurotensin, TRH, pancreatic polypeptide, galanin, etc.) as well as particular peptide fragments of KiSS-1 described in Welch D. R., J. Natl. Cancer Inst., 88, 1731 (1996) (e.g., a peptide of 6-54 amino acid residues containing 47-54 amino acid sequence from the N-terminus in the amino acid sequence represented by SEQ ID NO: 10, or amides, esters or salts thereof), which are labeled with [$^3$H], [$^{125}$I], [$^{14}$C], [$^{35}$S], etc.

More specifically, the ligand to the receptor protein or the like of the present invention is determined by the following procedures. First, a standard receptor preparation is prepared by suspending cells containing the receptor protein or the like of the present invention or the membrane fraction thereof in a buffer appropriate for use in the determination method. Any buffer can be used so long as it does not interfere with ligand-receptor binding, such buffers including a phosphate buffer or a Tris-HCl buffer having pH of about 4 to 10 (preferably pH of about 6 to 8). For the purpose of minimizing non-specific binding, a surfactant such as CHAPS, Tween-80™ (manufactured by Kao-Atlas Inc.), digitonin or deoxycholate, and various proteins such as bovine serum albumin or gelatin, may optionally be added to the buffer. Further for the purpose of suppressing the degradation of the receptor or ligand by protease, a protease inhibitor such as PMSF, leupeptin, E-64 (manufactured by Peptide Institute, Inc.) and pepstatin may also be added. A given amount (5,000 to 500,000 cpm) of the test compound labeled with [$^3$H], [$^{125}$I], [$^{14}$C], [$^{35}$S] or the like is added to 0.01-10 ml of the receptor solution. To determine the amount of non-specific binding (NSB), a reaction tube containing an unlabeled test compound in a large excess is also provided. The reaction is carried out at approximately 0 to 50° C., preferably about 4 to 37° C. for about 20 minutes to about 24 hours, preferably about 30 minutes to 3 hours. After completion of the reaction, the reaction mixture is filtrated through glass fiber filter paper etc. and washed with an appropriate amount of the same buffer. The residual radioactivity in the glass fiber filter paper is then measured by means of a liquid scintillation counter or γ-counter. A test compound exceeding 0 cpm in count obtained by subtracting nonspecific binding (NSB) from the total binding (B) (B minus NSB) may be selected as a ligand (agonist) to the receptor protein of the present invention or salts thereof.

The method (4) or (5) above for determination of a ligand to the receptor protein of the present invention or salts thereof can be performed as follows. The receptor protein-mediated cell-stimulating activities (e.g. the activities that promote or suppress arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos and pH reduction) may be determined by a publicly known method, or using an assay kit commercially available. Specifically, cells containing the receptor protein are first cultured on a multiwell plate, etc. Prior to the ligand determination, the medium is replaced with fresh medium or with an appropriate non-cytotoxic buffer, followed by incubation for a given period of time in the presence of a test compound, etc. Subsequently, the cells are extracted or the supernatant is recovered and the resulting product is quantified by appropriate procedures. Where it is difficult to detect the production of the index substance for the cell-stimulating activity (e.g., arachidonic acid) due to a degrading enzyme contained in the cells, an inhibitor against such a degrading enzyme may be added prior to the assay. For detecting activities such as the cAMP production suppression activity, the baseline production in the cells is increased by forskolin or the like and the suppressing effect on the increased baseline production can then be detected.

The kit of the present invention for determination of a ligand that binds to the receptor protein or the like of the present invention comprises the receptor protein or the like of the present invention, cells containing the receptor protein or the like of the present invention, or the membrane fraction of the cells containing the receptor protein or the like of the present invention.

Examples of the ligand determination kit of the present invention are given below.

1. Reagents for Determining Ligands (1) Buffers for Assay and Washing

Hanks' Balanced Salt Solution (manufactured by Gibco Co.) supplemented with 0.05% bovine serum albumin (Sigma Co.).

The solution is sterilized by filtration through a 0.45 μm filter and stored at 4° C. Alternatively, the solution may be prepared at use.

(2) Standard Receptor Protein

CHO cells on which the receptor protein of the present invention has been expressed are subjected to passage culture in a 12-well plate in a density of $5\times10^5$ cells/well followed by culturing at 37° C. under 5% $CO_2$ and 95% air for two days.

(3) Labeled Test Compounds

Compounds labeled with commercially available [$^3$H], [$^{125}$I], [$^{14}$C] or [$^{35}$S] or compounds labeled by appropriate methods.

An aqueous solution of the compound is stored at 4° C. or −20° C. The solution is diluted to 1 μM with an assay buffer at use. A sparingly water-soluble test compound is dissolved in dimethylformamide, DMSO or methanol.

(4) Non-Labeled Compounds

A non-labeled form of the same compound as the labeled compound is prepared in a concentration 100 to 1,000-fold higher than that of the labeled compound.

2. Method for Assay (1) CHO cells expressing the receptor protein of the present invention are cultured in a 12-well culture plate. After washing twice with 1 ml of an assay buffer, 490 μl of the assay buffer is added to each well.

(2) After 5e μl of the labeled test compound is added, the resulting mixture is incubated at room temperature for an hour. To determine the non-specific binding, 5 μl of the non-labeled compound is added to the system.

(3) The reaction mixture is removed and the wells are washed 3 times with 1 ml of washing buffer. The labeled test compound bound to the cells is dissolved in 0.2N NaOH-1%

SDS, and then mixed with 4 ml of liquid scintillator A (manufactured by Wako Pure Chemical Industries, Ltd.).

(4) The radioactivity is measured using a liquid scintillation counter (manufactured by Beckman Co.).

The ligands that bind to the receptor protein or the like of the present invention include substances specifically present in the brain, pituitary gland and pancreas. Examples of such ligands are angiotensin, bombesin, canavinoid, cholecystokinin, glutamine, serotonin, melatonin, neuropeptide Y, opioids, purines, vasopressin, oxytocin, PACAP, secretin, glucagon, calcitnonin, adrenomedulin, somatostatin, GHRH, CRF, ACTH, GRP, PTH, vasoactive intestinal peptide (VIP), somatostatin, dopamine, motilin, amylin, bradykinin, calcitonin gene-related peptide (CGRP), leukotriens, pancreastatin, prostaglandins, thromboxane, adenosine, adrenaline, α and β-chemokines (e.g. IL-8, GROα, GROβ, GROγ, NAP-2, ENA-78, PF4, IP10, GCP-2, MCP-1, HC14, MCP-3, I-309, MIP1α, MIP-1β, and RANTES), endothelin, enterogastrin, histamine, neurotensin, TRH, pancreatic polypeptide and galanin as well as particular peptide fragments of KiSS-1 described in Welch D. R., J. Natl. Cancer Inst., 88, 1731 (1996) (e.g., a peptide composed of 8 to 54 amino acid residues and containing a sequence of 47 to 54 amino acids from the N-terminus in the amino acid sequence represented by SEQ ID NO: 10, or amides, esters or salts thereof).

In particular, as will be later described in Example 3, particular peptide fragments of KiSS-1 described in Welch D. R., J. Natl. Cancer Inst., 88, 1731 (1996) (e.g., a peptide composed of 8 to 54 amino acid residues and containing a sequence of 47 to 54 amino acids from the N-terminus in the amino acid sequence represented by SEQ ID NO: 10, or amides, esters or salts thereof) is exemplified as the ligand that binds to the receptor protein or the like of the present invention.

The term "peptide composed of 8 to 54 amino acid residues and containing a sequence of 47 to 54 amino acids from the N-terminus in the amino acid sequence represented by SEQ ID NO: 10" refers to any peptide so long as it is a peptide composed of 8 to 54 amino acid residues and containing a sequence of 47 to 54 amino acid from the N-terminus in the amino acid sequence represented by SEQ ID NO: 10. Such peptides have substantially the same peptide activities as those of the receptor protein or the like of the present invention (e.g., a ligand-receptor binding property, a cell stimulating activity of the receptor-expressing cell induced by a ligand).

A preferred example of the ligand peptide in the present invention is a peptide composed of 8 to 15 amino acid residues that contains a sequence of 47 to 54 amino acids counted from the N-terminus at the C-terminus in the amino acid sequence represented by SEQ ID NO: 10.

More preferably, the ligand peptide of the present invention includes a peptide (especially amides thereof) represented by SEQ ID NO: 11, 12, 13 or 14.

Most preferably, the ligand peptide of the present invention includes a peptide in which the carboxyl group at the C-terminal amino acid is amidated.

Regarding the amides or esters of these peptides and salts thereof, the same disclosure as in the salts of the receptor protein of the present invention and the amides or esters of the peptide fragments applies.

For the polynucleotide encoding the ligand peptide of the present invention, any polynucleotide can be used as long as it contains the base sequence (DNA or RNA, preferably DNA) encoding the ligand peptide of the present invention. Such a polynucleotide may be DNA and RNA including mRNA encoding the ligand peptide of the present invention.

The polynucleotide may be double-stranded or single-stranded. Where the polynucleotide is double-stranded, it may be double-stranded DNA or DNA:RNA hybrid. Where the polynucleotide is single-stranded, it may be a sense strand (i.e., a coding strand) or an antisense strand (i.e., a non-coding strand).

The DNA encoding the ligand peptide of the present invention may be any of genomic DNA, genomic DNA library, cDNA derived from the cells and tissues described above, cDNA library derived from the cells and tissues described above and synthetic DNA. The vector to be used for the library may be any of bacteriophage, plasmid, cosmid and phagemid. The DNA may also be directly amplified by reverse transcriptase polymerase chain reaction (RT-RCR) using the total RNA or mRNA fraction prepared from the cells and tissues described above.

Specifically, the DNA encoding the ligand peptide of the present invention may be any DNA so long as it has a sequence of 47 to 54 amino acids counted from the N-terminus in the amino acid sequence represented by SEQ ID NO: 10 and contains DNA having the base sequence encoding a peptide composed of 8 to 54 amino acid residues.

More specific examples of the DNA encoding the ligand peptide of the present invention include DNA containing DNA having the base sequence encoding the peptide that has 47-54 amino acid sequence from the N-terminus at the C-terminus of the amino acid sequence represented by SEQ ID NO: 10 and comprises 8 to 15 amino acid residues. More specifically, the DNA encoding the ligand peptide of the present invention includes DNA containing a DNA having the base sequence encoding the peptide that contains the amino acid sequence represented by SEQ ID NO: 11, 12, 13 or 14 and comprises 8 to 15 amino acid residues.

The DNA encoding the ligand peptide of the present invention is, for example, DNA containing the 139-162 base sequence from the 5' end in the base sequence represented by SEQ ID NO: 15, and comprising 24 to 162 bases, or the like. More specifically, the DNA encoding the ligand peptide of the present invention includes DNA containing the 139-162 base sequence from the 5' end at the 3' end of the base sequence represented by SEQ ID NO: 15 and comprising 24 to 45 bases.

Typical examples of the DNA encoding the ligand peptide of the present invention include DNAs containing the DNAs bearing the respective base sequences represented by SEQ ID NO: 16, 17, 18 and 19.

Herein, specific examples of the DNA encoding the each sequence corresponding to the SEQ ID NO are:

(1) for the DNA encoding the amino acid sequence represented by SEQ ID NO: 10, DNA containing DNA having the base sequence represented by SEQ ID NO: 15;

(2) for the DNA encoding the amino acid sequence represented by SEQ ID NO: 11, DNA containing DNA having the base sequence represented by SEQ ID NO: 16;

(3) for the DNA encoding the amino acid sequence represented by SEQ ID NO: 12, DNA containing DNA having the base sequence represented by SEQ ID NO: 17;

(4) for the DNA encoding the amino acid sequence represented by SEQ ID NO: 13, DNA containing DNA having the base sequence represented by SEQ ID NO: 18; and, (5) for the DNA encoding the amino acid sequence represented by SEQ ID NO: 14, DNA containing DNA having the base sequence represented by SEQ ID NO: 19.

The ligand peptide of the present invention or esters, amides or salts thereof as well as the polynucleotide encoding the ligand peptide may be manufactured in a manner similar to the methods for manufacturing the receptor protein or the like of the present invention and the polynucleotide encoding the same.

The ligand peptide of the present invention, esters or amides or salts thereof (hereinafter sometimes referred to as the ligand peptide or the like of the present invention) as well as the polynucleotide encoding the ligand peptide are useful as a safe and low toxic drug depending on the ligand activity.

The ligand peptide or the like of the present invention and the DNA encoding the same possess a cancer metastasis suppressing activity and are thus useful for prophylactic or therapeutic drug of all cancers (e.g., lung cancer, gastric cancer, liver cancer, pancreas cancer, large intestine cancer, rectal cancer, colon cancer, prostate cancer, ovary cancer, uterocervical cancer, breast cancer, etc)

The ligand peptide or the like of the present invention and the DNA encoding the same also possess a placenta function regulating activity and are thus useful for prophylactic or therapeutic drug of cilia cancer, hydatid mole, invasive mole, miscarriage, fetal hypoplasia, sugar dysbolism, lipid dysbolism or labor induction.

Where the ligand peptide or the like of the present invention is used as a prophylactic/therapeutic agent as described above, the ligand peptide or the like can be prepared into a pharmaceutical preparation by a publicly known method.

When the DNA encoding the ligand peptide of the present invention (hereinafter sometimes referred to as the ligand DNA of the present invention) is used as a prophylactic/therapeutic agent as described above, the ligand DNA of the present invention may be used alone or after inserting it into a appropriate vector such as retrovirus vector, adenovirus vector or adenovirus-associated virus vector followed by a conventional means for drug administration. The ligand DNA of the present invention can also be administered as naked DNA, or with adjuvants to assist its uptake by gene gun or through a catheter such as a catheter with a hydrogel.

For example, (1) the ligand peptide or the like of the present invention or (2) the DNA encoding the ligand peptide can be used orally in the form of tablets which may be sugar coated if necessary and desired, capsules, elixirs, microcapsules etc., or parenterally in the form of injectable preparations such as a sterile solution and a suspension in water or with other pharmaceutically acceptable liquid. These preparations can be manufactured by mixing (1) the ligand peptide or the like of the present invention or (2) the DNA encoding the ligand peptide with a physiologically acceptable known carrier, flavoring agent, excipient, vehicle, antiseptic, stabilizer, binder, etc. in a unit dosage form required in a generally accepted manner applied to making pharmaceutical preparations. The active ingredient in the preparation is controlled in such a dose that an appropriate dose is obtained within the specified range given.

Additives miscible with tablets, capsules etc. include a binder such as gelation, corn starch, tragacanth and gum arabic, an excipient such as crystalline cellulose, a swelling agent such as corn starch, gelatin and alginic acid, a lubricant such as magnesium stearate, a sweetening agent such as sucrose, lactose and saccharin, and a flavoring agent such as peppermint, akamono oil and cherry. When the unit dosage is in the form of capsules, liquid carriers such as oils and fats may further be used together with the additives described above. A sterile composition for injection may be formulated according to a conventional manner used to make pharmaceutical compositions, e.g., by dissolving or suspending the active ingredients in a vehicle such as water for injection with a naturally occurring vegetable oil such as sesame oil and coconut oil, etc. to prepare the pharmaceutical composition.

Examples of an aqueous medium for injection include physiological saline and an isotonic solution containing glucose and other auxiliary agents (e.g., D-sorbitol, D-mannitol and sodium chloride) and may be used in combination with an appropriate dissolution aid such as an alcohol (e.g., ethanol), a polyalcohol (e.g., propylene glycol and polyethylene glycol), a nonionic surfactant (e.g., polysorbate 80™ and HCO-50), etc. As an oily medium, for example, sesame oil and soybean oil may be used, which can be used in combination with a dissolution aid such as benzyl benzoate and benzyl alcohol.

Furthermore the prophylactic/therapeutic agent described above may also be formulated with a buffer (e.g., phosphate buffer and sodium acetate buffer), a soothing agent (e.g. benzalkonium chloride, procaine hydrochloride), a stabilizer (e.g., human serum albumin, polyethylene glycol), a preservative (e.g., benzyl alcohol, phenol), an antioxidant, etc. The thus-prepared liquid for injection is normally filled in an appropriate ampoule.

Since the thus obtained pharmaceutical preparation is safe and low toxic, the preparation can be administered to human or mammals (e.g., rat, mouse, rabbit, sheep, swine, bovine, cat, dog, monkey, etc.).

The dose of the ligand peptide or the like of the present invention varies depending on subject to be administered, target organ, symptom, route for administration, etc.; in oral administration, the dose is normally about 0.1 to about 100 mg, preferably about 1.0 to about 50 mg, and more preferably about 1.0 to about 20 mg per day for a patient with cancer (weighing 60 kg). In parenteral administration, the single dose varies depending on subject to be administered, target organ, symptom, route for administration, etc. but it is advantageous to administer the active ingredient intravenously at a daily dose of about 0.01 to about 30 mg, preferably about 0.1 to about 20 mg, and more preferably about 0.1 to about 10 mg for a patient with cancer (weighing 60 kg). For other animal species, the corresponding dose as converted per 60 kg weight can be administered.

The dose of the ligand DNA of the present invention varies depending on subject to be administered, target organ, symptom, route for administration, etc.; in oral administration, the dose is normally about 0.1 to about 100 mg, preferably about 1.0 to about 50 mg, and more preferably about 1.0 to about 20 mg per day for a patient with cancer (weighing 60 kg). In parenteral administration, the single dose varies depending on subject to be administered, target organ, symptom, route for administration, etc. but it is advantageous to administer the active ingredient intravenously at a daily dose of about 0.01 to about 30 mg, preferably about 0.1 to about 20 mg, and more preferably about 0.1 to about 10 mg for a patient with cancer (weighing 60 kg). For other animal species, the corresponding dose as converted per 60 kg weight can be administered.

(2) Prophylactic and/or Therapeutic Agents for Diseases Associated with the Dysfunction of the Receptor Protein of the Present Invention The receptor protein or the like of the present invention or the DNA encoding the receptor protein or the like can be used as a prophylactic and/or therapeutic agents for diseases associated with the dysfunction of the ligand peptide of the present invention.

For example, when any physiological activity of the receptor protein of the present invention cannot be expected due to a reduced level of the receptor protein in a patient (deficiency of the receptor protein), the ligand activity can be exhibited by the following methods: (1) the receptor protein or the like of the present invention is administered to the patient to supplement the amount of the receptor protein or the like; or (2) the amount of the receptor protein of the present invention is increased in the patient by: a) administration of the DNA encoding the receptor protein of the present invention to the patient for expression, or by b) insertion of the DNA encoding the receptor protein of the present invention in the target cells for expression, and the cells thus expressed are then transplanted into the patient. Thus, the amount of the receptor protein of the present invention can be increased in the patient, whereby the ligand activity can be exhibited sufficiently. Therefore, the receptor protein or the like of the present invention or the DNA encoding the receptor protein of the present invention is useful as a safe and low toxic prophylactic and/or therapeutic drug for diseases associated with the dysfunction of the receptor protein of the present invention.

The receptor protein or the like of the present invention and the DNA encoding the receptor protein or the like possess a cancer metastasis suppressing activity and are thus useful for prophylactic or therapeutic drug of all cancers (e.g., lung cancer, gastric cancer, liver cancer, pancreas cancer, large intestine cancer, rectal cancer, colon cancer, prostate cancer, ovary cancer, uterocervical cancer, breast cancer, etc).

The receptor protein or the like of the present invention or the ligand peptide of the present invention and the DNA encoding the receptor protein or the like of the present invention or the ligand peptide of the present invention also possess a placenta function regulating activity and are thus useful for prophylactic or therapeutic drug of cilia cancer, hydatid mole, invasive mole, miscarriage, fetal hypoplasia, sugar dysbolism, lipid dysbolism or labor induction.

Where the receptor protein or the like of the present invention is used as a prophylactic/therapeutic agent as described above, the receptor protein or the like can be prepared into a pharmaceutical preparation by a publicly known method.

When the DNA encoding the receptor protein or the like of the present invention (hereinafter sometimes referred to as the DNA of the present invention) is used as a prophylactic/therapeutic agent as described above, the DNA of the present invention may be used alone or after inserting it into a appropriate vector such as retrovirus vector, adenovirus vector or adenovirus-associated virus vector followed by a conventional means for drug administration. The DNA of the present invention can also be administered as naked DNA, or with adjuvants to assist its uptake by gene gun or through a catheter such as a catheter with a hydrogel.

For example, (1) the receptor protein or the like of the present invention or (2) the DNA encoding the receptor protein or the like can be used orally in the form of tablets which may be sugar coated if necessary and desired, capsules, elixirs, microcapsules etc., or parenterally in the form of injectable preparations such as a sterile solution and a suspension in water or with other pharmaceutically acceptable liquid. These preparations can be manufactured by mixing (1) the receptor protein or the like of the present invention or (2) the DNA encoding the receptor protein or the like with a physiologically acceptable known carrier, flavoring agent, excipient, vehicle, antiseptic, stabilizer, binder, etc. in a unit dosage form required in a generally accepted manner applied to making pharmaceutical preparations. The active ingredient in the preparation is controlled in such a dose that an appropriate dose is obtained within the specified range given.

Additives miscible with tablets, capsules etc. include a binder such as gelatin, corn starch, tragacanth and gum arabic, an excipient such as crystalline cellulose, a swelling agent such as corn starch, gelatin and alginic acid, a lubricant such as magnesium stearate, a sweetening agent such as sucrose, lactose and saccharin, and a flavoring agent such as peppermint, akamono oil and cherry. When the unit dosage is in the form of capsules, liquid carriers such as oils and fats may further be used together with the additives described above. A sterile composition for injection may be formulated according to a conventional manner used to make pharmaceutical compositions, e.g., by dissolving or suspending the active ingredients in a vehicle such as water for injection with a naturally occurring vegetable oil such as sesame oil and coconut oil, etc. to prepare the pharmaceutical composition. Examples of an aqueous medium for injection include physiological saline and an isotonic solution containing glucose and other auxiliary agents (e.g., D-sorbitol, D-mannitol and sodium chloride) and may be used in combination with an appropriate dissolution aid such as an alcohol (e.g., ethanol), a polyalcohol (e.g., propylene glycol and polyethylene glycol), a nonionic surfactant (e.g., polysorbate 80™ and HCO-50), etc. As an oily medium, for example, sesame oil and soybean oil may be used, which can be used in combination with a dissolution aid such as benzyl benzoate and benzyl alcohol.

Furthermore the prophylactic/therapeutic agent described above may also be formulated with a buffer (e.g., phosphate buffer and sodium acetate buffer) a soothing agent (e.g., benzalkonium chloride, procaine hydrochloride), a stabilizer (e.g., human serum albumin, polyethylene glycol), a preservative (e.g., benzyl alcohol, phenol), an antioxidant, etc. The thus-prepared liquid for injection is normally filled in an appropriate ampoule.

Since the thus obtained pharmaceutical preparation is safe and low toxic, the preparation can be administered to human or mammals (e.g., rat, mouse, rabbit, sheep, swine, bovine, cat, dog, monkey, etc.).

The dose of the receptor protein or the like of the present invention varies depending on subject to be administered, target organ, symptom, route for administration, etc.; in oral administration, the dose is normally about 0.1 to about 100 mg, preferably about 1.0 to about 50 mg, and more preferably about 1.0 to about 20 mg per day for a patient with cancer (weighing 60 kg). In parenteral administration, the single dose varies depending on subject to be administered, target organ, symptom, route for administration, etc. but it is advantageous to administer the active ingredient intravenously at a daily dose of about 0.01 to about 30 mg, preferably about 0.1 to about 20 mg, and more preferably about 0.1 to about 10 mg for a patient with cancer (weighing 60 kg). For other animal species, the corresponding dose as converted per 60 kg weight can be administered.

The dose of the DNA encoding the receptor protein of the present invention varies depending on subject to be administered, target organ, symptom, route for administration, etc.; in oral administration, the dose is normally about 0.1 to about 100 mg, preferably about 1.0 to about 50 mg, and more preferably about 1.0 to about 20 mg per day for a patient with cancer (weighing 60 kg). In parenteral administration, the single dose varies depending on subject to be administered, target organ, symptom, route for administration, etc. but it is advantageous to administer the active ingredient intravenously at a daily dose of about 0.01 to about 30 mg, preferably about 0.1 to about 20 mg, and more preferably about 0.1 to about 10 mg for a patient with cancer (weighing 60 kg). For other animal species, the corresponding dose as converted per 60 kg weight can be administered.

(3) Gene Diagnostic Agent

Using as a probe the DNA encoding the receptor protein of the present invention or the DNA encoding the ligand peptide of the present invention, an abnormality (gene abnormality) of the DNA or mRNA coding for the receptor protein or the like of the present invention or the ligand peptide of the present invention in human or mammal (e.g., rat, mouse, rabbit, sheep, swine, bovine, cat, dog, monkey, etc.) can be detected. Therefore, the DNA of the present invention is useful as a gene diagnostic agent for the damage to the DNA or mRNA, mutation thereof, or decreased expression thereof, or increased expression or overexpression of the DNA or mRNA.

The gene diagnosis described above using the DNA encoding the receptor protein of the present invention or the DNA encoding the ligand peptide of the present invention can be performed by, for example, publicly known Northern hybridization assay or PCR-SSCP assay (Genomics, 5, 874-879 (1989); Proceedings of the National Academy of Sciences of the United States of America, 86, 2766-2770 (1989)).

(4) Quantification of Ligand to the Receptor Protein or the Like of the Present Invention Since the receptor protein or the like of the present invention has a binding property to ligand, the ligand activity can be quantified in vivo with high sensitivity.

The method for quantification of the present invention may be effected, for example, in combination with a competitive method. Thus, a sample to be determined is brought into contact with the receptor protein or the like of the present invention, whereby the ligand concentration in the sample can be determined. Specifically, the quantification can be performed by the following method (1) or (2) below or its modification:

(1) Hiroshi Irie (ed.): "Radioimmunoassay" (1974, published by Kodansha, Japan); and (2) Hiroshi Irie (ed.): "Radioimmunoassay, Second Series" (1979, published by Kodansha, Japan).

(5) A Method for Screening of the Compound (Agonist, Antagonist, etc.) that Alters the Binding Property Between the Receptor Protein, Salts Thereof and Ligand of the Present Invention (Ligand Peptide of the Present Invention)

By using the receptor protein of the present invention or salts thereof, or by constructing the expression system of recombinant receptor protein or the like and using the receptor-binding assay system via the expression system, screening can be made efficiently on the compound (e.g., peptide, protein, a non-peptide compound, a synthetic compound, fermentation product, etc.) or salts thereof that alter the binding property between the ligand (ligand peptide of the present invention) and the receptor protein or the like of the present invention.

Examples of the above compounds include (a) a compound exhibiting cell stimulating activities mediated by the G protein coupled receptor (e.g., the activities that promote or suppress arachidonic acid release, acetylcholine release, intracellular $Ca^{2+}$ release, intracellular cAMP production, intracellular CGMP production, inositol phosphate production, change in cell membrane potential, phosphorylation of intracellular proteins, activation of c-fos and pH reduction) (so-called agonists to the receptor protein or the like of the present invention), (b) a compound free of such a cell stimulating activity (so-called antagonists to the receptor protein or the like of the present invention); or (c) a compound that decreases the binding property between ligand (ligand peptide of the present invention) and the receptor protein or the like of the present invention (the compound (a) is screened preferably by the method for determination of ligand described above).

Thus, the present invention also provides a method for screening a compound or a salt thereof that alters the binding property between the receptor protein or the like of the present invention and the ligand (ligand peptide of the present invention), which comprises comparing the following two cases: (i) the case wherein the receptor protein or the like of the present invention is brought in contact with the ligand (ligand peptide of the present invention); and (ii) the case wherein the receptor protein or the like of the present invention is brought in contact with the ligand (ligand peptide of the present invention) and a test compound.

In the screening method for the present invention, comparison is made between the cases (i) and (ii) in terms of, e.g., the amount of the ligand (ligand peptide of the present invention) that binds to the receptor protein or the like, or the cell-stimulating activities.

More specifically, the present invention provides the following methods.

(1) A method for screening a compound or a salt thereof that alters the binding property between a ligand (ligand peptide of the present invention) and the receptor protein or the like of the present invention, which comprises measuring the amount of a labeled ligand (ligand peptide of the present invention) bound to the receptor protein or the like of the present invention in the case wherein the labeled ligand (ligand peptide of the present invention) is brought in contact with the receptor protein or the like of the present invention and in the case wherein the labeled ligand (ligand peptide of the present invention) and a test compound are brought in contact with the receptor protein or the like, and comparing the binding amount of the labeled ligand between the two cases.

(2) A method for screening a compound or a salt thereof that alters the binding property between a ligand (ligand peptide of the present invention) and the receptor protein or the like of the present invention, which comprises measuring the amount of a labeled ligand (ligand peptide of the present invention) bound to cells containing the receptor protein or the like of the present invention or a cell fraction thereof, in the case wherein the labeled ligand (ligand peptide of the present invention) is brought in contact with the cells containing the receptor protein or the like of the present invention or the cell membrane and in the case wherein the labeled ligand (ligand peptide of the present invention) and a test compound are brought in contact with the cells containing the receptor protein or the like or the cell membrane, and comparing the binding amount of the labeled ligand between the two cases.

(3) A method for screening a compound or a salt thereof that alters the binding property between a ligand (ligand peptide of the present invention) and the receptor protein or the like of the present invention, which comprises measuring the amount of a labeled ligand (ligand peptide of the present invention) bound to the receptor protein or the like of the present invention, in the case wherein the labeled ligand (ligand peptide of the present invention) is brought in contact with the receptor protein or the like expressed in the cell membrane by culturing a transformant containing the DNA of the present invention and in the case wherein the labeled ligand (ligand peptide of the present invention) and a test compound are brought in contact with the receptor protein or the like expressed in the cell membrane by culturing a transformant containing the DNA of the present invention, and comparing the binding amount of the labeled ligand between the two cases.

(4) A method for screening a compound or a salt thereof that alters the binding property between a ligand (ligand peptide of the present invention) and the receptor protein or the like of the present invention, which comprises measuring receptor-mediated cell stimulating activities (e.g., the activities that promote or suppress arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos and pH reduction) in the case wherein a compound (e.g., a ligand to the receptor protein or the like of the present invention) that activates the receptor protein or the like of the present invention is brought in contact with cells containing the receptor protein or the like of the present invention and in the case wherein said compound that activates the receptor protein or the like of the present invention and a test compound are brought in contact with the cells containing the receptor protein or the like of the present invention, and comparing the cell stimulating activities between the two cases.

(5) A method for screening a compound or a salt thereof that alters the binding property between a ligand (ligand peptide of the present invention) and the receptor protein or the like of the present invention, which comprises measuring receptor-mediated cell stimulating activities (e.g., the activities that promote or suppress arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos and pH reduction) in the case wherein a compound that activates the ligand peptide or the like of the present invention (e.g., a ligand (ligand of the present invention) to the receptor protein or the like of the present invention) is brought in contact with the receptor protein or the like of the present invention expressed in a cell membrane by culturing a transformant containing the DNA of the present invention and in the case wherein said compound that activates the receptor protein or the like of the present invention and a test compound are brought in contact with the receptor protein or the like of the present invention expressed in a cell membrane by culturing a transformant containing the DNA of the present invention, and comparing the cell stimulating activities between the two cases.

Before the receptor protein or the like of the present invention was obtained, screening of the G protein coupled receptor agonist or antagonist should have been made in terms of whether or not a candidate compound would inhibit the binding between G protein coupled receptor proteins and ligands, using cells, tissues or cell membrane fractions containing G protein coupled receptor proteins. When the cells, tissues or cell membrane fractions are used as they are, however, other receptor proteins inevitably exist. It was thus difficult to screen agonists or antagonists to the desired receptor proteins.

However, the use of the receptor protein or the like of the present invention enables to efficiently screen the compound that inhibits the binding between a ligand and the G protein coupled receptor protein. Besides, it can be simply evaluated whether the compound screened is either an agonist or an antagonist.

Hereinafter the screening method for the present invention will be described more specifically.

First, the receptor protein or the like of the present invention, which is used for the screening method for the present invention, may be any protein so long as it contains the receptor protein or the like of the present invention described above, though a membrane fraction of mammalian organs is preferably employed. For screening that requires large quantities of the receptor protein, it is advantageous to use receptor proteins expressed abundantly by a recombinant.

In the manufacture of the receptor protein or the like of the present invention, the methods described above can be used, though the DNA of the present invention is preferably expressed in mammalian cells or insect cells. As the DNA fragment coding for the target protein region, complementary DNA may be used but is not limited thereto. For example, gene fragments or synthetic DNA may also be used as the DNA fragment. In order to introduce the DNA fragment coding for the receptor protein of the present invention into host animal cells and express it efficiently, the DNA fragment is preferably incorporated into a polyhedron promoter of nuclear polyhedrosis virus (NPV) belonging to the baculovirus, a SV40-derived promoter, a promoter of retrovirus, a metallothionein promoter, a human heat shock promoter, a cytomegalovirus promoter, SRα promoter, etc. at the downstream thereof. The amount and quality of the thus expressed receptors can be examined by a publicly known method, for example, by the method described in Nambi, P. et al., J. Biol. Chem., 267, 19555-19559 (1992).

Accordingly, in the screening method for the present invention, the substance containing the receptor protein or the like of the present invention may be the receptor protein or the like that is purified by publicly known methods. Alternatively, cells containing the receptor protein or the like or a cell membrane fraction of the cells containing the receptor protein or the like may be used as well.

Where the cells containing the receptor protein or the like of the present invention are used in the screening method for the present invention, these cells may be fixed with glutaraldehyde, formalin, etc. The fixation may be carried out by a publicly known method.

The cells containing the receptor protein or the like of the present invention refer to host cells expressing the receptor protein or the like. Examples of such host cells include *Escherichia coli, Bacillus subtilis*, yeast, insect cells and animal cells.

The cell membrane fraction refers to a fraction that abundantly contains the cell membranes prepared by a publicly known method after disrupting the cells. Examples of cell disruption include cell squashing using a Potter-Elvehjem homogenizer, disruption using a Waring blender or Polytron (manufactured by Kinematica Inc.), disruption by ultrasonication, and disruption by cell spraying via a thin nozzle under increased pressure using a French press or the like. Cell membrane fractionation is effected mainly by fractionation using a centrifugal force, such as centrifugation for fractionation and density gradient centrifugation. For example, cell disruption fluid is centrifuged at a low rate (500 rpm to 3,000 rpm) for a short period of time (normally about 1 to 10 minutes), the resulting supernatant is then centrifuged at a higher rate (15,000 rpm to 30,000 rpm) normally for 30 minutes to 2 hours. The precipitate thus obtained is used as the membrane fraction. The membrane fraction is rich in the receptor protein or the like expressed and membrane components such as cell-derived phospholipids and membrane proteins.

The amount of the receptor protein contained in the cells containing the receptor protein or the like or in the membrane fraction is preferably $10^3$ to $10^8$ molecules per cell, more preferably $10^5$ to $10^7$ molecules per cell. As the amount of expression increases, the ligand binding activity per unit of membrane fraction (specific activity) increases so that not only the highly sensitive screening system can be constructed but also large quantities of samples can be assayed with the same lot.

To perform the methods (1) through (3) for screening the compound that alters the binding property between the ligand (ligand peptide of the present invention) and the receptor protein or the like of the present invention, an appropriate receptor protein fraction and a labeled ligand are required.

The receptor protein fraction is preferably a fraction of naturally occurring receptor protein or a recombinant receptor protein fraction having an activity equivalent to that of the naturally occurring protein. Herein, the term "equivalent activity" is intended to mean a ligand binding activity or a signal transduction activity that is equivalent to that possessed by naturally occurring receptor proteins.

Examples of the labeled ligand include ligands that are labeled with [$^3$H], [$^{125}$I], [$^{14}$C] or [$^{35}$S].

More specifically, the compound that alters the binding property between the ligand (ligand peptide of the present invention) and the receptor protein or the like of the present invention, is screened by the following procedures. First, a standard receptor preparation is prepared by suspending cells containing the receptor protein or the like of the present invention or the membrane fraction thereof in a buffer appropriate for use in the screening method. Any buffer can be used so long as it does not interfere the ligand-receptor binding. Examples of such buffers are a phosphate buffer or a Tris-HCl buffer, having pH of about 4 to 10 (preferably pH of about 6 to 8). For the purpose of minimizing non-specific binding, a surfactant such as CHAPS, Tween-80™ (Kao-Atlas Inc.), digitonin or deoxycholate may be added to buffers. Further for the purpose of suppressing the degradation of the receptor or ligand (ligand peptide of the present invention) by protease, a protease inhibitor such as PMSF, leupeptin, E-64 (manufactured by Peptide Institute, Inc.) and pepstatin may also be added. A given amount (5,000 to 500,000 cpm) of the ligand (ligand peptide of the present invention) labeled is added to 0.01 to 10 ml of the receptor solution, in which $10^{-4}$ M to $10^{-10}$ M of the test compound is co-present. To determine the amount of non-specific binding (NSB), a reaction tube containing an unlabeled ligand (ligand peptide of the present invention) in a large excess is also provided. The reaction is carried out at approximately 0 to 50° C., preferably about 4 to 37° C. for about 20 minutes to about 24 hours, preferably about 30 minutes to 3 hours. After completion of the reaction, the reaction mixture is filtrated through glass fiber filter paper, etc. and washed with an appropriate amount of the same buffer. The residual radioactivity in the glass fiber filter paper is then measured by means of a liquid scintillation counter or γ-counter. When nonspecific binding (NSB) is subtracted from the count ($B_0$) where any antagonizing substance is absent and the resulting count ($B_0$ minus NSB) is made 100%, a test compound showing the specific binding amount (B minus NSB) of, e.g., 50% or less may be selected as a candidate compound.

The method (4) or (5) above for screening the compound that alters the binding property between the ligand (ligand peptide of the present invention) and the receptor protein or the like of the present invention can be performed as follows. In one embodiment, the receptor protein-mediated cell stimulating activities (e.g., the activities that promote or suppress arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos and pH reduction) may be determined by a publicly known method, or using an assay kit commercially available.

Specifically, the cells containing the receptor protein or the like of the present invention are first cultured on a multiwell plate, etc. Prior to screening, the medium is replaced with fresh medium or with an appropriate non-cytotoxic buffer, followed by incubation for a given period of time in the presence of a test compound, etc. Subsequently, the cells are extracted or the supernatant is recovered and the resulting product is quantified by appropriate procedures. Where it is difficult to detect the production of the cell-stimulating activity index substance (e.g., arachidonic acid) due to a degrading enzyme contained in the cells, an inhibitor against such a degrading enzyme may be added prior to the assay. For detecting activities such as the cAMP production suppression activity, the baseline production in the cells is increased by forskolin or the like and the suppressing effect on the increased baseline production can then be detected.

For screening through the measurement of the cell stimulating activities, cells in which a appropriate receptor protein is expressed are necessary. Preferred cells in which the receptor protein or the like of the present invention is expressed are a naturally occurring cell line containing the receptor protein or the like of the present invention and the aforesaid cell line in which recombinant type receptor protein or the like is expressed.

Examples of the test compound include peptides, proteins, non-peptide compounds, synthetic compounds, fermentation products, cell extracts, plant extracts and animal tissue extracts. These test compounds may be either novel or publicly known.

A kit for screening the compound or a salt thereof that alters the binding property between the ligand (ligand peptide of the present invention) and the receptor protein or the like of the present invention comprises the receptor protein or the like of the present invention, cells containing the receptor protein or the like of the present invention, or a membrane fraction of the cells containing the receptor protein or the like of the present invention.

Examples of the screening kit include as follows:

1. Reagent for Screening (1) Buffers for Assay and Washing

Hanks' Balanced Salt Solution (manufactured by Gibco) supplemented with 0.05% of bovine serum albumin (manufactured by Sigma).

The buffers may be sterilized by filtration through a membrane filter with a 0.45 μm pore size and stored at 4° C., or may be prepared at use.

(2) G Protein Coupled Receptor Protein Preparation

CHO cells in which the receptor protein of the present invention is expressed are subcultured at $5 \times 10^5$ cells/well on a 12-well plate followed by culturing at 37° C. under a 5% $CO_2$ and 95% air for 2 days.

(3) Labeled Ligand

The ligand which is labeled with commercially available [$^3$H], [$^{125}$I], [$^{14}$C], [$^{35}$S], etc.

The product in the form of an aqueous solution is stored at 4° C. or at −20° C. and diluted to 1 μM with a buffer for the assay at use.

(4) Standard Ligand Solution

Ligand is dissolved in PBS containing 0.1% of bovine serum albumin (manufactured by Sigma) to make 1 mM and stored at −20° C.

2. Method for Assay (1) CHO cells are cultured in a 12-well tissue culture plate to express the receptor protein of the present invention. After washing the receptor protein-expressing CHO cells twice with 1 ml of buffer for the assay, 490 μl of the buffer for assay is added to each well.

(2) After 5 μl of a test compound solution of $10^{-3}$ to $10^{-10}$ M is added, 5 μl of a labeled ligand is added to the system followed by incubating at room temperature for an hour. To determine the amount of the non-specific binding, 5 μl of the ligand of $10^{-3}$ M is added to the system, instead of the test compound.

(3) The reaction mixture is removed from the well, which is washed three times with 1 ml each of the buffer for assay. The labeled ligand bound to the cells is dissolved in 0.2N NaOH-1% SDS and mixed with 4 ml of a liquid scintillator A (manufactured by Wako Pure Chemical, Japan).

(4) Radioactivity is measured using a liquid scintillation counter (manufactured by Beckmann) and PMB (percent of the maximum binding) is calculated in accordance with the following equation:

$$PMB=[(B-NSB)/(B_o-NSB)] \times 100$$

wherein:
PMB: percent of the maximum binding
B: value when a sample is added
NSB: non-specific binding
$B_0$: maximum binding The compound or a salt thereof obtainable by the screening method or by the screening kit of the present invention is a compound that functions to alter the binding property between the ligand (ligand peptide of the present invention) and the receptor protein or the like of the present invention. More specifically, the compound includes (a) a compound exhibiting cell stimulating activities mediated by the G protein coupled receptor (e.g., the activities that promote or suppress arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos and pH reduction) (so-called agonists to the receptor protein of the present invention), (b) a compound free of such a cell stimulating activity (so-called antagonists to the receptor protein of the present invention); and (c) a compound that decreases the binding property between the ligand (ligand peptide of the present invention) and the receptor protein of the present invention.

Examples of such compounds include peptides, proteins, non-peptide compounds, synthetic compounds and fermentation products. These compounds may be either novel or publicly known.

The agonist to the receptor protein or the like of the present invention has the same physiological activity as that of the ligand (ligand peptide of the present invention) to the receptor protein or the like of the present invention. Therefore, the agonist is useful as a safe and low toxic pharmaceutical, depending upon the ligand activity.

In more detail, the agonist to receptor protein or the like of the present invention possesses a cancer metastasis suppressing activity and are thus useful for prophylaxis or therapy of all cancers (e.g., lung cancer, gastric cancer, liver cancer, pancreas cancer, large intestine cancer, rectal cancer, colon cancer, prostate cancer, ovary cancer, uterocervical cancer, breast cancer, etc).

The agonist to receptor protein or the like of the present invention also possesses a placenta function regulating activity and are thus useful for prophylactic or therapeutic drug of cilia cancer, hydatid mole, invasive mole, miscarriage, fetal hypoplasia, sugar dysbolism, lipid dysbolism or labor induction.

The antagonist to the receptor protein or the like of the present invention can suppress the physiological activity that the ligand (ligand peptide of the present invention) to the receptor protein or the like of the present invention has. Therefore, the antagonist is useful as a safe and low toxic pharmaceutical for suppressing the ligand activity.

The compound that decreases the binding between the ligand (ligand peptide of the present invention) and the receptor protein of the present invention is useful as a safe and low toxic pharmaceutical for decreasing the physiological activity that the ligand (ligand peptide of the present invention) to the receptor protein or the like of the present invention has.

When the compound or a salt thereof obtainable by the screening method or by the screening kit of the present invention is used as the pharmaceutical composition described above, a conventional means may be applied to making the composition. For example, the compound or a salt thereof may be prepared into tablets, capsules, elixirs, microcapsules, sterile solutions, suspensions, etc.

Since the thus obtained preparation is safe and low toxic, it can be administered to human or mammals (e.g., rat, mouse, rabbit, sheep, swine, bovine, cat, dog, monkey, etc.).

The dose of the compound or a salt thereof (in the case of agonist) varies depending on subject to be administered, target organ, symptom, method for administration, etc.; in oral administration, the dose is normally about 0.1 to about 100 mg, preferably about 1.0 to about 50 mg, more preferably about 1.0 to about 20 mg per day for a patient with cancer (weighing 60 kg). In parenteral administration, the single dose varies depending on subject to be administered, target organ, symptom, method for administration, etc. but it is advantageous to administer the active ingredient intravenously at a daily dose of about 0.01 to about 30 mg, preferably about 0.1 to about 20 mg, more preferably about 0.1 to about 10 mg for a patient with cancer (weighing 60 kg). For other animal species, the corresponding dose as converted per 60 kg weight can be administered.

(6) A Composition for the Prophylactic and/or Therapy for Various Diseases Comprising the Compound (Agonist, Antagonist) that Alters the Binding Property Between the Receptor Protein or the Like of the Present Invention and the Ligand (Ligand Peptide of the Present Invention)

As stated hereinabove, the receptor protein or the like of the present invention plays some important role in vivo, such as a cancer metastasis-suppressing activity. Therefore, the compound (agonist, antagonist) that alter the binding property between the receptor protein or the like of the present invention and the ligand (ligand peptide of the present invention) can be used for the prophylactic and/or therapeutic agent of diseases associated with dysfunction of the receptor protein or the like of the present invention.

When the compound above is used as the pharmaceutical composition for the prevention and/or treatment of diseases associated with dysfunction of the receptor protein or the like of the present invention, a conventional means may be applied to making the composition.

For example, the compound may be prepared into a sugar coated tablet, a capsule, an elixir or a microcapsule for oral administration and for parenteral administration in the form of injectable preparations such as a sterile solution and a suspension in water or with other pharmaceutically acceptable liquid. These preparations can be manufactured by mixing the compound with a physiologically acceptable known carrier, flavoring agent, excipient, vehicle, antiseptic, stabilizer, binder, etc. in a unit dosage form required in a generally accepted manner for making pharmaceutical preparations. The active ingredient in the preparation is controlled in such a dose that an appropriate dose is obtained within the specified range given.

Additives miscible with tablets or capsules include a binder such as gelatin, corn starch, tragacanth and gum arabic, an excipient such as crystalline cellulose, a swelling agent such as corn starch, gelatin and alginic acid, a lubricant such as magnesium stearate, a sweetening agent such as sucrose, lactose and saccharin, and a flavoring agent such as peppermint, akamono oil and cherry. When the unit dosage is in the form of capsules, liquid carriers such as oils and fats may further be used together with the additives described above. A sterile composition for injection may be formulated by a publicly known method used to make pharmaceutical compositions, e.g., by dissolving or suspending the active ingredients in a vehicle such as water for injection with a naturally occurring vegetable oil such as sesame oil and coconut oil, etc. to prepare the pharmaceutical composition. Examples of an aqueous medium for injection include physiological saline and an isotonic solution containing glucose and other auxiliary agents (e.g., D-sorbitol, D-mannitol and sodium chloride) and may be used in combination with an appropriate dissolution aid such as an alcohol (e.g., ethanol), a polyalcohol (e.g., propylene glycol and polyethylene glycol), a nonionic surfactant (e.g., polysorbate 80™ and HCO-50), etc. As an oily medium, for example, sesame oil and soybean oil may be used, which can be used in combination with a dissolution aid such as benzyl benzoate and benzyl alcohol.

Furthermore the prophylactic/therapeutic agent described above may also be formulated with a buffer (e.g., phosphate buffer and sodium acetate buffer) a soothing agent (e.g., benzalkonium chloride, procaine hydrochloride), a stabilizer (e.g., human serum albumin, polyethylene glycol), a preservative (e.g., benzyl alcohol, phenol), an antioxidant, etc. The thus prepared liquid for injection is normally filled in an appropriate ampoule.

Since the thus obtained preparation is safe and low toxic, it can be administered to human or mammals (e.g., rat, mouse, rabbit, sheep, swine, bovine, cat, dog, monkey, etc.).

The dose of the compound or a salt thereof (in the case of agonist) varies depending on subject to be administered, target organ, symptom, method for administration, etc.; in oral administration, the dose is normally about 0.1 to about 100 mg, preferably about 1.0 to about 50 mg, more preferably about 1.0 to about 20 mg per day for a patient with cancer (weighing 60 kg). In parenteral administration, the single dose varies depending on subject to be administered, target organ, symptom, method for administration, etc. but it is advantageous to administer the active ingredient intravenously at a daily dose of about 0.01 to about 30 mg, preferably about 0.1 to about 20 mg, more preferably about 0.1 to about 10 mg for a patient with cancer (weighing 60 kg). For other animal species, the corresponding dose as converted per 60 kg weight can be administered.

(7) Quantification of the Receptor Protein or the Like of the Present Invention or the Ligand Peptide of the Present Invention The antibody to the receptor protein or the like of the present invention or the ligand peptide of the present invention is capable of specifically recognizing the receptor protein or the like of the present invention or the ligand peptide of the present invention and accordingly, can be used for a quantification of the receptor protein or the like of the present invention or the ligand peptide of the present invention in a test sample solution, in particular, for a quantification by sandwich immunoassay. Thus, the present invention provides, for example, the following methods for quantification:

(i) a method for quantification of the receptor protein or the like of the present invention or the ligand peptide of the present invention in a test liquid sample, which comprises competitively reacting the antibody to the receptor protein or the like of the present invention or the ligand peptide of the present invention, a test liquid sample and a labeled receptor protein or the like of the present invention or a labeled ligand peptide of the present invention, and measuring the ratio of the labeled receptor protein or the like of the present invention or the labeled ligand peptide of the present invention bound to said antibody; and, (ii) a method for quantification of the receptor protein or the like of the present invention or the ligand peptide of the present invention in a test liquid sample, which comprises simultaneously or continuously reacting the test liquid sample with an antibody to the receptor protein or the like of the present invention or the ligand peptide of the present invention immobilized on an insoluble carrier and a labeled antibody to the receptor protein or the like of the present invention or the ligand peptide of the present invention, and measuring the activity of the labeling agent on the insoluble carrier.

In the method (ii) described above, it is preferred that one antibody is capable of recognizing the N-terminal region of the receptor protein or the like of the present invention or the ligand peptide of the present invention, while another antibody is capable of recognizing the C-terminal region of the receptor protein or the like of the present invention or the ligand peptide of the present invention.

The monoclonal antibody to the receptor protein or the like of the present invention or to the ligand peptide of the present invention (hereinafter sometimes referred to as the monoclonal antibody of the present invention) may be used to assay the receptor protein or the like of the present invention or the ligand peptide of the present invention. Moreover, the receptor protein or the like of the present invention or the ligand peptide of the present invention can be detected by means of a tissue staining as well. For these purposes, the antibody molecule per se may be used or $F(ab')_2$, Fab' or Fab fractions of the antibody molecule may also be used. There is no particular limitation for the assaying method using the antibody to the receptor protein or the like of the present invention or the ligand peptide of the present invention; any method may be used so far as it relates to a method in which the amount of antibody, antigen or antibody-antigen complex can be detected by a chemical or a physical means, depending on or corresponding to the amount of antigen (e.g., the amount of the receptor protein or the like of the present invention or the ligand peptide of the present invention) in a test liquid sample to be assayed, and then calculated using a standard curve prepared by a standard solution containing the known amount of antigen. Advantageously used are, for example, nephrometry, competitive method, immunometric method and sandwich method; in terms of sensitivity and specificity, the sandwich method, which will be described later, is particularly preferred.

Examples of the labeling agent used in the assay method using the labeling substance are radioisotopes, enzymes, fluorescent substances and luminescent substances, etc. Examples of the radioisotope are $[^3H]$, $[^{125}I]$, $[^{131}I]$, $[^3H]$, $[^{14}C]$, etc. Preferred examples of the enzyme are those that are stable and have a high specific activity, which include β-galactosidase, β-glucosidase, alkaline phosphatase, peroxidase and malate dehydrogenase. Examples of the fluorescent substance are fluorescamine, fluorescein isothiocyanate, etc. Examples of the luminescent substance are luminol, a luminol derivative, luciferin, lucigenin, etc. Furthermore, a biotin-avidin system may also be used for binding an antibody or antigen to a labeling agent.

In the immobilization of antigens or antibodies, physical adsorption may be used. Alternatively, chemical binding that is conventionally used for immobilization of proteins or enzymes may be used as well. Examples of the carrier include insoluble polysaccharides such as agarose, dextran and cellulose; synthetic resins such as polystyrene, polyacrylamide and silicone; glass; etc.

In the sandwich method, a test sample liquid is reacted with an immobilized monoclonal antibody of the present invention (first reaction), then reacted with a labeled monoclonal antibody of the present invention (second reaction) and the activity of the labeling agent on the insoluble carrier is assayed, whereby the amount of the receptor protein or ligand peptide of the present invention in the test sample liquid can be determined. The first and second reactions may be carried out in a reversed order, simultaneously or sequentially with an interval. The type of the labeling agent and the method for immobilization may be the same as those described hereinabove.

In the immunoassay by the sandwich method, it is not always necessary that the antibody used for the labeled antibody and for the solid phase should be one type or one species but a mixture of two or more antibodies may also be used for the purpose of improving the measurement sensitivity, etc.

In the method for assaying the receptor protein or the like of the present invention or the ligand peptide of the present invention by the sandwich method according to the present invention, preferred monoclonal antibodies of the present invention used for the first and the second reactions are antibodies, which binding sites to the receptor protein or the like of the present invention are different each other. Thus, the antibodies used in the first and the second reactions are those wherein, when the antibody used in the second reaction recognizes the C-terminal region of the receptor protein or the like, the antibody recognizing the site other than the C-terminal regions, e.g., recognizing the N-terminal region, is preferably used in the first reaction.

The monoclonal antibody to the receptor protein or the like of the present invention or the ligand peptide of the present invention may be used in an assay system other than the sandwich method, such as a competitive method, an immunometric method and a nephrometry. In the competitive method, an antigen in a test solution and a labeled antigen are competitively reacted with an antibody, then an unreacted labeled antigen (F) and a labeled antigen bound to the antibody (B) are separated (i.e., B/F separation) and the labeled amount of either B or F is measured to determine the amount of the antigen in the test solution. In the reactions for such a method, there are a liquid phase method in which a soluble antibody is used as the antibody and the B/F separation is effected by polyethylene glycol while a second antibody to the antibody is used, and a solid phase method in which an immobilized antibody is used as the first antibody or a soluble antibody is used as the first antibody while an immobilized antibody is used as the second antibody.

In the immunometric method, an antigen in a test solution and an immobilized antigen are competitively reacted with a given amount of a labeled antibody followed by separating the solid phase from the liquid phase; or an antigen in a test solution and an excess amount of labeled antibody are reacted, then an immobilized antigen is added to bind an unreacted labeled antibody to the solid phase and the solid phase is separated from the liquid phase. Thereafter, the labeled amount of any of the phases is measured to determine the antigen amount in the test solution.

In the nephrometry, the amount of insoluble sediment, which is produced as a result of the antigen-antibody reaction in a gel or in a solution, is measured. Even when the amount of an antigen in a test solution is small and only a small amount of the sediment is obtained, a laser nephrometry utilizing laser scattering can be suitably used.

In applying each of those immunoassays to the assay method for the present invention, any special conditions or operations are not required to set forth. The assay system for the receptor protein or the like of the present invention or the ligand peptide of the present invention may be constructed in addition to conditions or operations conventionally used for each of the methods, taking the technical consideration of one skilled in the art into account consideration. For the details of such conventional technical means, a variety of reviews, reference books, etc. may be referred to (for example, Hiroshi Irie (ed.): "Radioimmunoassay" (published by Kodansha, 1974); Hiroshi Irie (ed.): "Radioimmunoassay; Second Series" (published by Kodansha, 1979); Eiji Ishikawa, et al. (ed.): "Enzyme Immunoassay" (published by Igaku Shoin, 1978); Eiji Ishikawa, et al. (ed.): "Enzyme Immunoassay" (Second Edition) (published by Igaku Shoin, 1982); Eiji Ishikawa, et al. (ed.): "Enzyme Immunoassay" (Third Edition) (published by Igaku Shoin, 1987); "Methods in Enzymology" Vol. 70 (Immuochemical Techniques (Part A)); ibid., Vol. 73 (Immunochemical Techniques (Part B)); ibid., Vol. 74 (Immunochemical Techniques (Part C)); ibid., Vol. 84 (Immunochemical Techniques (Part D: Selected Immunoassays)); ibid., Vol. 92 (Immunochemical Techniques (Part E: Monoclonal Antibodies and General Immunoassay Methods)); ibid., Vol. 121 (Immunochemical Techniques (Part I: Hybridoma Technology and Monoclonal Antibodies)) (published by Academic Press); etc.)

As described above, the receptor protein or the like of the present invention or the ligand peptide of the present invention can be quantified with high sensitivity, using the antibody of the present invention.

Furthermore, the receptor protein or the like of the present invention or the ligand peptide of the present invention can be quantified with high sensitivity, using the antibody of the present invention thereby to diagnose various diseases associated with the dysfunction of the receptor protein of the present invention.

The antibody to the receptor protein or the like of the present invention or the ligand peptide of the present invention can be employed for specifically detecting the receptor protein or the like of the present invention or the ligand peptide of the present invention which may be present in a test sample solution such as a body fluid, a tissue, etc. The antibody can also be used for preparation of an antibody column for purification of the receptor protein or the like of the present invention or the ligand peptide of the present invention, detection of the receptor protein or the like of the present invention in the fractions upon purification, and analysis of the behavior of the to the receptor protein or the like of the present invention or the ligand peptide of the present invention in the cells under investigation.

(8) Neutralization with the Antibody to the Receptor Protein or the Like of the Present Invention or the Ligand Peptide of the Present Invention The activity of the antibody to the receptor protein or the like of the present invention or the ligand peptide of the present invention that neutralizes the receptor protein or the like or the ligand peptide means the activity of inactivating the function of signal transduction in which the receptor protein or the like or the ligand peptide participate. Therefore, when the antibody has the neutralizing activity, the antibody can inactivate the signal transduction in which the receptor protein or the like or the ligand peptide participate, for example, the receptor protein-mediated cell stimulating activities (e.g., the activities that promote or suppress arachidonic acid release, acetylcholine release, intracellular $Ca^{2+}$ release, intracellular cAMP production, intracellular cGMP production, inositol phosphate production, changes in cell membrane potential, phosphorylation of intracellular proteins, activation of c-fos, and pH reduction). Thus, the antibody can be used for the prevention and/or treatment of diseases caused by overexpression of the receptor protein or the ligand peptide.

(9) Preparation of Animals Containing the DNA Encoding the Receptor Protein of the Present Invention Using the DNA of the present invention, transgenic animals that express the receptor protein or the like of the present invention can be prepared. Examples of the animals are mammals (e.g., rats, mice, rabbits, sheep, swine, bovine, cats, dogs, monkeys) can be used, with particularly preferred being mice and rabbits.

To transfer the DNA of the present invention to a target animal, it is generally advantageous to use the DNA in a gene construct ligated downstream a promoter capable of expressing the DNA in an animal cell. For example, when the rabbit-derived DNA of the present invention is transferred, for example, the gene construct, in which the DNA is ligated downstream a promoter that can expresses DNA of the present invention derived from an animal which is highly homologous to the DNA of the present invention, is microinjected to rabbit fertilized ova. Thus, the DNA-transferred animal capable of producing a high level of the receptor protein or the like of the present invention can be prepared. Examples of the promoter that can be used are a virus-derived promoter and a ubiquitous expression promoter such as metallothionein may be used but an NGF gene promoter and an enolase gene promoter that are specifically expressed in the brain are used preferably.

The transfer of the DNA of the present invention at the fertilized egg cell stage secures the presence of DNA in all germ and somatic cells in the target animal. The presence of the receptor protein or the like of the present invention in the germ cells in the DNA-transferred animal means that all germ and somatic cells contain the receptor protein or the like of the present invention in all progenies of the animal. The progenies of the animal that took over the gene contain the receptor protein or the like of the present invention in all germ and somatic cells.

The transgenic animal to which the DNA of the present invention is transferred can be subjected to a mating and a breeding for generations under common breeding circumstance, as the animal carrying the DNA, after confirming that the gene can be stably retained. Moreover, male and female animals having the desired DNA are mated to give a homozygote having the transduced gene in both homologous chromosomes and then the male and female animals are mated so that such breeding for generations that progenies contain the DNA can be performed.

The transgenic animal to which the DNA of the present invention is transferred is useful as the animal for screening of the agonist or antagonist to the receptor protein or the like of the present invention, since the receptor protein or the like of the present invention is abundantly expressed.

The transgenic animal to which the DNA of the present invention is transferred can also be used as the cell sources for tissue culture. The receptor protein or the like of the present invention can be analyzed by, for example, direct analysis of the DNA or RNA in tissues of the DNA-transferred mice of the present invention, or by analysis of tissues containing the receptor protein expressed from the gene. Cells from tissues containing the receptor protein or the like of the present invention are cultured by the standard tissue culture technique. Using these cells the function of the cells from tissues that are generally difficult to culture, for example, cells derived from the brain and peripheral tissues can be studied. Using these cells it is possible to select pharmaceuticals, for example, that increase the function of various tissues. Where a highly expressing cell line is available, the receptor protein or the like of the present invention can be isolated and purified from the cell line.

In the specification and drawings, the codes of bases and amino acids are denoted in accordance with the IUPAC-IUB Commission on Biochemical Nomenclature or by the common codes in the art, examples of which are shown below. For amino acids that may have the optical isomer, L form is presented unless otherwise indicated.

DNA: deoxyribonucleic acid
cDNA: complementary deoxyribonucleic acid
A: adenine
T: thymine
G: guanine
C: cytosine
RNA: ribonucleic acid
mRNA: messenger ribonucleic acid
dATP: deoxyadenosine triphosphate
dTTP: deoxythymidine triphosphate
dGTP: deoxyguanosine triphosphate
dCTP: deoxycytidine triphosphate
ATP: adenosine triphosphate
EDTA: ethylenediaminetetraacetic acid
SDS: sodium dodecyl sulfate
Gly: glycine
Ala: alanine
Val: valine
Leu: leucine
Ile: isoleucine
Ser: serine
Thr: threonine
Cys: cysteine
Met: methionine
Glu: glutamic acid
Asp: aspartic acid
Lys: lysine
Arg: arginine
H is: histidine
Phe: phenylalanine
Tyr: tyrosine
Trp: tryptophan
Pro: proline
Asn: asparagine
Gln: glutamine
pGlu: pyroglutamic acid
Me: methyl group
Et: ethyl group
Bu: butyl group
Ph: phenyl group
TC thiazolidine-4(R)-carboxamide group Substituents, protecting groups, and reagents generally used in the specification are denoted by the codes below.
Tos: p-toluenesulfonyl
CHO: formyl
Bzl: benzyl
Cl$_2$Bzl: 2,6-dichlorobenzyl
Bom: benzyloxymethyl
Z: benzyloxycarbonyl
Cl-Z: 2-chlorobenzyloxycarbonyl
Br-Z: 2-bromobenzyloxycarbonyl
Boc: t-butoxycarbonyl
DNP: dinitrophenol
Trt: trityl
Bum: t-butoxymethyl
Fmoc: N-9-fluorenylmethoxycarbonyl
HOBt: 1-hydroxybenztriazole
HOOBt: 3,4-dihydro-3-hydroxy-4-oxo-1,2,3-benzotriazine
HONB: 1-hydroxy-5-norbornene-2,3-dicarboximide
DCC: N,N'-dichlorohexylcarbodiimide
BHA: benzhydrylamine
MeBzl: 4-methylbenzyl
OcHex: cyclohexyl ester
NMP: N-methylpyrrolidone
TFA: trifluoroacetic acid The sequence identification numbers (SEQ ID NO:) in the sequence listing of the specification indicates the following sequence, respectively.

[SEQ ID NO: 1]
The amino acid sequence of the rat cerebellum-derived novel G protein coupled receptor protein rOT7T175 of the present invention.

[SEQ ID NO: 2]
The base sequence of cDNA encoding the rat cerebellum-derived novel G protein coupled receptor protein rOT7T175 of the present invention containing the amino acid sequence shown by SEQ ID NO: 1.

[SEQ ID NO: 3]
The base sequence of primer 1 used for cloning the cDNA encoding the rat cerebellum-derived novel G protein coupled receptor protein rOT7T175 of the present invention.

[SEQ ID NO: 4]
The base sequence of primer 2 used for cloning the cDNA encoding the rat cerebellum-derived novel G protein coupled receptor protein hOT7T175 of the present invention.

[SEQ ID NO: 5]
The amino acid sequence of the human brain-derived novel G protein coupled receptor protein hOT7T175 of the present invention.

[SEQ ID NO: 6]
The base sequence of cDNA encoding the human brain-derived novel G protein coupled receptor protein hOT7T175 of the present invention containing the amino acid sequence shown by SEQ ID NO: 5.

[SEQ ID NO: 7]
The base sequence of probe used for cloning the cDNA encoding the human brain-derived novel G protein coupled receptor protein hOT7T175 of the present invention.

[SEQ ID NO: 8]
The base sequence of primer 1 used for cloning the cDNA encoding the human brain-derived novel G protein coupled receptor protein hOT7T175 of the present invention.

[SEQ ID NO: 9]
The base sequence of primer 2 used for cloning the cDNA encoding the human brain-derived novel G protein coupled receptor protein hOT7T175 of the present invention.

[SEQ ID NO: 10]
The amino acid sequence of PEPTIDE (1-54) described in Example 3.

[SEQ ID NO: 11]
The amino acid sequence of PEPTIDE (40-54) described in Example 3.

[SEQ ID NO: 12]
The amino acid sequence of PEPTIDE (45-54) described in Example 3.

[SEQ ID NO: 13]
The amino acid sequence of PEPTIDE (46-54) described in Example 3.

[SEQ ID NO: 14]
The amino acid sequence of PEPTIDE (47-54) described in Example 3.

[SEQ ID NO: 15]
The base sequence of the DNA encoding the amino acid sequence shown by SEQ ID NO: 10.

[SEQ ID NO: 16]
The base sequence of the DNA encoding the amino acid sequence shown by SEQ ID NO: 11.

[SEQ ID NO: 17]
The base sequence of the DNA encoding the amino acid sequence shown by SEQ ID NO: 12.

[SEQ ID NO: 18]
The base sequence of the DNA encoding the amino acid sequence shown by SEQ ID NO: 13.

[SEQ ID NO: 19]
The base sequence of the DNA encoding the amino acid sequence shown by SEQ ID NO: 14.

[SEQ ID NO: 20]
The amino acid sequence of KiSS-1 product described in Example 3.

[SEQ ID NO: 21]
The amino acid sequence of PEPTIDE (48-54) described in Example 3.

[SEQ ID NO: 22]
The base sequence of the DNA encoding the amino acid sequence shown by SEQ ID NO: 21.

*Escherichia coli* transformant DH10B/pAK-rOT175 obtained in Example 1 later described was on deposit with the Ministry of International Trade and Industry, Agency of Industrial Science and Technology, National Institute of Bioscience and Human Technology (NIBH) as the Accession Number FERM BP-6553 on Oct. 21, 1998 and with Institute for Fermentation, Osaka (IFO) as the Accession Number IFO 16209 on Oct. 1, 1998.

*Escherichia coli* transformant DH10B/pCMV-hOT175 obtained in Example 2 later described was on deposit with the Ministry of International Trade and Industry, Agency of Industrial Science and Technology, National Institute of Bioscience and Human Technology (NIBH) as the Accession Number FERM BP-6648 on Feb. 17, 1999 and with Institute for Fermentation, Osaka (IFO) as the Accession Number IFO 16258 on Feb. 9, 1999.

EXAMPLES

The present invention is described in detail below with reference to Examples, but not intended to limit the scope of the present invention thereto. The gene manipulation procedures using *Escherichia coli* were performed according to the methods described in the Molecular Cloning.

Example 1

Cloning of the cDNA Encoding the Rat Cerebellum-Derived G Protein Coupled Receptor Protein and Determination of the Base Sequence Using rat cerebellum cDNA as the template and two primers, namely, primer 1 (SEQ ID NO:3) and primer 2 (SEQ ID NO:4), PCR reaction was performed. The reaction solution in the above reaction comprised of 1/10 volume of the cDNA for the template, 1/50 volume of Advantage cDNA Polymerase Mix (CLONTEC Inc.), 0.2 μM primer 1 (SEQ ID NO:3), 0.2 μM primer 2 (SEQ ID NO: 4), 200 μM dNTPs and the buffer attached to the enzyme to make the final volume 50 μl. In the PCR reaction, (1) the reaction solution was heated at 94° C. for 2 minutes, (2) a cycle of heating at 94° C. for 30 seconds followed by 72° C. for 2 minutes was repeated 3 times, (3) a cycle of heating at 94° C. for 30 seconds followed by 68° C. for 2 minutes was repeated 3 times, (4) a cycle of 94° C. for 30 seconds followed by 64° C. for 30 seconds and 68° C. for 2 minutes was repeated 30 times, and (5) finally, extension reaction was performed at 68° C. for 8 minutes. After completion of the PCR reaction, the product was subcloned to plasmid vector pCR2.1 (Invitrogen Inc.) following the instructions attached to TA cloning kit (Invitrogen Inc.), which was then introduced into *Escherichia coli* DH5α, and the clones containing the cDNA were selected on LB agar plates containing ampicillin. The sequence of each clone was analyzed to give the cDNA sequence (SEQ ID NO:2) encoding the novel G protein coupled receptor protein. The novel G protein coupled receptor protein containing the amino acid sequence (SEQ ID NO:1) deduced from the cDNA was designated rOT7T175.

Plasmid pAK-rOT7T175 in which the cDNA (SEQ ID NO: 2) encoding the rat cerebellum-derived G protein coupled receptor protein rOT7T175 of the present invention was subcloned was introduced into *Escherichia coli* DH10B according to a publicly known method to give the transformant *Escherichia coli* DH10B/pAK-rOT175.

Example 2

Cloning of cDNA Encoding Human Brain-Derived Novel G Protein Coupled Receptor Protein hOT7T175 and Determination of the Base Sequence Cloning of cDNA was performed following the protocol of GENE TRAPPER (Life Technologies, Inc.). After biotinylation of probe (SEQ ID NO: 7), the probe was hybridized with single-stranded human brain cDNA library (Superscript cDNA Library, Life Technologies, Inc.). The thus obtained single-stranded gene was converted into the double strand using primer 1 (SEQ ID NO: 8). After the gene was introduced into *Escherichia coli* DH10B by the electroporation, the gene was grown on a selection plate supplemented with ampicillin to obtain transformants. The electroporation was conducted at a voltage of 1.8 kV using *E. coli* Pulser (BIO-RAD, Inc.). The thus obtained transformants were selected by colony PCR using probe (SEQ ID NO: 7) and primer 2 (SEQ ID NO: 9) to obtain the transformant *E. coli* DH10B/pCMF-hOT175. The novel G protein coupled receptor protein containing the amino acid sequence (SEQ ID NO: 5) deduced from the cDNA was denoted hOT7T175. In the colony PCR, the reaction solution comprised of 1/50 volume of Advantage cDNA Polymerase Mix (CLONTEC Inc.), 0.2 μM primer 1 (SEQ ID NO: 7), 0.2 μM primer 2 (SEQ ID NO:9), 200 μM dNTPs, 1/25 volume of DMSO and the buffer attached to the enzyme to make the final volume 10 μl. In the PCR reaction, (1) the reaction solution was heated at 94° C. for 10 minutes and (2) a cycle of heating at 94° C. for 10 seconds followed by 60° C. for 10 seconds and 68° C. for 1 minute was repeated 25 times. After completion of the PCR reaction, the product was subcloned to plasmid vector pCR2.1 (Invitrogen Inc.) following the instructions attached to TA cloning kit (Invitrogen Inc.), which was then introduced into *Escherichia coli* DH10B. The clones containing the cDNA were then selected on LB agar medium containing ampicillin. The sequence of each clone was analyzed to give the cDNA sequence (SEQ ID NO:6) encoding the novel G protein coupled receptor protein. The novel G protein coupled receptor protein containing the amino acid sequence (SEQ ID NO:5) deduced from the cDNA was designated hOT175.

Example 3

Screening of Peptide Activating rOT7175 (Orphan Receptor)

(1-1) Peptide Synthesis

Peptide having the sequence (SEQ ID NO: 10) of 54 amino acid residues from 68 (Gly) to 121 (Phe) in the cancer metastasis-suppressing gene (KiSS-1) product (SEQ ID NO: 20) found in the gene database can be synthesized by the following procedure (wherein the peptide is hereinafter referred to as PEPTIDE (1-54).

Furthermore, the C-terminal peptides of PEPTIDE (1-54) (SEQ ID NO: 10), namely, PEPTIDE (40-54) (SEQ ID NO: 11), PEPTIDE (45-54) (SEQ ID NO: 12), PEPTIDE (46-54) (SEQ ID NO: 13), PEPTIDE (47-54) (SEQ ID NO: 14) and PEPTIDE (48-54) (SEQ ID NO: 21) were synthesized by the following procedure.

(1) Preparation of PEPTIDE (40-54)

Commercially available p-methyl BHA resin (0.77 mmole/g resin) was charged in a reaction tank of peptide synthesizer ABI 430A. Thereafter, Boc-Phe, Boc-Arg(Tos), Boc-Leu, Boc-Gly, Boc-Phe, Boc-Ser(Bzl), Boc-Asn, Boc-Trp(CHO), Boc-Asn, Boc-Tyr(Br-Z), Boc-Asn, Boc-Pro, Boc-Leu, Boc-Asp(OcHex) and Boc-Lys(Cl-z) were introduced into the resin in this order according to the Boc-strategy (NMP-HOBt) peptide synthesis to give the desired protected peptide resin. The resin, 0.12 g, was stirred at 0° C. for 60 minutes in 10 ml of anhydrous hydrogen fluoride containing 1 ml of p-cresol and 1.2 ml of 1,4-butanediol. Thereafter the hydrogen fluoride was distilled off in vacuum. Diethyl ether was added to the residue and the precipitate was filtrated. 50% acetic acid aqueous solution was added to the precipitate for extraction and insoluble matters were removed. After the extract was sufficiently concentrated, the concentrate was applied to Sephadex (trade name) G-25 column (2.0×80 cm) filled with 50% acetic acid aqueous solution followed by development with the same solvent. The main fractions were collected and lyophilized to give 40 mg of white powders. A half volume of the powders was applied to reverse phase chromatography column (2.6×60 cm) packed with LiChroprep (trade name) RP-18 followed by washing with 200 ml of water containing 0.1% TFA. Then linear density gradient elution was performed with 300 ml of 0.1% TFA and 300 ml of 0.1% TFA-containing 33% acetonitrile. The main fractions were collected and lyophilized to give 4.1 mg of the desired peptide.

Mass spectrum $(M+H)^+$ 1869.9 (calcd. 1969.9)
Elution time on HPLC: 18.6 mins.

Column conditions:
Column: Wakosil 5C18T, 4.6×100 mm
Eluant: linear density gradient elution with eluants A/B=95/5-45/55, using aqueous 0.1% TFA as eluant A and acetonitrile containing 0.1% TFA (25 mins.)
Flow rate: 1.0 ml/min.

(2) Preparation of PEPTIDE (45-54)

Commercially available p-methyl BHA resin (0.77 mmole/g resin) was charged in a reaction tank of peptide synthesizer ABI 430A. Then, Boc-Phe, Boc-Arg(TOS), Boc-Leu, Boc-Gly, Boc-Phe, Boc-Ser(Bzl), Boc-Asn, Boc-Trp (CHO), Boc-Asn and Boc-Tyr(Br-Z) were introduced into the resin in this order according to the Boc-strategy (NMP-HOBt) peptide synthesis to give the desired protected peptide resin. The resin, 0.11 g, was treated in a manner similar to the procedure (1) above for removing the protecting groups to give 2.2 mg of the desired peptide.

Mass spectrum $(M+H)^+$ 1302.5 (calcd. 1302.6)
Elution time on HPLC: 18.7 mins.

Column conditions:
Column: Wakosil 5C18T, 4.6×100 mm
Eluant: linear density gradient elution with eluants A/B=95/5-45/55, using aqueous 0.1% TFA as eluant A and acetonitrile containing 0.1% TFA (25 mins.)
Flow rate: 1.0 ml/min.

(3) Preparation of PEPTIDE (46-54)

Commercially available p-methyl BHA resin (0.77 mmole/g resin) was charged in a reaction tank of peptide synthesizer ABI 430A. Then, Boc-Phe, Boc-Arg(Tos),Boc-Leu, Boc-Gly, Boc-Phe, Boc-Ser(Bzl), Boc-Asn, Boc-Trp (CHO) and Boc-Asn were introduced in this order according to the Boc-strategy (NMP-HOBt) peptide synthesis to give the desired protected peptide resin. The resin, 0.11 g, was treated in a manner similar to the aforesaid procedure (1) for removing the protecting groups to give 3.4 mg of the desired peptide.

Mass spectrum $(M+H)^+$ 1139.6 (calcd. 1139.6)
Elution time on HPLC: 18.1 mins.

Column conditions:
Column: Wakosil 5C18T, 4.6×100 mm
Eluant: linear density gradient elution with eluants A/B=95/5-45/55, using aqueous 0.1% TFA as eluant A and acetonitrile containing 0.1% TFA (25 mins.)
Flow rate: 1.0 ml/min.

(4) Preparation of PEPTIDE (47-54)

Commercially available p-methyl BHA resin (0.77 mmole/g resin) was charged in a reaction tank of peptide synthesizer ABI 430A. Then, Boc-Phe, Boc-Arg(Tos), Boc-Leu, Boc-Gly, Boc-Phe, Boc-Ser(Bzl), Boc-Asn and Boc-Trp (CHO) were introduced in this order according to the Boc-strategy (NMP-HOBt) peptide synthesis to give the desired protected peptide resin. The resin, 0.12 g, was treated in a manner similar to the aforesaid procedure (1) for removing the protecting groups to give 13.0 mg of the desired peptide.

Mass spectrum $(M+H)^+$ 1025.5 (calcd. 1025.5)
Elution time on HPLC: 17.6 mins.

Column conditions:
Column: Wakosil 5C18T, 4.6×100 mm
Eluant: linear density gradient elution with eluants A/B=95/5-45/55, using aqueous 0.1% TFA as eluant A and acetonitrile containing 0.1% TFA (25 mins.)
Flow rate: 1.0 ml/min.

(5) Preparation of PEPTIDE (48-54)

Commercially available p-methyl BHA resin (0.77 mmole/g resin) was charged in a reaction tank of peptide synthesizer ABI 430A. Then, Boc-Phe, Boc-Arg(Tos), Boc-Leu, Boc-Gly, Boc-Phe, Boc-Ser(Bzl) and Boc-Asn were introduced in this order according to the Boc-strategy (NMP-HOBt) peptide synthesis to give the desired protected peptide resin. The resin, 0.16 g, was stirred in 10 ml of anhydrous hydrogen fluoride together with 1 ml of p-cresol at 0° C. for 60 minutes. The reaction mixture was then treated in a manner similar to the aforesaid procedure (1) to give 29.0 mg of the desired peptide.

Mass spectrum $(M+H)^+$ 839.5 (calcd. 839.5)
Elution time on HPLC: 15.6 mins.

Column conditions:
Column: wakosil 5C18T, 4.6×100 mm
Eluant: linear density gradient elution with eluants A/B=95/5-45/55, using aqueous 0.1% TFA as eluant A and acetonitrile containing 0.1% TFA (25 mins.)
Flow rate: 1.0 ml/min.

(6) Preparation of PEPTIDE (1-54)

PEPTIDE (1-54) can be prepared by charging commercially available p-methyl BHA resin (0.77 mmole/g resin) in a reaction tank of peptide synthesizer ABI 430A, introducing, in the following order, Boc-Phe, Boc-Arg(Tos), Boc-Leu, Boc-Gly, Boc-Phe, Boc-Ser(Bzl), Boc-Asn, Boc-Trp(CHO), Boc-Asn, Boc-Tyr(Br-Z), Boc-Asn, Boc-Pro, Boc-Leu, Boc-Asp(OcHex), Boc-Lys(Cl-Z), Boc-Glu(OcHex),Boc-Arg (Tos). Boc-Gln, Boc-Val, Boc-Leu, Boc-Val, Boc-Ala, Boc-Gly, Boc-Gln, Boc-Pro, Boc-Ala, Boc-Pro, Boc-Ile, Boc-Gln, Boc-Arg(Tos), Boc-Ser(Bzl), Boc-His(Bom), Boc-Pro, Boc-Ala, Boc-Ser(Bzl), Boc-Leu, Boc-Gly, Boc-Pro, Boc-Gln, Boc-Gln, Boc-Arg(Tos), Boc-Ser(Bzl), Boc-Gly, Boc-Ser(Bzl), Boc-Ser(Bzl), Boc-Glu(OcHex), Boc-Pro, Boc-Pro, Boc-Pro, Boc-Ser(Bzl), Boc-Leu, Boc-Ser(Bzl), Boc-Thr(Bzl) and Boc-Gly to obtain the desired protected peptide resin and then removing the protecting groups from the protected peptide resin, as in (1) of the method for preparing PEPTIDE (40-54) above.

(1-2) Measurement of Intracellular Ca Ion Concentration-Increasing Activity using FLIPR The stable expression cell line rOT7T175 was obtained by transduction of expression plasmid PAK-rOT175 for animal cell into CHO/dhfr⁻ cells, using CellPhect Transfection Kit (Amersham Pharmacia Biotech, Inc.). First, 240 ml of Buffer A (attached to CellPhect Transfection Kit) was added to 9.6 mg of plasmid DNA dissolved in 240 ml of distilled water followed by stirring. After the mixture was settled for 10 minutes, 480 ml of Buffer B (attached to CellPhect Transfection Kit) was added to the mixture, which was vigorously stirred to form liposomes containing the DNA. Then $4 \times 10^5$ CHO/dhfr⁻ cells (obtained from ATCC) were inoculated on a 60 mm Petri dish. After culturing the cells in Ham's F-12 medium (Nissui Seiyaku Co., Ltd.) supplemented with 10% fetal bovine serum (BIO WHITTAKER, Inc.) at 37° C. for 2 days in 5% carbon dioxide gas, 480 ml of the liposomes were dropwise added to the cells in the Petri dish. After culturing the cells at 37° C. for 6 hours in 5% carbon dioxide gas, the cells were washed twice with serum-free Ham's F-12 medium and 3 ml of 15% glycerol was added to the cells in the Petri dish followed by treatment for 2 minutes. The cells were again washed twice with serum-free Ham's F-12 medium followed by incubation in Ham's F-12 medium supplemented with 10% fetal bovine serum at 37° C. for 15 hours in 5% carbon dioxide gas. The cells were dispersed by trypsin treatment to recover from the Petri dish. The recovered cells were inoculated on a 6-well plate in $1.25 \times 10^4$ cells/well and began to incubate at 37° C. for 15 hours in Dulbecco's modified Eagle medium (DMEM) medium (Nissui Seiyaku Co., Ltd.) containing 10% dialyzed fetal bovine serum (JRH BIO-SCIENCE, Inc.) in 5% carbon dioxide gas. The plasmid-transduced transformants of CHO cells grew in the medium but the non-transduced cells gradually died. The medium was exchanged on Days 1 and 2 to remove the cells died. Approximately 20 colonies of the transformants of CHO cells that kept growing on Days 8 to 10 after the incubation were selected. DNA was recovered from the selected cells, respectively, using a commercially available kit for isolation of RNA. By applying the publicly known RT-PCR method to the following steps, the 23rd clone of rOT7T175 expressing CHO cells (hereinafter abbreviated as rOT7T175-23) that expresses rOT7T175 receptor gene in a high level was selected.

For control, the 24th clone of ETA expressing CHO cells (hereinafter abbreviated as ETA24; see Journal of Pharmacology and Experimental Therapeutics, vol. 279, pp. 675-685, 1996) was employed.

The intracellular Ca ion concentration-increasing activity of the synthetic peptides obtained in (1-1) described above in rOT7T175-23 and ETA24 was determined, using FLIPR (Molecular Devices, Inc.).

Both rOT7T175-23 cells and ETA24 cells were used after subculturing these cells in DMEM supplemented with 10% dialyzed fetal bovine serum (hereinafter abbreviated as dFBS). The rOT7T175-23 and ETA24 cells were suspended in a medium (10% dFBS-DMEM), respectively, in $15 \times 10^4$ cells/ml. Each 200 µl ($3.0 \times 10^4$ cells/200 µl) of the suspension was inoculated on a 96-well plate for FLIPR (black plate clear bottom, Coster, Inc.) through a dispenser, followed by incubation at 37° C. overnight in a 5% $CO_2$ incubator. The cells thus incubated were used (hereinafter referred to as cell plate). Then, 21 ml of HANKS/HBSS (9.8 g of HANKS', 0.35 g of sodium hydrogencarbonate, 20 ml of 1M HEPES; after adjusting the pH to 7.4 with 1N sodium hydroxide, the mixture was subjected to sterilization through a filter), 210 µl of 250 mM Probenecid and 210 µl of fetal bovine serum (FBS) were mixed (HANKS/HBSS-Probenecid-FBS). Furthermore, 2 vials of Fluo3-AM (50 µg/vial) were dissolved in 42 µl of dimethylsulfoxide and 42 µl of 20% Pluronic acid. The resulting solution was added to 20 ml of HANKS/HBSS-Probenecid-FBS described above and then mixed. After the culture solution was removed, 100 µl each/well of the mixture was dispensed to the cell plate using an eight-stranded pipette followed by incubation at 37° C. for an hour in a 5% $CO_2$ incubator (pigment loading). The peptide was dissolved in dimethylsulfoxide in $1 \times 10^{-3}$ M. To 0.002 ml ($1 \times 10^{-3}$ M) of the peptide solution in dimethylsulfoxide, 0.066 ml of HANKS'/HBSS containing 2.5 mM Probenecid and 0.2% BSA was added for dilution (final concentration of $1 \times 10^{-5}$ M at the activity assay). Thereafter, 0.009 ml of dimethylsulfoxide was added to 0.001 ml ($1 \times 10^{-3}$ M) of the peptide solution in dimethylsulfoxide for dilution. After dispensing 0.002 ml of the dilution, 0.066 ml of HANKS'/HBSS containing 2.5 mM Probenecid and 0.2% BSA was added to the system for dilution (final concentration of $1 \times 10^{-6}$ M). Likewise, dilution was continued to the final concentration of $1 \times 10^{-10}$ M and then transferred to a 96-well plate for FLIPR (V-Bottom plate, Coster, Inc.)(hereinafter referred to as a sample plate). After completion of the pigment loading onto the cell plate, the cell plate was washed 4 times with a washing buffer, which was obtained by adding 2.5 mM Probenecid to HANKS'/HBSS, using a plate washer to leave 100 µl of washing buffer after the washing. The cell plate and the sample plate were set in FLIPR and 0.05 ml of a sample from the sample plate was automatically transferred to the cell plate with the FLIPR device to promote the cell response. A change in intracellular calcium ion concentration for 180 seconds was measured with passage of time.

Figure 9:
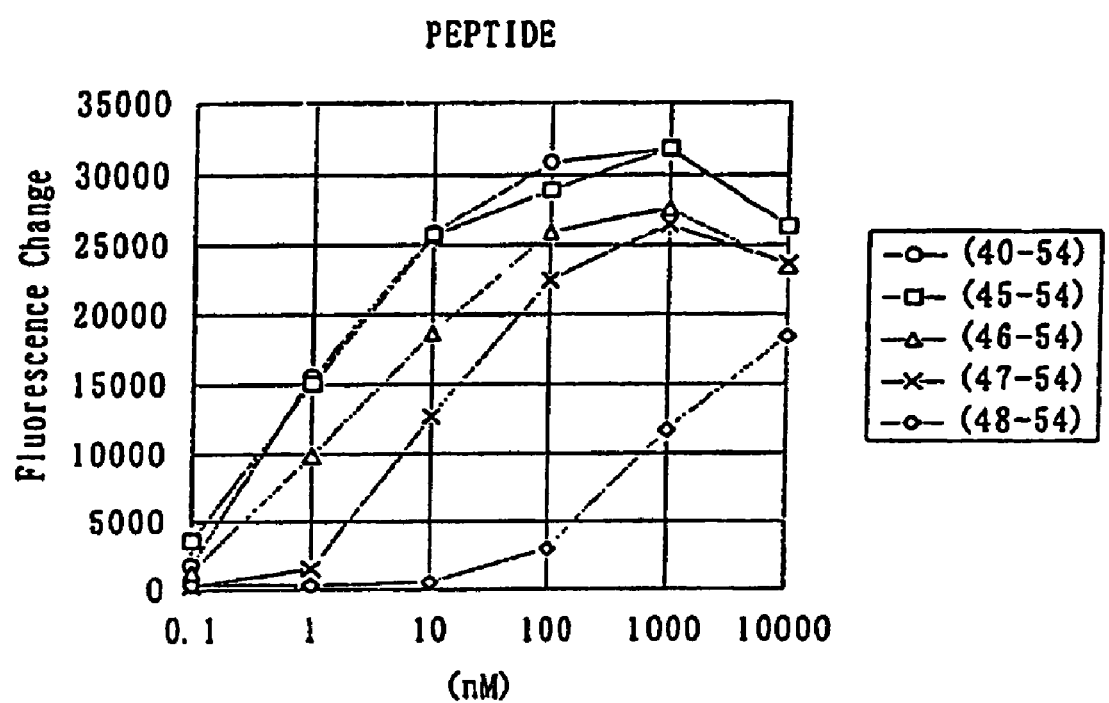
FIG. 9 shows the measurement results of intracellular Ca ion level-increasing activity tested in Example 3 (1-2).

The results reveal that the peptides synthesized in (1-1) described above induced an increase in the intracellular calcium ion concentration specifically to the rOT7T175 expressing cells. By comparison of dose response curves (FIG. 9), it is clear that PEPTIDE (40-54) and PEPTIDE (45-54) exhibit the highest activity.

INDUSTRIAL APPLICABILITY

The G protein coupled receptor protein of the present invention, its partial peptide or salts thereof as well as the polynucleotide coding for the same (e.g., DNA, RNA and derivatives thereof) can be used: (1) for determination of the ligand (ligand peptide of the present invention)(agonist), (2) for preparing antibodies and antisera thereto, (3) for construction of the expression system of a recombinant receptor protein, (4) for development of the receptor-binding assay system using the expression system and screening of a candidate pharmaceutical compound, (5) for drug design based on comparison with structurally similar ligand-receptor, (6) as a reagent for preparing a probe or a PCR primer in gene diagnostic, (7) for preparing a transgenic animal, or (8) as a prophylactic/therapeutic agent in gene therapy.

The invention claimed is:

1. A method for screening a compound or a salt thereof that alters the binding between a ligand and a protein, said method comprises:
   contacting a protein with a ligand in the presence of a test compound, and
   comparing the binding between said ligand and said protein to a control sample lacking the test compound and selecting the compound that alters said binding as compared to the control sample, wherein said protein is selected from the group consisting of:
   (i) the protein comprising the amino acid sequence of SEQ ID NO: 5;
   (ii) the protein encoded by the nucleic acid sequence of SEQ ID NO: 6; and
   (iii) the protein encoded by the nucleic acid sequence at least 95% homologous to SEQ ID NO: 6.

* * * * *

SEQUENCE LISTING

<160> NUMBER OF SEQ ID NOS: 22

<210> SEQ ID NO 1
<211> LENGTH: 396
<212> TYPE: PRT
<213> ORGANISM: Rat

<400> SEQUENCE: 1

```
Met Ala Ala Glu Ala Thr Leu Gly Pro Asn Val Ser Trp Trp Ala Pro
                 5                  10                  15

Ser Asn Ala Ser Gly Cys Pro Gly Cys Gly Val Asn Ala Ser Asp Gly
             20                  25                  30

Pro Gly Ser Ala Pro Arg Pro Leu Asp Ala Trp Leu Val Pro Leu Phe
         35                  40                  45

Phe Ala Ala Leu Met Leu Leu Gly Leu Val Gly Asn Ser Leu Val Ile
     50                  55                  60

Phe Val Ile Cys Arg His Lys His Met Gln Thr Val Thr Asn Phe Tyr
 65                  70                  75                  80

Ile Ala Asn Leu Ala Ala Thr Asp Val Thr Phe Leu Leu Cys Cys Val
                 85                  90                  95

Pro Phe Thr Ala Leu Leu Tyr Pro Leu Pro Thr Trp Val Leu Gly Asp
            100                 105                 110

Phe Met Cys Lys Phe Val Asn Tyr Ile Gln Gln Val Ser Val Gln Ala
        115                 120                 125

Thr Cys Ala Thr Leu Thr Ala Met Ser Val Asp Arg Trp Tyr Val Thr
    130                 135                 140

Val Phe Pro Leu Arg Ala Leu His Arg Arg Thr Pro Arg Leu Ala Leu
145                 150                 155                 160

Thr Val Ser Leu Ser Ile Trp Val Gly Ser Ala Ala Val Ser Ala Pro
                165                 170                 175

Val Leu Ala Leu His Arg Leu Ser Pro Gly Pro His Thr Tyr Cys Ser
            180                 185                 190

Glu Ala Phe Pro Ser Arg Ala Leu Glu Arg Ala Phe Ala Leu Tyr Asn
        195                 200                 205

Leu Leu Ala Leu Tyr Leu Leu Pro Leu Leu Ala Thr Cys Ala Cys Tyr
    210                 215                 220

Gly Ala Met Leu Arg His Leu Gly Arg Ala Ala Val Arg Pro Ala Pro
225                 230                 235                 240

Thr Asp Gly Ala Leu Gln Gly Gln Leu Leu Ala Gln Arg Ala Gly Ala
                245                 250                 255

Val Arg Thr Lys Val Ser Arg Leu Val Ala Ala Val Val Leu Leu Phe
            260                 265                 270

Ala Ala Cys Trp Gly Pro Ile Gln Leu Phe Leu Val Leu Gln Ala Leu
        275                 280                 285

Gly Pro Ser Gly Ala Trp His Pro Arg Ser Tyr Ala Ala Tyr Ala Leu
    290                 295                 300

Lys Ile Trp Ala His Cys Met Ser Tyr Ser Asn Ser Ala Leu Asn Pro
305                 310                 315                 320

Leu Leu Tyr Ala Phe Leu Gly Ser His Phe Arg Gln Ala Phe Cys Arg
                325                 330                 335

Val Cys Pro Cys Gly Pro Gln Arg Gln Arg Arg Pro His Ala Ser Ala
            340                 345                 350

His Ser Asp Arg Ala Ala Pro His Ser Val Pro His Ser Arg Ala Ala
        355                 360                 365

His Pro Val Arg Val Arg Thr Pro Glu Pro Gly Asn Pro Val Val Arg
    370                 375                 380

Ser Pro Ser Val Gln Asp Glu His Thr Ala Pro Leu
385                 390                 395

<210> SEQ ID NO 2
<211> LENGTH: 1191
```

```
<212> TYPE: DNA
<213> ORGANISM: Rat

<400> SEQUENCE: 2
atggccgcag aggcgacgtt gggtccgaac gtgagctggt gggctccgtc caacgcttcg      60
ggatgcccgg gctgcggtgt caatgcctcg gatgcccag gctccgcgcc aaggcccctg     120
gatgcctggc tggtgcccct gttttcgct gccctaatgt tgctggggct agtcgggaac     180
tcactggtca tcttcgttat ctgccgccac aagcacatgc agaccgtcac caatttctac     240
atcgctaacc tggcggccac agatgtcact tccttctgt gctgcgtacc cttcaccgcg     300
ctcctctatc cgctgcccac ctgggtgctg ggagacttca tgtgcaaatt cgtcaactac     360
atccagcagg tctcggtgca agccacatgt gccactttga cagccatgag tgtggaccgc     420
tggtacgtga ctgtgttccc gctgcgtgca cttcaccgcc gcactccgcg cctggccctg     480
actgtcagcc ttagcatctg ggtgggttcc gcagctgttt ccgccccggt gctggctctg     540
caccgcctgt cgcccgggcc tcacacctac tgcagtgagg cgtttcccag ccgtgccctg     600
gagcgcgctt tcgcgctcta caacctgctg gccctatacc tgctgccgct gctcgccacc     660
tgcgcctgct acggtgccat gctgcgccac ctgggccgcg ccgctgtacg ccccgcaccc     720
actgatggcg ccctgcaggg gcagctgcta gcacagcgcg ctggagcagt gcgcaccaag     780
gtctcccggc tggtggccgc tgtcgtcctg ctcttcgccg cctgctgggg cccgatccag     840
ctgttcctgg tgcttcaagc cctgggcccc tcggggggcct ggcacccctg aagctatgcc     900
gcctacgcgc tcaagatctg gctcactgc atgtcctaca gcaattctgc gctcaacccg     960
ctgctctatg ccttcctggg ttcccacttc agacaggcct tctgccgcgt gtgcccctgc    1020
ggcccgcaac gccagcgtcg gccccacgcg tcagcgcact cggaccgagc cgcaccccat    1080
agtgtgccgc acagccgggc tgcgcaccct gtccgggtca ggaccccga gcctgggaac    1140 cctgtggtgc gctcgccctc tgttcaggat gaacacactg ccccactctg a            1191

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 3
gtcgacatgg ccgcagaggc gacgttgggt                                       30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 4
actagttcag agtggggcag tgtgttcatc                                       30

<210> SEQ ID NO 5
<211> LENGTH: 398
<212> TYPE: PRT
<213> ORGANISM: Human

<400> SEQUENCE: 5

Met His Thr Val Ala Thr Ser Gly Pro Asn Ala Ser Trp Gly Ala Pro
             5                  10                  15
```

```
Ala Asn Ala Ser Gly Cys Pro Gly Cys Gly Ala Asn Ala Ser Asp Gly
            20                  25                  30

Pro Val Pro Ser Pro Arg Ala Val Asp Ala Trp Leu Val Pro Leu Phe
            35                  40                  45

Phe Ala Ala Leu Met Leu Leu Gly Leu Val Gly Asn Ser Leu Val Ile
     50                  55                  60

Tyr Val Ile Cys Arg His Lys Pro Met Arg Thr Val Thr Asn Phe Tyr
 65                  70                  75                  80

Ile Ala Asn Leu Ala Ala Thr Asp Val Thr Phe Leu Leu Cys Cys Val
                85                  90                  95

Pro Phe Thr Ala Leu Leu Tyr Pro Leu Pro Gly Trp Val Leu Gly Asp
            100                 105                 110

Phe Met Cys Lys Phe Val Asn Tyr Ile Gln Gln Val Ser Val Gln Ala
            115                 120                 125

Thr Cys Ala Thr Leu Thr Ala Met Ser Val Asp Arg Trp Tyr Val Thr
    130                 135                 140

Val Phe Pro Leu Arg Ala Leu His Arg Arg Thr Pro Arg Leu Ala Leu
145                 150                 155                 160

Ala Val Ser Leu Ser Ile Trp Val Gly Ser Ala Ala Val Ser Ala Pro
                165                 170                 175

Val Leu Ala Leu His Arg Leu Ser Pro Gly Pro Arg Ala Tyr Cys Ser
            180                 185                 190

Glu Ala Phe Pro Ser Arg Ala Leu Glu Arg Ala Phe Ala Leu Tyr Asn
            195                 200                 205

Leu Leu Ala Leu Tyr Leu Leu Pro Leu Leu Ala Thr Cys Ala Cys Tyr
    210                 215                 220

Ala Ala Met Leu Arg His Leu Gly Arg Val Ala Val Arg Pro Ala Pro
225                 230                 235                 240

Ala Asp Ser Ala Leu Gln Gly Gln Val Leu Ala Glu Arg Ala Gly Ala
                245                 250                 255

Val Arg Ala Lys Val Ser Arg Leu Val Ala Val Val Leu Leu Phe
            260                 265                 270

Ala Ala Cys Trp Gly Pro Ile Gln Leu Phe Leu Val Leu Gln Ala Leu
    275                 280                 285

Gly Pro Ala Gly Ser Trp His Pro Arg Ser Tyr Ala Ala Tyr Ala Leu
    290                 295                 300

Lys Thr Trp Ala His Cys Met Ser Tyr Ser Asn Ser Ala Leu Asn Pro
305                 310                 315                 320

Leu Leu Tyr Ala Phe Leu Gly Ser His Phe Arg Gln Ala Phe Arg Arg
                325                 330                 335

Val Cys Pro Cys Ala Pro Arg Arg Pro Arg Arg Pro Arg Arg Pro Gly
            340                 345                 350

Pro Ser Asp Pro Ala Ala Pro His Ala Glu Leu His Arg Leu Gly Ser
            355                 360                 365

His Pro Ala Pro Ala Arg Ala Gln Lys Pro Gly Ser Ser Gly Leu Ala
    370                 375                 380

Ala Arg Gly Leu Cys Val Leu Gly Glu Asp Asn Ala Pro Leu
385                 390                 395

<210> SEQ ID NO 6
<211> LENGTH: 1197
<212> TYPE: DNA
<213> ORGANISM: Human
```

-continued

```
<400> SEQUENCE: 6
atgcacaccg tggctacgtc cggacccaac gcgtcctggg gggcaccggc caacgcctcc      60
ggctgcccgg gctgtggcgc caacgcctcg gacggcccag tcccttcgcc gcgggccgtg     120
gacgcctggc tcgtgccgct cttcttcgcg gcgctgatgc tgctgggcct ggtggggaac     180
tcgctggtca tctacgtcat ctgccgccac aagccgatgc ggaccgtgac caacttctac     240
atcgccaacc tggcggccac ggacgtgacc ttcctcctgt gctgcgtccc cttcacggcc     300
ctgctgtacc cgctgccggg ctgggtgctg ggcgacttca tgtgcaagtt cgtcaactac     360
atccagcagg tctcggtgca ggccacgtgt gccactctga ccgccatgag tgtggaccgc     420
tggtacgtga cggtgttccc gttgcgcgcc ctgcaccgcc gcacgccccg cctggcgctg     480
gctgtcagcc tcagcatctg ggtaggctct cggcggtgt ctgcgccggt gctcgccctg     540
caccgcctgt cacccgggcc gcgcgcctac tgcagtgagg ccttccccag ccgcgccctg     600
gagcgcgcct cgcactgta caacctgctg gcgctgtacc tgctgccgct gctcgccacc     660
tgcgcctgct atgcggccat gctgcgccac ctgggccggg tcgccgtgcg ccccgcgccc     720
gccgatagcg ccctgcaggg gcaggtgctg cagagcgcg caggcgccgt gcgggccaag     780
gtctcgcggc tggtggcggc cgtggtcctg ctcttcgccg cctgctgggg ccccatccag     840
ctgttcctgg tgctgcaggc gctgggcccc gcgggctcct ggcacccacg cagctacgcc     900
gcctacgcgc ttaagacctg ggctcactgc atgtcctaca gcaactccgc gctgaacccg     960
ctgctctacg ccttcctggg ctcgcacttc gacaggcct tccgccgcgt ctgcccctgc    1020
gcgccgcgcc gcccccgccg ccccgccgg cccggaccct cggacccgc agccccacac    1080 gcggagctgc accgcctggg gtcccacccg gccccgccca gggcgcagaa gccagggagc    1140
agtgggctgg ccgcgcgcgg gctgtgcgtc ctggggagg acaacgcccc tctctga       1197

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Probe

<400> SEQUENCE: 7
gaccgtgacc aacttctaca tcgcca                                           26

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 8
atgcacaccg tggctacgtc cg                                               22

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 9
cctgtcggaa gtgcgagccc a                                                21
```

```
<210> SEQ ID NO 10
<211> LENGTH: 54
<212> TYPE: PRT
<213> ORGANISM: Artificial Sequence
<220> FEATURE:
<223> OTHER INFORMATION: Description of Artificial Sequence: the
      C-terminus of the polypeptide is amide (-CONH2)form

<400> SEQUENCE: 10

Gly Thr Ser Leu Ser Pro Pro Glu Ser Ser Gly Ser Arg Gln Gln
1               5                   10                  15

Pro Gly Leu Ser Ala Pro His Ser Arg Gln Ile Pro Ala Pro Gln Gly
            20                  25                  30

Ala Val Leu Val Gln Arg Glu Lys Asp Leu Pro Asn Tyr Asn Trp Asn
        35                  40                  45

Ser Phe Gly Leu Arg Phe
    50

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: the
      C-terminus of the polypeptide is amide (-CONH2)form

<400> SEQUENCE: 11

Lys Asp Leu Pro Asn Tyr Asn Trp Asn Ser Phe Gly Leu Arg Phe
1               5                   10                  15

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: the
      C-terminus of the polypeptide is amide (-CONH2)form

<400> SEQUENCE: 12

Tyr Asn Trp Asn Ser Phe Gly Leu Arg Phe
1               5                   10

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: the
      C-terminus of the polypeptide is amide (-CONH2)form

<400> SEQUENCE: 13

Asn Trp Asn Ser Phe Gly Leu Arg Phe
1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: the
      C-terminus of the polypeptide is amide (-CONH2)form

<400> SEQUENCE: 14

Trp Asn Ser Phe Gly Leu Arg Phe
1               5
```

<210> SEQ ID NO 15
<211> LENGTH: 162
<212> TYPE: DNA
<213> ORGANISM: Artificial Sequence
<220> FEATURE:
<223> OTHER INFORMATION: Description of Artificial Sequence: the DNA
      encoding the amino acid sequence shown by SEQ ID NO: 10

<400> SEQUENCE: 15
gggacctcgc tgtccccgcc ccccgagagc tccgggagcc gccagcagcc gggcctgtcc      60 gcccccaca gccgccagat ccccgcaccc cagggcgcgg tgctggtgca gcgggagaag     120
gacctgccga actacaactg gaactccttc ggcctgcgct tc                        162

<210> SEQ ID NO 16
<211> LENGTH: 45
<212> TYPE: DNA
<213> ORGANISM: Artificial Sequence
<220> FEATURE:
<223> OTHER INFORMATION: Description of Artificial Sequence: the DNA
      encoding the amino acid sequence shown by SEQ ID NO: 11

<400> SEQUENCE: 16
aaggacctgc cgaactacaa ctggaactcc ttcggcctgc gcttc                      45

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: the DNA
      encoding the amino acid sequence shown by SEQ ID NO: 12

<400> SEQUENCE: 17
tacaactgga actccttcgg cctgcgcttc                                       30

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: the DNA
      encoding the amino acid sequence shown by SEQ ID NO: 13

<400> SEQUENCE: 18
aactggaact ccttcggcct gcgcttc                                          27

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: the DNA
      encoding the amino acid sequence shown by SEQ ID NO: 14

<400> SEQUENCE: 19
tggaactcct tcggcctgcg cttc                                             24

<210> SEQ ID NO 20
<211> LENGTH: 145
<212> TYPE: PRT
<213> ORGANISM: Human

<400> SEQUENCE: 20

Met Asn Ser Leu Val Ser Trp Gln Leu Leu Leu Phe Leu Cys Ala Thr
1               5                   10                  15

```
                              -continued

His Phe Gly Glu Pro Leu Glu Lys Val Ala Ser Val Gly Asn Ser Arg
            20                  25                  30

Pro Thr Gly Gln Gln Leu Glu Ser Leu Gly Leu Leu Ala Pro Gly Glu
        35                  40                  45

Gln Ser Leu Pro Cys Thr Glu Arg Lys Pro Ala Ala Thr Ala Arg Leu
    50                  55                  60

Ser Arg Arg Gly Thr Ser Leu Ser Pro Pro Glu Ser Ser Gly Ser
65                  70                  75                  80

Arg Gln Gln Pro Gly Leu Ser Ala Pro His Ser Arg Gln Ile Pro Ala
                85                  90                  95

Pro Gln Gly Ala Val Leu Val Gln Arg Glu Lys Asp Leu Pro Asn Tyr
            100                 105                 110

Asn Trp Asn Ser Phe Gly Leu Arg Phe Gly Lys Arg Glu Ala Ala Pro
        115                 120                 125

Gly Asn His Gly Arg Ser Ala Gly Arg Gly Trp Gly Ala Gly Ala Gly
    130                 135                 140

Gln
145

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: the
      C-terminus of the polypeptide is amide (-CONH2)form

<400> SEQUENCE: 21

Asn Ser Phe Gly Leu Arg Phe
1               5

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: the DNA
      encoding the amino acid sequence shown by SEQ ID NO: 21

<400> SEQUENCE: 22
aactccttcg gcctgcgctt c                                          21
```